(12) United States Patent
Demeule et al.

(10) Patent No.: US 9,687,561 B2
(45) Date of Patent: Jun. 27, 2017

(54) PEPTIDE-DENDRIMER CONJUGATES AND USES THEREOF

(71) Applicant: Angiochem Inc., Montreal (CA)

(72) Inventors: Michel Demeule, Beaconsfield (CA); Alain Larocque, Saint-Laurent (CA); Gaoqiang Yang, Montreal (CA); Sasmita Tripathy, Pierrefonds (CA)

(73) Assignee: Angiochem Inc., Montreal (CA)

( * ) Notice: Subject to any disclaimer, the term of this patent is extended or adjusted under 35 U.S.C. 154(b) by 0 days.

(21) Appl. No.: 14/422,165

(22) PCT Filed: Aug. 14, 2013

(86) PCT No.: PCT/CA2013/050621
§ 371 (c)(1),
(2) Date: Feb. 17, 2015

(87) PCT Pub. No.: WO2014/026283
PCT Pub. Date: Feb. 20, 2014

(65) Prior Publication Data
US 2016/0015823 A1  Jan. 21, 2016

Related U.S. Application Data

(60) Provisional application No. 61/682,991, filed on Aug. 14, 2012.

(51) Int. Cl.
| | | |
|---|---|---|
| *A61K 38/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *A61K 47/48* | (2006.01) | |
| *C07K 14/81* | (2006.01) | |
| *A61K 38/10* | (2006.01) | |

(52) U.S. Cl.
CPC ........ *A61K 47/48253* (2013.01); *A61K 38/10* (2013.01); *A61K 47/482* (2013.01); *A61K 47/48207* (2013.01); *A61K 47/48246* (2013.01); *C07K 14/8117* (2013.01)

(58) Field of Classification Search
CPC ...... A61K 38/00; A61K 47/482; A61K 38/10; A61K 47/48207; C07K 14/515
See application file for complete search history.

(56) References Cited

U.S. PATENT DOCUMENTS

| | | |
|---|---|---|
| 5,258,499 A | 11/1993 | Konigsberg et al. |
| 5,442,043 A | 8/1995 | Fukuta et al. |
| 6,245,359 B1 | 6/2001 | Milstein et al. |
| 6,306,993 B1 | 10/2001 | Rothbard et al. |
| 6,372,250 B1 | 4/2002 | Pardridge |
| 7,115,707 B2 | 10/2006 | Ben-Sasson et al. |
| 7,214,657 B2 | 5/2007 | Kream |
| 7,557,182 B2 | 7/2009 | Beliveau et al. |
| 7,569,544 B2 | 8/2009 | Zankel et al. |
| 7,700,554 B2 | 4/2010 | Beliveau et al. |
| 7,902,156 B2 | 3/2011 | Beliveau et al. |
| 8,530,429 B2 | 9/2013 | Robbins et al. |
| 8,828,925 B2 | 9/2014 | Demeule et al. |
| 9,173,891 B2 | 11/2015 | Castaigne et al. |
| 2003/0129186 A1 | 7/2003 | Beliveau et al. |
| 2004/0146549 A1 | 7/2004 | Ben-Sasson et al. |
| 2005/0026823 A1 | 2/2005 | Zankel et al. |
| 2005/0042227 A1 | 2/2005 | Zankel et al. |
| 2005/0058702 A1 | 3/2005 | Ben-Sasson et al. |
| 2005/0100986 A1 | 5/2005 | Verma et al. |
| 2006/0029609 A1 | 2/2006 | Zankel et al. |
| 2006/0182684 A1 | 8/2006 | Beliveau |
| 2006/0189515 A1 | 8/2006 | Beliveau et al. |
| 2006/0251713 A1 | 11/2006 | Ben-Sasson et al. |
| 2007/0167365 A1 | 7/2007 | Beliveau et al. |
| 2008/0199436 A1 | 8/2008 | Sawada |
| 2008/0213185 A1 | 9/2008 | Hong et al. |
| 2008/0299039 A1 | 12/2008 | Beliveau et al. |
| 2009/0016959 A1 | 1/2009 | Beliveau et al. |
| 2009/0082277 A1 | 3/2009 | Beliveau et al. |
| 2010/0256055 A1 | 10/2010 | Castaigne et al. |
| 2010/0284921 A1 | 11/2010 | Gordon et al. |
| 2010/0297120 A1 | 11/2010 | Beliveau et al. |
| 2011/0039785 A1 | 2/2011 | Beliveau et al. |

(Continued)

FOREIGN PATENT DOCUMENTS

| | | |
|---|---|---|
| CA | 2283474 A1 | 9/1998 |
| CA | 2525236 A1 | 1/2005 |

(Continued)

OTHER PUBLICATIONS

Wood et al., Angew. Chem. Int. Ed., 2005, 44, 6704-6708.*
U.S. Appl. No. 61/138,375, Beliveau et al.
U.S. Appl. No. 61/546,851, filed Oct. 13, 2011, Demeule et al.
Bickel et al., "Delivery of peptides and proteins through the blood-brain barrier," Adv Drug Deliv Rev. 46(1-3):247-279 (2001).
Dagenais et al., "Development of an in situ mouse brain perfusion model and its application to mdr1a P-glycoprotein-deficient mice," J Cereb Blood Flow Metab. 20(2):381-386 (2000).
Dehouck et al., "A new function for the LDL receptor: transcytosis of LDL across the blood-brain barrier," J Cell Biol. 138(4):877-889 (1997).
Dehouck et al., "An easier, reproducible, and mass-production method to study the blood-brain barrier in vitro," J Neurochem. 54(5):1798-1801 (1990).
Dehouck et al., "Drug transfer across the blood-brain barrier: correlation between in vitro and in vivo models," J Neurochem. 58(5):1790-1797 (1992).

(Continued)

*Primary Examiner* — Hasan Ahmed
*Assistant Examiner* — Kaipeen Yang
(74) *Attorney, Agent, or Firm* — Clark & Elbing LLP; Kristina Bieker-Brady

(57) ABSTRACT

The invention relates to dendrimers conjugated to multiple targeting peptides and one or more therapeutic, diagnostic, or imaging agents for delivery of such agents across the blood-brain barrier and into certain cell types including, cells expressing the LRP-1 receptor. Also described are methods of making compounds that comprise dendrimers conjugated to targeting peptides and therapeutic, diagnostic, or imaging agents.

19 Claims, 2 Drawing Sheets

(56) References Cited

U.S. PATENT DOCUMENTS

| | | | |
|---|---|---|---|
| 2011/0171128 A1 | 7/2011 | Beliveau et al. | |
| 2011/0218152 A1 | 9/2011 | Beliveau et al. | |
| 2011/0305750 A1 | 12/2011 | Beliveau et al. | |
| 2011/0318322 A1 | 12/2011 | Bossard | |
| 2012/0015876 A1 | 1/2012 | Castaigne et al. | |
| 2015/0037311 A1 | 2/2015 | Boivin et al. | |

FOREIGN PATENT DOCUMENTS

| | | |
|---|---|---|
| CN | 101160403 A | 4/2008 |
| CN | 101262890 A | 9/2008 |
| CN | 102406949 A | 4/2012 |
| CN | 102552928 A | 7/2012 |
| CN | 102614105 A | 8/2012 |
| EP | 2333074 A1 | 6/2011 |
| WO | WO-96/35788 A2 | 11/1996 |
| WO | WO-96/39183 A1 | 12/1996 |
| WO | WO-97/33996 A2 | 9/1997 |
| WO | WO-97/40854 A2 | 11/1997 |
| WO | WO-03/009815 A2 | 2/2003 |
| WO | WO-03/032913 A2 | 4/2003 |
| WO | WO-2004/060403 A2 | 7/2004 |
| WO | WO-2004/108071 A2 | 12/2004 |
| WO | WO-2005/002515 A2 | 1/2005 |
| WO | WO-2005/014625 A1 | 2/2005 |
| WO | WO-2006/086870 A1 | 8/2006 |
| WO | WO-2007/009229 A1 | 1/2007 |
| WO | WO-2007/044323 A2 | 4/2007 |
| WO | WO-2008/046228 A1 | 4/2008 |
| WO | WO-2008/144919 A1 | 12/2008 |
| WO | WO-2009/079790 A1 | 7/2009 |
| WO | WO-2009/127072 A1 | 10/2009 |
| WO | WO-2010/043047 A1 | 4/2010 |
| WO | WO-2010/043049 A1 | 4/2010 |
| WO | WO-2010/063122 A1 | 6/2010 |
| WO | WO-2010/063123 A1 | 6/2010 |
| WO | WO-2010/063124 A1 | 6/2010 |
| WO | WO-2010/069074 A1 | 6/2010 |
| WO | WO-2010/121379 A1 | 10/2010 |
| WO | WO-2010/142035 A1 | 12/2010 |
| WO | WO-2011/000095 A1 | 1/2011 |
| WO | WO-2011/008823 A2 | 1/2011 |
| WO | WO-2011/041897 A1 | 4/2011 |
| WO | WO-2011/153642 A1 | 12/2011 |
| WO | WO-2012/000118 A1 | 1/2012 |
| WO | WO-2012/037687 A1 | 3/2012 |
| WO | WO-2012/162807 A1 | 12/2012 |
| WO | WO-2013/056096 A1 | 4/2013 |
| WO | WO-2013/078562 A2 | 6/2013 |
| WO | WO-2013/078564 A2 | 6/2013 |
| WO | WO-2013/185235 A1 | 12/2013 |
| WO | WO-2014/026283 A1 | 2/2014 |
| WO | WO-2014/026286 A1 | 2/2014 |
| WO | WO-2014/071531 A1 | 5/2014 |
| WO | WO-2014/076655 A1 | 5/2014 |
| WO | WO-2014/082184 A1 | 6/2014 |
| WO | WO-2014/194428 A1 | 12/2014 |
| WO | WO-2014/194429 A1 | 12/2014 |

OTHER PUBLICATIONS

Demeule et al., "High transcytosis of melanotransferrin (P97) across the blood-brain barrier," J Neurochem. 83(4):924-933 (2002).
Demeule et al., "Identification and design of peptides as a new drug delivery system for the brain," J Pharmacol Exp Ther. 324(3):1064-1072 (2008).
Demeule et al., "Isolation of endothelial cells from brain, lung, and kidney: expression of the multidrug resistance P-Glycoprotein isoforms," Biochem Biophys Res Commun. 281(3):827-834 (2001).
Fillebeen et al., "Receptor-mediated transcytosis of lactoferrin through the blood-brain barrier," J Biol Chem. 274(11):7011-7017 (1999).
Fromm, "P-glycoprotein: a defense mechanism limiting oral bioavailability and CNS accumulation of drugs," Int J Clin Pharmacol Ther. 38(2):69-74 (2000).
Grabb et al., "Neoplastic and pharmacological influence on the permeability of an in vitro blood-brain barrier," J Neurosurg. 82(6):1053-1058 (1995).
Hawkins et al., "The blood-brain barrier/neurovascular unit in health and disease," Pharmacol Rev. 57(2):173-185 (2005).
Hussain et al., "The mammalian low-density lipoprotein receptor family," Annu Rev Nutr. 19:141-172 (1999).
Ke et al., "Gene delivery targeted to the brain using an angiopep-conjugated polyethyleneglycol-modified polyamidoamine dendrimer," Biomaterials. 30(36):6976-85 (2009).
Kounnas et al, "LDL receptor-related protein, a multifunctional ApoE receptor, binds secreted beta-amyloid precursor protein and mediates Its degradation," Cell. 82(2):331-340 (1995).
Koziara et al., "In situ blood-brain barrier transport of nanoparticles," Pharm Res. 20(11):1772-1778 (2003).
Kreuter et al., "Apolipoprotein-mediated transport of nanoparticle-bound drugs across the blood-brain barrier," J Drug Target. 10(4):317-325 (2002).
Kreuter et al., "Direct evidence that polysorbate-80-coated poly(Butylcyanoacrylate) nanoparticles deliver drugs to the CNS via specific mechanisms requiring prior binding of drug to the nanoparticles," Pharm Res. 20(3):409-416 (2003).
Kreuter, Nanoparticulate carriers for drug delivery to the brain. Nanoparticles as Drug Carriers. Torchilin VP, 527-547 (2006).
Lai et al., "The critical component to establish in vitro BBB model: pericyte," Brain Res Rev. 50(2):258-265 (2005).
Larsson, "Megalin, an endocytic receptor with signalling potential," Acta Universitatis Upsaliensis Uppsala (58 pages) (2006).
Marinò et al., "Megalin-mediated transcytosis of thyroglobulin by thyroid cells is a calmodulin-dependent process," Thyroid. 10(6):461-469 (2000).
Marinò et al., "Transcytosis of retinol-binding protein across renal proximal tubule cells after megalin (gp 330)-mediated endocytosis," J Am Soc Nephrol. 12:637-648 (2001).
Martel et al., "Transport of apolipoproteins E and J at the blood-brain barrier relevance to Alzheimer's disease," S.T.P. Pharma Sciences. 7(1):28-36 (1997).
McCarty, "Cell biology of the neurovascular unit: implications for drug delivery across the blood-brain barrier," Assay Drug Dev Technol. 3(1):89-95 (2005).
Moestrup et al., "Evidence that epithelial glycoprotein 330/Megalin mediates uptake of polybasic drugs," J Clin Invest. 96(3):1404-1413 (1995).
Orlando et al., "Identification of the second cluster of ligand-binding repeats in megalin as a site for receptor-ligand interactions," Proc Natl Acad Sci USA. 94(6):2368-2373 (1997).
Pan et al., "Efficient transfer of receptor-associated protein (RAP) across the blood-brain barrier," J Cell Sci. 117(21):5071-5078 (2004).
Pardridge, "Blood-brain barrier biology and methodology," J Neurovirol. 5(6):556-569 (1999).
Pardridge, "CNS drug design based on principles of blood-brain barrier transport," J Neurochem. 70(5):1781-1792 (1998).
Pardridge, "Drug targeting to the brain," Pharm Res. 24(9):1733-1744 (2007).
Prince et al., "Lipoprotein receptor binding, cellular uptake, and lysosomal delivery of fusions between the receptor-associated protein (RAP) and alpha-L-Iduronidase or Acid alpha-Glucosidase," J Biol Chem. 279(33):35037-35046 (2004).
Ramakrishnan, "The role of P-glycoprotein in the blood-brain barrier," Einstein Q J Biol Med. 19:160-165 (2003).
Rawat et al., "Lipid carriers: a versatile delivery vehicle for proteins and peptides," Yakugaku Zasshi. 128(2):269-280 (2008).
Scherrmann, "Drug delivery to brain via the blood-brain barrier," Vascul Pharmacol. 38(6):349-354 (2002).
Schinkel, "P-Glycoprotein, a gatekeeper in the blood-brain barrier," Adv Drug Deliv Rev. 36(2-3):179-194 (1999).
Seidel et al., "Effects of trasylol on the blood-brain barrier in rats," Naunyn-Schmiedebergs Arch Pharmacol. 284(4):R73 (Abstract Only) (1974).

(56) References Cited

OTHER PUBLICATIONS

Smith, "Brain perfusion systems for studies of drug uptake and metabolism in the central nervous system," Pharm Biotechnol. 8:285-307 (1996).
Tamai et al., "Structure-internalization relationship for adsorptive-mediated endocytosis of basic peptides at the blood-brain barrier," J Pharmacol Exp Ther. 280(1):410-415 (1997).
Temsamani et al., "Vector-mediated drug delivery to the brain," Expert Opin Biol Ther. 1(5):773-782 (2001).
Terasaki et al., "New approaches to in vitro models of blood-brain barrier drug transport," Drug Discov Today. 8(20):944-954 (2003).
Triguero et al., "Capillary depletion method for quantification of blood-brain barrier transport of circulating peptides and plasma proteins," J Neurochem. 54(6):1882-1888 (1990).
Veronese et al., "PEGylation, successful approach to drug delivery," Drug Discov Today. 10(21):1451-1458 (2005).
Wang et al., "DNA/dendrimer complexes mediate gene transfer into murine cardiac transplants ex Vivo," Mol Ther. 2(8):602-608 (2000).
Witt et al., "Peptide drug modifications to enhance bioavailability and blood-brain barrier permeability," Peptides. 22(12):2329-2343 (2001).
Yepes et al., "Tissue-type plasminogen activator induces opening of the blood-brain barrier via the LDL receptor-related protein," J Clin Invest. 112(10):1533-1540 (2003).
Zlokovic et al., "Glycoprotein 330/Megalin: probable role in receptor-mediated transport of apolipoprotein J alone and in a complex with Alzheimer disease amyloid Beta at the blood-brain and blood cerebrospinal fluid barriers," Proc Natl Acad Sci U S A. 93:4229-4234 (1996).
Gabathuler, "Approaches to transport therapeutic drugs across the blood-brain barrier to treat brain diseases," Neurobiol Dis. 37(1):48-57 (2010).
Hein et al., "Click chemistry, a powerful tool for pharmaceutical sciences," Pharm Res. 25(10):2216-2230 (2008).
Demeule et al., "ANG2002: A new Angiochem-modified neurotensin with increased brain penetration and analgesic properties," Program No. 374.11/QQ6 2010 Neuroscience Meeting Planner, San Diego, CA: Society for Neuroscience (2010) (5 pages).
Lachowicz et al., "Analgesic properties of a novel brain-penetrant Angiopep-2-neurotensin derivative (ANG2002) for treating chronic pain," Program No. 173.28/AA9 2012 Neuroscience Meeting Planner, New Orleans, LA: Society for Neuroscience (2012) (5 pages).
Pardridge et al., "Selective transport of an anti-transferrin receptor antibody through the blood-brain barrier in vivo," J Pharmacol Exp Ther. 259(1):66-70 (1991).
Pardridge, "Vector-mediated drug delivery to the brain," Adv Drug Deliv Rev. 36(2-3):299-321 (1999).
Pardridge et al. "Combined use of carboxyl-directed protein pegylation and vector-mediated blood-brain barrier drug delivery system optimizes brain uptake of brain-derived neurotrophic factor following intravenous administration," Pharm Res. 15(4):576-582 (1998).
Pathan et al. "CNS drug delivery systems: novel approaches," Recent Pat Drug Deliv Formul. 3(1):71-89 (2009).
Shao et al., "Angiopep-2 modified PE-PEG based polymeric micelles for amphotericin B delivery targeted to the brain," J Control Release. 147(1):118-26 (2010).
Zhang et al. "In vitro gene delivery using polyamidoamine dendrimers with a trimesyl core," Biomacromolecules. 6(1):341-350 (2005).
International Search Report and Written Opinion for International Application No. PCT/CA2013/050453, mailed Sep. 3, 2013 (17 pages).
Chu et al., "Detection of soluble P-glycoprotein in culture media and extracellular fluids," Biochem Biophys Res Commun. 203(1):506-512 (1994).
Cui et al., "PAMAM-drug complex for delivering anticancer drug across blood-brain barrier in-vitro and in-vivo," Afr J Pharm Pharmacol. 3(5):227-233 (2009).

Svenson et al., "Dendrimers in biomedical applications—reflections on the field," Adv Drug Deliv Rev. 57(15):2106-2129 (2005).
Kurzrock et al., "ANG1005: Results of a Phase I study in patients with advanced solid tumors and metastatic brain cancer," Poster B168, ACCR/NCI/EORTC Annual Meeting (2009) (2 pages).
Anonymous, "Blood-Brain Barrier Tackled," <http://www.ecancermedicalscience.com/news-insider-news.asp?itemId-326>, published Oct. 22, 2008 (2 pages).
Bertrand et al., "Transport characteristics of a novel peptide platform for CNS therapeutics," J Cell Mol Med. 14(12):2827-39 (2010).
Ché et al., "New Angiopep-modified doxorubicin (ANG1007) and etoposide (ANG 1009) chemotherapeutics with increased brain penetration" J Med Chem. 53(7):2814-24 (2010).
Demeule et al., "Involvement of the low-density lipoprotein receptor-related protein in the transcytosis of the brain delivery vector angiopep-2," J Neurochem. 106(4):1534-44 (2008).
Demeule et al., "Drug transport to the brain: key roles for the efflux pump P-glycoprotein in the blood-brain barrier," Vascul Pharmacol. 38(6):339-48 (2002).
Li et al., "Expression of alpha2-macroglobulin receptor/low density lipoprotein receptor-related protein on surfaces of tumour cells: a study using flow cytometry," Cancer Lett. 111(1-2):199-205 (1997).
Demeule et al., "Conjugation of a brain-penetrant peptide with neurotensin provides antinociceptive properties," J Clin Invest. 124(3):1199-1213 (2014) (15 pages).
Wei et al., "Retro-inverso isomer of Angiopep-2: a stable d-peptide ligand inspires brain-targeted drug delivery," Mol Pharm. 11(10):3261-3268 (2014) (8 pages).
Gaillard et al., "Targeted delivery across the blood-brain barrier," Expert Opin Drug Deliv. 2(2):299-309 (2005).
Régina et al., "Antitumour activity of ANG1005, a conjugate between paclitaxel and the new brain delivery vector Angiopep-2," Br J Pharmacol. 155(2):185-97 (2008).
Castaigne et al., "425 POSTER ANG1005: Preliminary clinical safety and tolerability in patients with recurrent malignant glioma," Eur J Cancer. 6(12):133-134 (2008).
Kurzrock et al., "424 POSTER ANG1005, an Angiopep-2/paclitaxel conjugate: the first clinical trial in patients with advanced cancer and brain metastases: Preliminary safety and tolerability data," Eur J Cancer. 6(12):133 (2008).
Gabathuler et al., "117 POSTER ANG1005, Paclitaxel conjugated to the angiopep brain transport vector for the treatment of brain cancer: preclinical studies," Eur J Cancer. 6(12):38-9 (2008).
Gabathuler et al., "147 POSTER A new Taxol delivery system for the treatment of brain primary or metastatic tumors," Eur J Cancer. 4(12):47-8 (2006).
International Search Report for International Application No. PCT/CA2014/050524, dated Aug. 28, 2014 (13 pages).
International Search Report for International Application No. PCT/CA2014/050523, dated Aug. 1, 2014 (8 pages).
Office Action and its English translation for Russian Patent Application No. 2012103240, dated Aug. 14, 2014 (9 pages).
Extended European Search Report for European Patent Application No. 10766565.5, mailed Nov. 10, 2014 (5 pages).
Extended European Search Report for European Patent Application No. 10793472.1, mailed Jan. 13, 2015 (9 pages).
Office Action for Russian Patent Application No. 2012103240, mailed Apr. 10, 2015 (6 pages).
Xin et al., "The brain targeting mechanism of Angiopep-conjugated poly(ethylene glycol)-co-poly(epsilon-caprolactone) nanoparticles," Biomaterials. 33(5):1673-81 (2012).
Supplementary European Search Report for European Patent Application No. 12854302.2, dated Jun. 6, 2015 (3 pages).
International Preliminary Report on Patentability for International Application No. PCT/CA2013/050924, dated Jun. 2, 2015 (11 pages).
International Preliminary Report on Patentability for International Application No. PCT/CA2013/050621, mailed Feb. 26, 2015 (8 pages).
Communication pursuant to Article 94(3) EPC for European Patent Application No. 10821522.9, dated Jun. 16, 2015 (7 pages).

(56) References Cited

OTHER PUBLICATIONS

Nagy et al., "Cytotoxic analogs of luteinizing hormone-releasing hormone containing doxorubicin or 2-pyrrolinodoxorubicin, a derivative 500-1000 times more potent," Proc Natl Acad Sci U S A. 93(14):7269-73 (1996).
Extended European Search Report for European Patent Application No. 13829574.6, dated Feb. 25, 2016 (10 pages).
Arseneault et al., "Synthesis of a controlled three-faced PAMAM particle," Polym Chem 2:2293-8 (2011).
Huang et al., "Dual targeting effect of Angiopep-2-modified, DNA-loaded nanoparticles for glioma," Biomaterials. 32:6832-8 (2011).
Liu et al., "Versatile synthesis of asymmetrical dendron-like/dendron-like poly(epsilon-caprolactone)-b-poly(gamma-benzyl-L-glutamate) block copolymers," Dendritic Polymers. 49(16):3491-8 (2011).
Yan et al., "Imaging brain tumor by dendrimer-based optical/paramagnetic nanoprobe across the blood-brain barrier," Chem Commun. 47:8130-2 (2011).
Examination Report for Australian Patent Application No. 2013302270, dated Feb. 28, 2017 (4 pages).
Wood et al., "A family of hierarchically self-assembling linear-dendritic hybrid polymers for highly efficient targeted gene delivery," Angew Chem Int Ed Engl. 44(41):6704-8 (2005).

\* cited by examiner

PEPTIDE-DENDRIMER CONJUGATES AND USES THEREOF

CROSS-REFERENCE TO RELATED APPLICATIONS

This application claims benefit of U.S. Ser. No. 61/682,991, filed Aug. 14, 2012, the contents of which are incorporated herein by reference.

REFERENCE TO A SEQUENCE LISTING

This application contains a Sequence Listing in computer readable form. The computer readable form is incorporated herein by reference.

BACKGROUND OF THE INVENTION

The invention relates to compounds including dendrimers conjugated to targeting peptides and one or more therapeutic, diagnostic, or imaging agents and uses of such compounds.

The brain is shielded against potentially toxic substances by the presence of two barrier systems: the blood-brain barrier (BBB) and the blood-cerebrospinal fluid barrier (BCSFB). The BBB is considered to be the major route for the uptake of serum ligands since its surface area is approximately 5000-fold greater than that of BCSFB. The brain endothelium, which constitutes the BBB, represents the major obstacle for the use of potential drugs against many disorders of the CNS. As a general rule, only small lipophilic molecules may pass across the BBB, i.e., from circulating systemic blood to brain. Many drugs that have a larger size or higher hydrophobicity show promising results in animal studies for treating CNS disorders. Thus, peptide and protein agents such as those used as therapeutics are generally excluded from transport from blood to brain, owing to the negligible permeability of the brain capillary endothelial wall to these agents.

Therapy of brain diseases can be impaired by the inability of otherwise effective agents such as therapeutic agents to cross the BBB. Thus, new strategies for transporting agents into the brain with high efficiency are desired.

SUMMARY OF THE INVENTION

We have now developed compounds including a dendrimer conjugated to multiple targeting peptides. These compounds are capable of crossing the blood-brain barrier (BBB) or entering particular cell types (e.g., liver, lung, spleen, kidney, and muscle) with enhanced efficiency. When these compounds are joined with (e.g., conjugated to) one or more agents (e.g., therapeutic or diagnostic agents), efficiency of transport of the agent across the BBB or into particular cell types is increased compared to transport of the agent directly linked to a targeting peptide. The present invention also features methods of producing such compounds and the use of such compounds in treatment of disease.

In a first aspect, the invention features a compound including the formula:

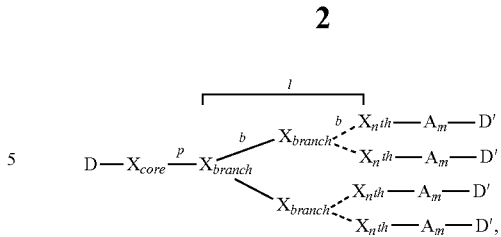

where D is a first agent; $X_{core}$ is a core moiety of a dendrimer with p number of branches where p is an integer from 1 to 12 (e.g., 1, 2, 3, 4, 6, 8, 10, and 12 branches); $X_{branch}$ is a branch moiety of said dendrimer, each $X_{branch}$ is attached to a branch of $X_{core}$ or to a branch of another $X_{branch}$, each $X_{branch}$ has b branches where b is an integer from 2 to 8 (e.g., 2, 4, 6, and 8 branches); l is the number of successive layers of $X_{branch}$ branches of said dendrimer and is an integer from 2 to 10 (e.g., 2, 4, 6, 8, and 10); $X_n^{th}$ is one of n surface branches of said dendrimer and is attached to a b branch of a $X_{branch}$ moiety, where $n=p(b)^l$, and where n is $\leq 512$ (e.g., $\leq 500, \leq 400, \leq 300, \leq 200, \leq 50, \leq 10$, or $\leq 8$ branches); $A_m$ is a targeting peptide attached to an $X_n^{th}$ and comprises an amino acid sequence substantially identical to a sequence selected from the group consisting of SEQ ID NOs:1-105 and 107-117, or a functional fragment thereof, or is a peptide having a formula selected from the group consisting of formulae Ia, Ib, IIa, IIb, and IIc; m is a positive integer $\leq n$; D' is a second agent that is optional and is attached to one or more $A_m$ or may replace one or more $A_m$ and attach directly to one or more $X_n^{th}$, and wherein the number of D' in said compound is $\leq n$; and the molecular weight of the dendrimer, excluding D, D' and $A_m$, is $\leq 500$ kilodalton (e.g., $\leq 500, \leq 400, \leq 300, \leq 200, \leq 100, \leq 50$, or $\leq 20$ kilodaltons).

The compound may also include the formula:

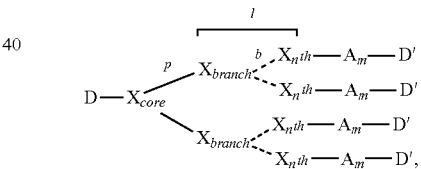

where the compound shares all properties with the above formula with the exceptions that p is an integer between 2 and 6 (e.g., 2, 3, 4, or 6 branches); b is an integer from 2 to 4 (e.g., 2, 3, or 4 branches); and l is an integer from 2 to 5 (e.g., 2, 3, 4, or 5 branches).

In another aspect, the invention features a compound including the formula:

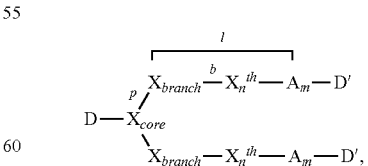

where D is a first agent; $X_{core}$ is a core moiety of a dendrimer with p number of branches where p is an integer from 2 to 6 (e.g., 2, 3, 4, or 6 branches); and where the core moiety is selected from the group consisting of propargylamine, ethylenediamine, triethanolamine, pentaerythritol, azido-propyl(alkyl)amine, hydroxyethyl(alkyl)amine, tetraphenyl methane, trimesoylchloride, diamino hexane, diaminobutane, cystamine, propylenediamine, lysine, and propyleneamine; $X_{branch}$ is a branch moiety of the dendrimer, where each $X_{branch}$ is attached to a branch of $X_{core}$ or to a branch of another $X_{branch}$, and where each $X_{branch}$ has b branches, and where b is an integer from 1 to 4 (e.g., 1, 2, 3, or 4 branches); l is the number of successive layers of $X_{branch}$ branches of the dendrimer and is an integer from 0 to 4 (e.g., 0, 1, 2, 3 or 4 branches); $X_n^{th}$ is one of n surface branches of the dendrimer and is attached to a b branch of a $X_{branch}$ moiety where $n=p(b)^l$, and where n is 256 (e.g., 256, 200, 50, 10, or 8 branches); $A_m$ is a targeting peptide attached to an $X_n^{th}$ and comprises an amino acid sequence substantially identical to a sequence selected from the group consisting of SEQ ID NOs:1-105 and 107-117, or a functional fragment thereof, or is a peptide having a formula selected from the group consisting of formulae Ia, Ib, IIa, IIb, and IIc; m is a positive integer ≤n; D' is a second agent that is optional and is attached to one or more $A_m$ or may replace one or more $A_m$ and attach directly to one or more $X_n^{th}$, and wherein the number of D' in said compound is ≤n; and the molecular weight of the dendrimer, excluding D, D' and $A_m$, is ≤500 kilodalton (e.g., ≤500, ≤400, ≤300, ≤200, ≤100, ≤50, or ≤20 kilodaltons).

The compound may include the formula:

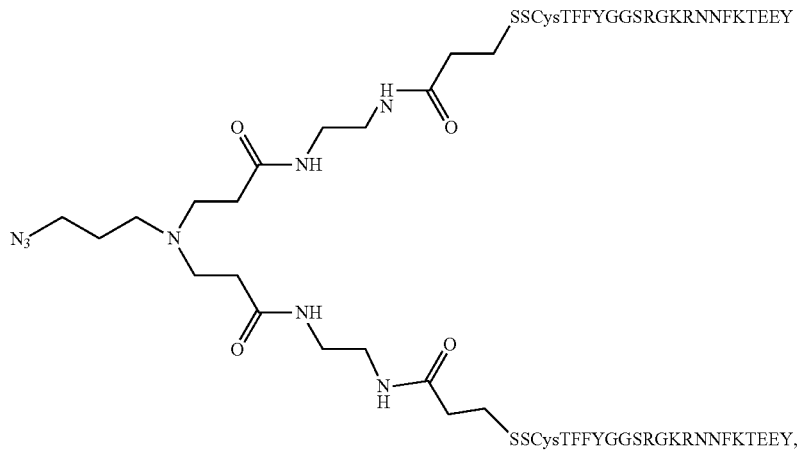

where Cys is cysteine and the "SS" adjacent to Cys represents a disulfide bond, including the sulfur atom of the cysteine.

In one embodiment, n, which is the number of surface branches, can be ≤128 (e.g., ≤64 or ≤32 or ≤16 or ≤8). In another embodiment, the dendrimer part of the compound, excluding the first and second agents and the targeting peptides, of the invention can have a molecular weight of ≤100 kilodaltons (e.g., ≤50 kilodaltons, ≤25 kilodaltons, or ≤10 kilodaltons).

The dendrimer part of the compound may include a core moiety selected from the group consisting of propargylamine, ethylenediamine, triethanolamine, pentaerythritol, azido-propyl(alkyl)amine, hydroxyethyl(alkyl)amine, tetraphenyl methane, trimesoylchloride, diamino hexane, diaminobutane, cystamine, and propylenediamine. These cores are typically used to synthesize the poly(amido amine) (PAMAM) dendrimer. Lysine can also be used as a core moiety to synthesize a polylysine dendrimer. Alternatively the compound can include a propyleneimine to synthesize a POPAM dendrimer.

The compound of the invention can have branch moieties selected from the group consisting of propargylamine, ethylenediamine, triethanolamine, pentaerythritol, propylamine, propyleneimine, azido-propyl(alkyl)amine, hydroxyethyl(alkyl)amine, tetraphenyl methane, trimesoylchloride, diamino hexane, diaminobutane, cystamine, propylenediamine, and lysine. Alternatively, the branch moieties can be derivatives of any one of propargylamine, ethylenediamine, triethanolamine, pentaerythritol, propylamine, propyleneimine, azido-propyl(alkyl)amine, hydroxyethyl(alkyl) amine, tetraphenyl methane, trimesoylchloride, diamino hexane, diaminobutane, cystamine, propylenediamine, and lysine.

One or more terminal branches on the surface of the dendrimer can be functionalized to attach various numbers of targeting peptides (e.g., 2, 4, 6, 8, 12, 16, 32, or 64 targeting peptides). Some or all of the surface branches of the dendrimer can have a targeting peptide attached. The linkage between the targeting peptide can be a cleavable linkage (e.g., a thioester linkage) or a non-cleavable linkage (e.g., a maleimide linkage). The targeting peptide can be attached to the surface branches of the dendrimers via linkers described herein.

The targeting peptides attached to the dendrimer can have an amino acid sequence at least 85% identical to a sequence selected from the group consisting of SEQ ID NOs:1-105 and 107-117 or a fragment thereof. For example, the target peptide can have an amino acid sequence selected from the group consisting of Angiopep-1 (SEQ ID NO:67), Angiopep-2 ($An_2$) (SEQ ID NO:97), cys-Angiopep-2 ($CysAn_2$) (SEQ ID NO:113), Angiopep-2-cys (SEQ ID NO:114), and reversed Angiopep-2 (SEQ ID NO:117). Alternatively, the targeting peptide can have an amino acid sequence selected from the group consisting of Angiopep-1 (SEQ ID NO:67), Angiopep-2 ($An_2$) (SEQ ID NO:97), cys-Angiopep-2 ($CysAn_2$) (SEQ ID NO:113), Angiopep-2-cys (SEQ ID NO:114), and reversed Angiopep-2 (SEQ ID NO:117).

The compound also includes a first agent, D (e.g., a protein, a peptide, a nucleic acid, or a small molecule), attached to the dendrimer via a reactive group (e.g., maleimide, a hydrazide, an azide, a haloacetamide, or an alkoxyamine). The first agent can be attached to the dendrimer via a linker, e.g., pyridinedisulfide, thiosulfonate, vinylsulfonate, isocyanate, NHS ester, imidoester, diazine, hydrazine, thiol, carboxylic acid, a multi-peptide linker, acetylene linkers, cleavable linkers, non-cleavable linker, or a covalent bond. The first agent can be selected from the group consisting of a protein, a peptide, a small molecule, a nucleic acid, a diagnostic agent, an imaging agent, and a therapeutic agent.

The compound also includes an optional second agent, D' (e.g., a protein, a peptide, a nucleic acid, or a small molecule), attached to the dendrimer via a reactive group (e.g., maleimide, a hydrazide, an azide, a haloacetamide, or an alkoxyamine). The second agent can be attached to the dendrimer via a linker, e.g., pyridinedisulfide, thiosulfonate, vinylsulfonate, isocyanate, NHS ester, imidoester, diazine, hydrazine, thiol, carboxylic acid, a multi-peptide linker, acetylene linkers, a cleavable linker, a non-cleavable linker, or a covalent bond. The second agent can be selected from the group consisting of a protein, a small molecule, a nucleic acid, a diagnostic agent, an imaging agent, and a therapeutic agent. The second agent, when present, can be attached to one or more of the $A_m$ peptides, or is attached to one or more of the $X_n^{th}$ branches. The first and second agents may be identical or may be different types of molecules.

The invention includes compounds that may include one or more linkers used to attach the targeting peptide, first agent, and second agent to the dendrimer, wherein the reactive group is present on the linkers.

The compound of the invention includes:

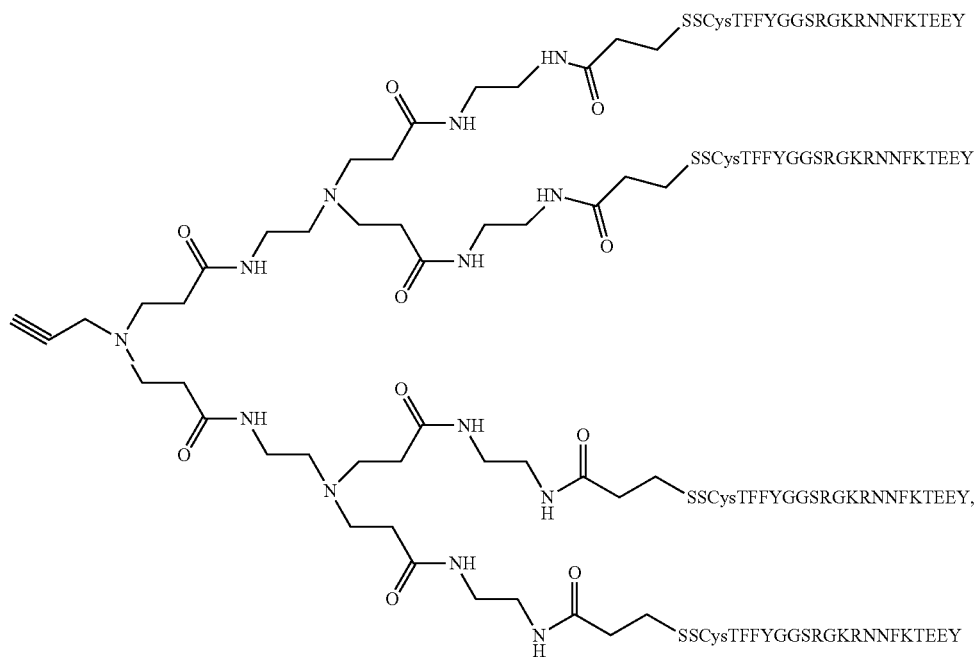

wherein Cys is cysteine and the "SS" adjacent to Cys represents a disulfide bond, including the sulfur atom of the cysteine;

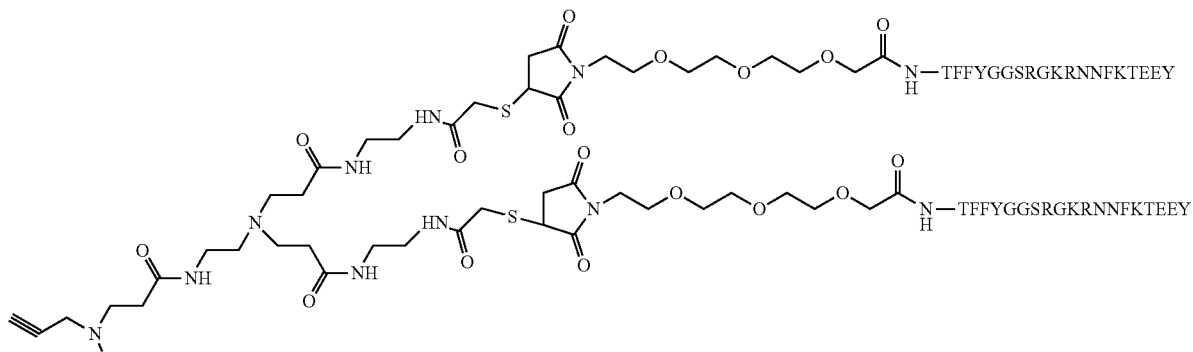

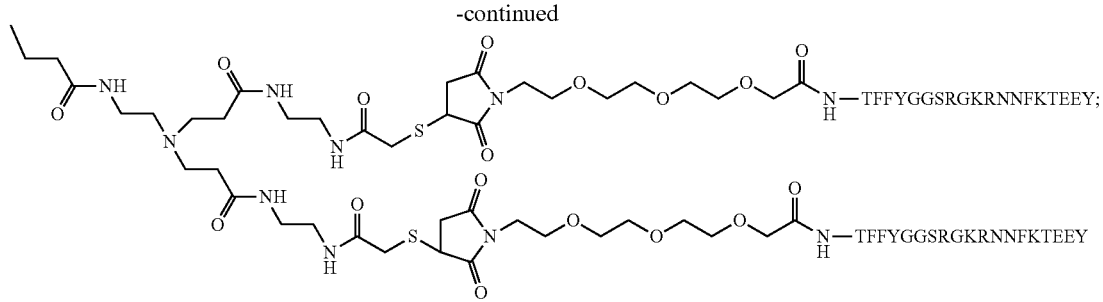
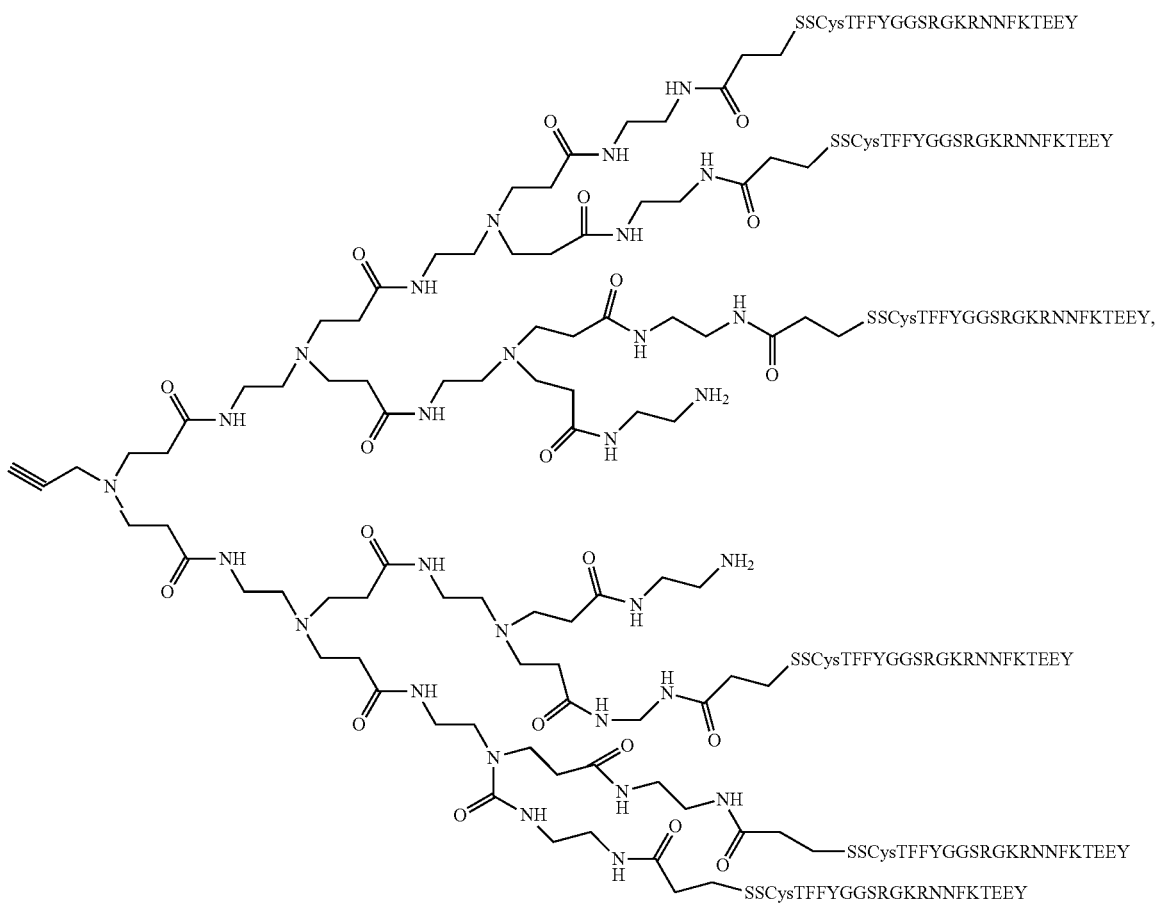
wherein Cys is cysteine and the "SS" adjacent to Cys represents a disulfide bond, including the sulfur atom of the cysteine;

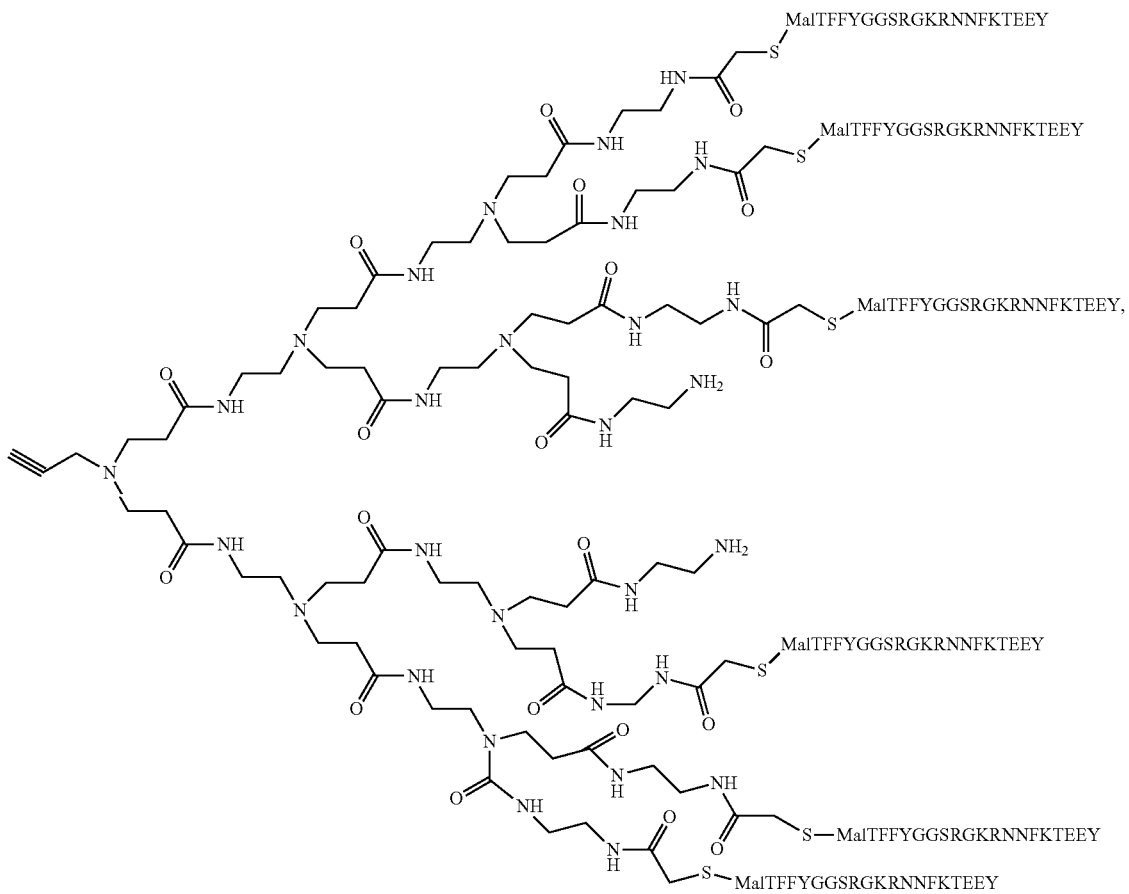
wherein Mal is maleimide;
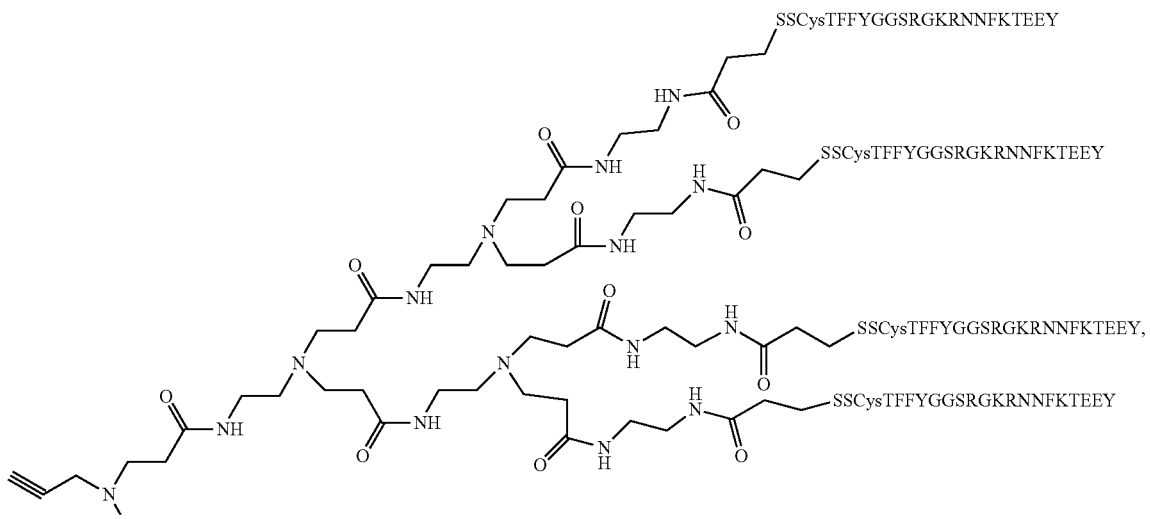

-continued
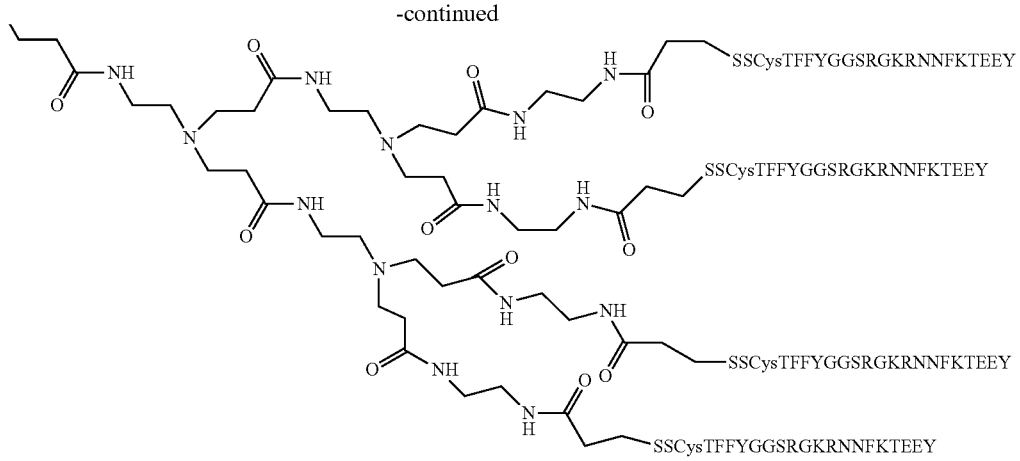
wherein Cys is cysteine and the "SS" adjacent to Cys represents a disulfide bond, including the sulfur atom of the cysteine;
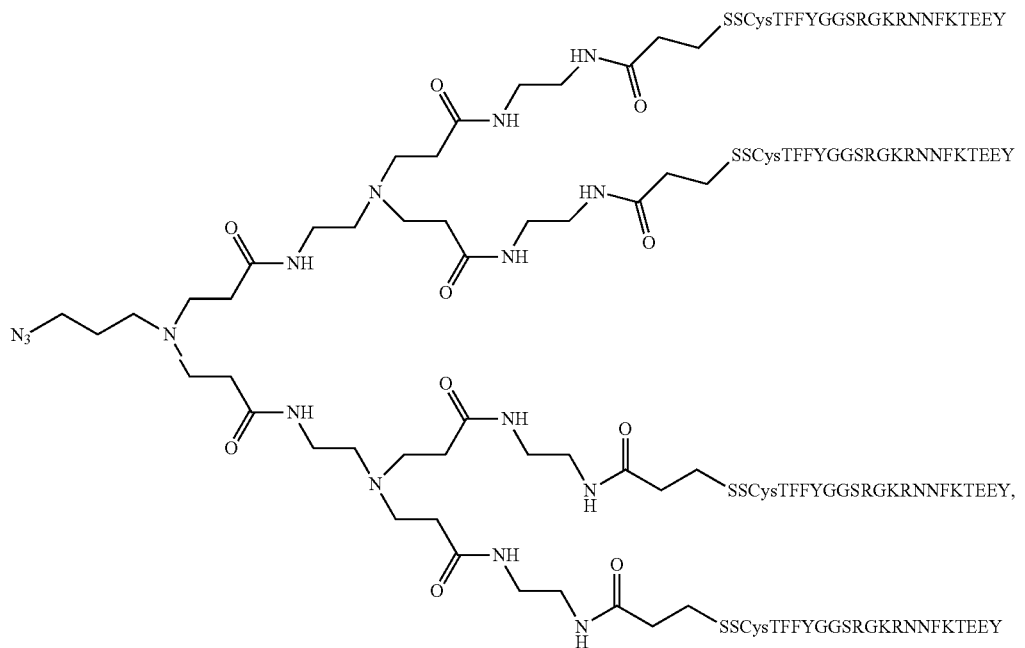
wherein Cys is cysteine and the "SS" adjacent to Cys represents a disulfide bond, including the sulfur atom of the cysteine;

13
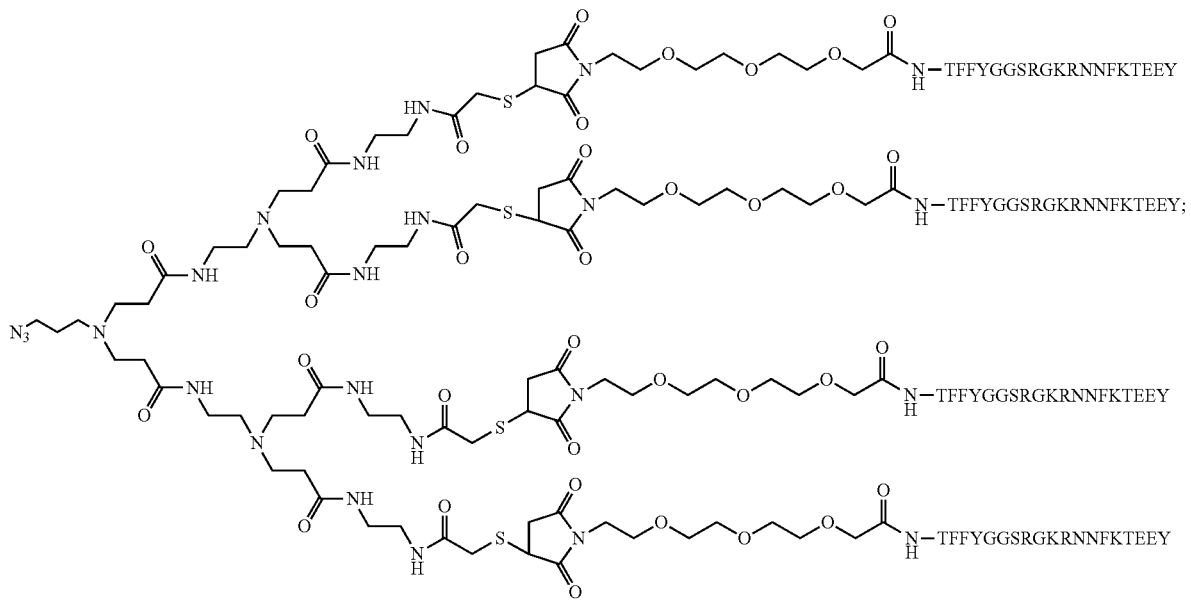
14
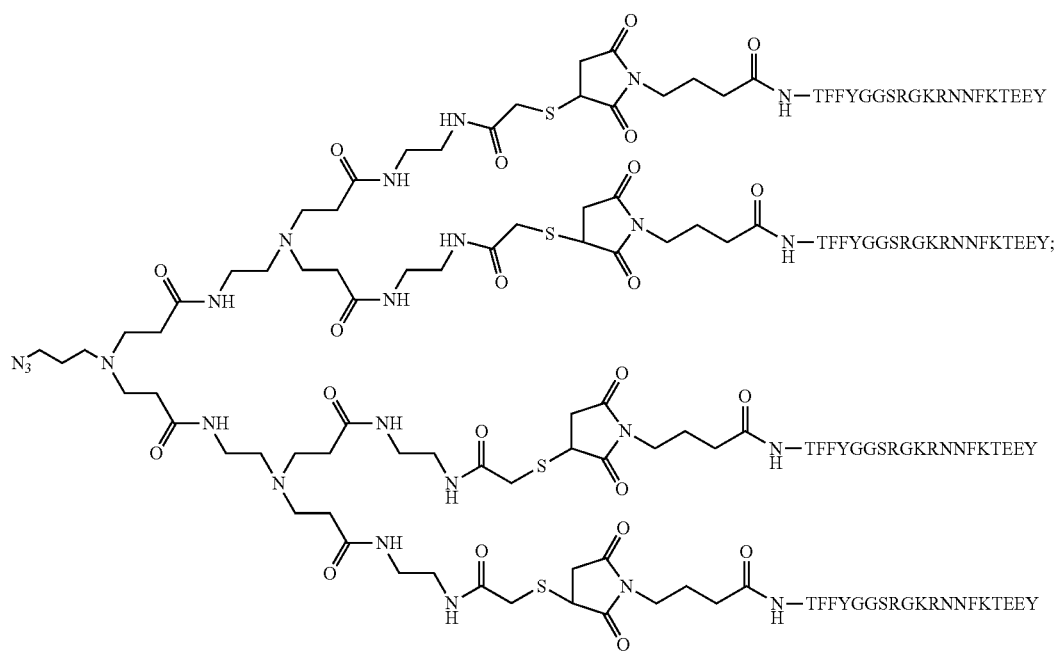

-continued
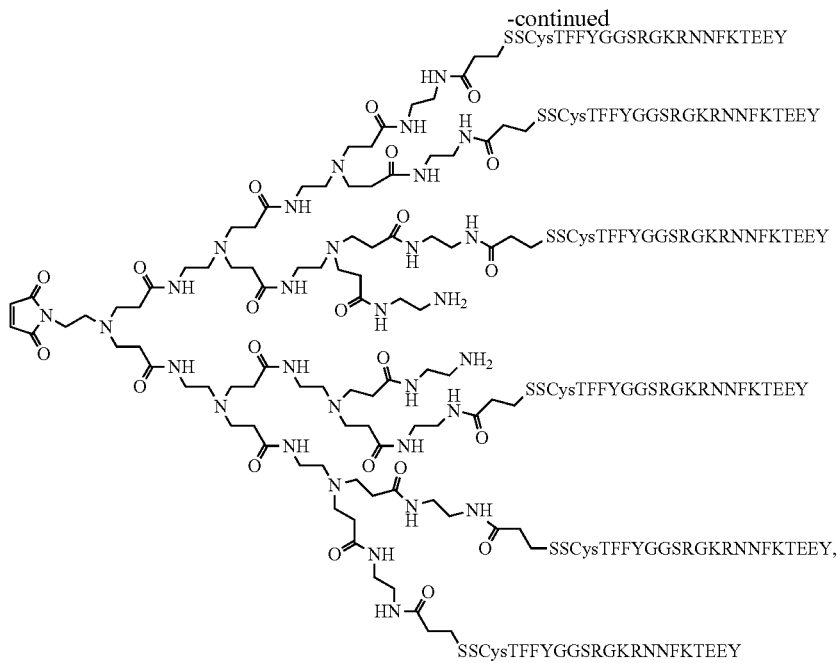
wherein Cys is cysteine and the "SS" adjacent to Cys represents a disulfide bond, including the sulfur atom of the cysteine;
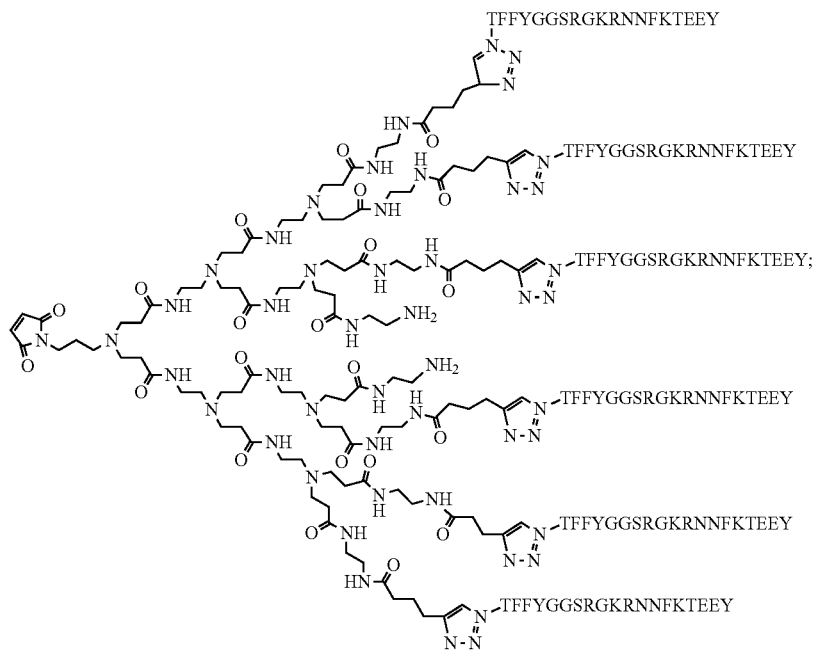

-continued
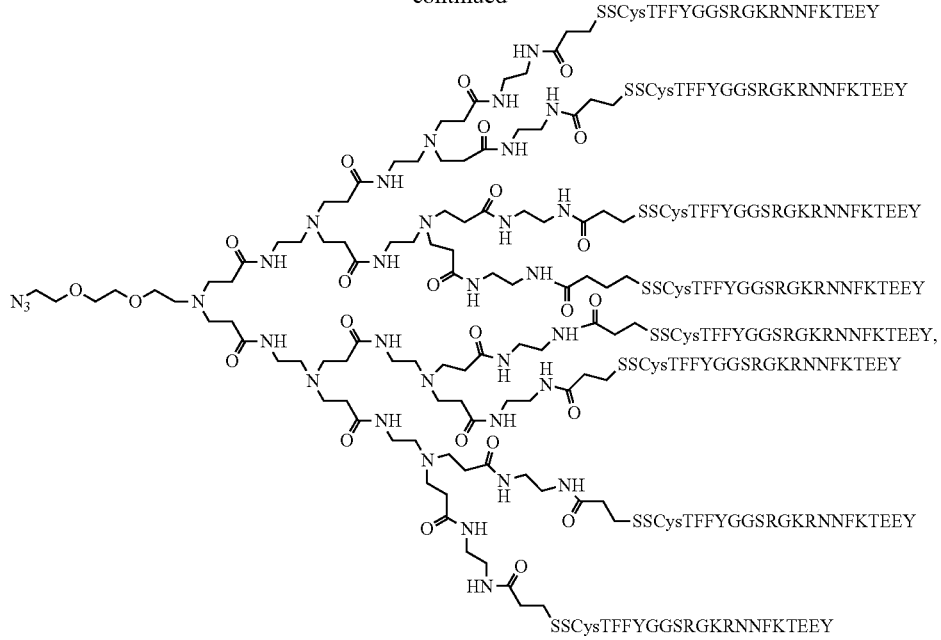
wherein Cys is cysteine, and the "SS" adjacent to Cys represents a disulfide bond, including the sulfur atom of the cysteine;
wherein Cys is cysteine, and the "SS" adjacent to Cys represents a disulfide bond, including the sulfur atom of the cysteine;
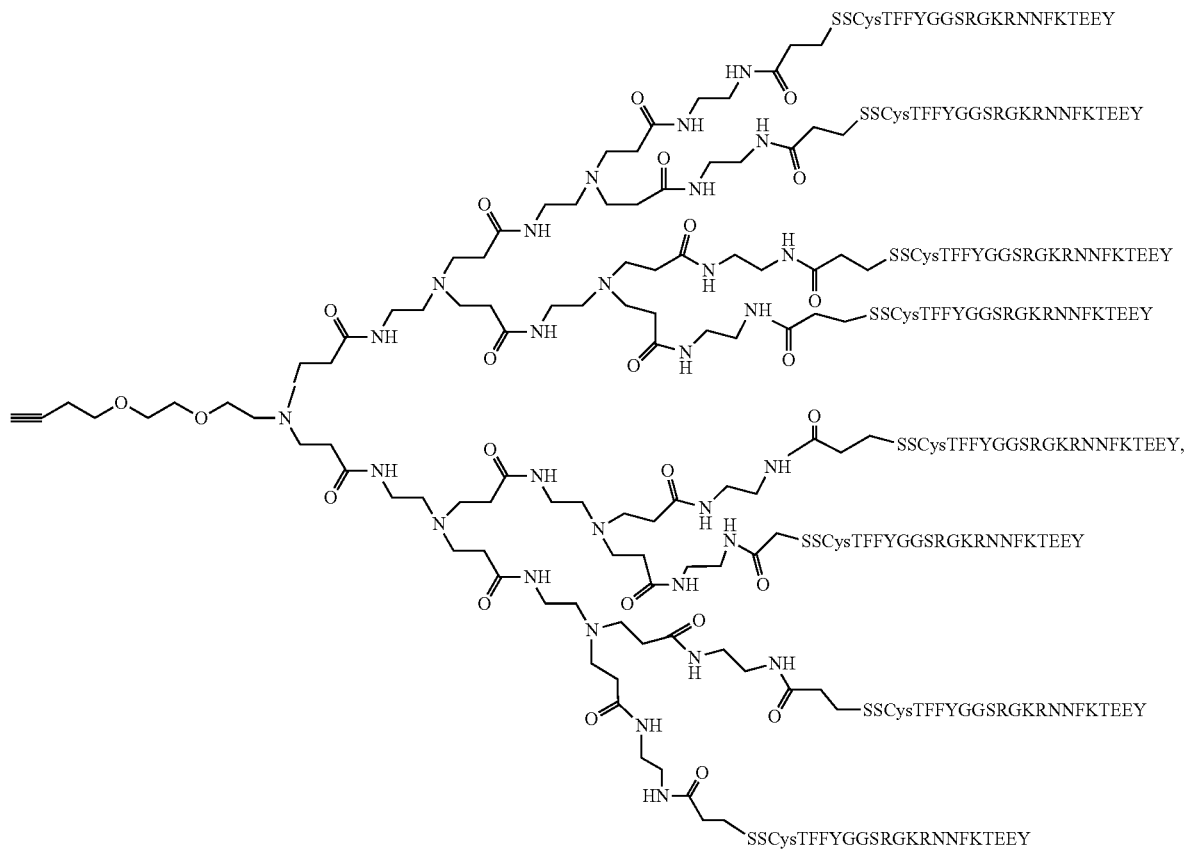

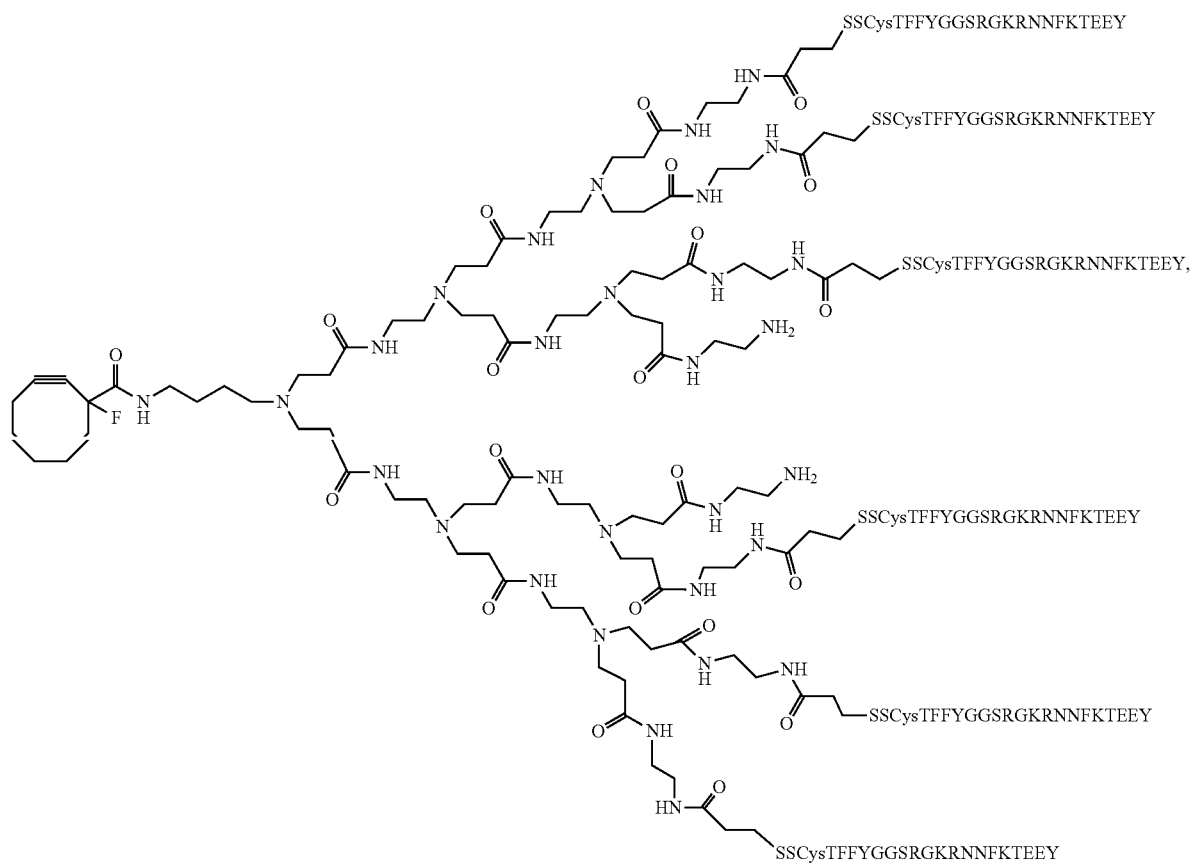
wherein Cys is cysteine, and the "SS" adjacent to Cys represents a disulfide bond, including the sulfur atom of the cysteine;

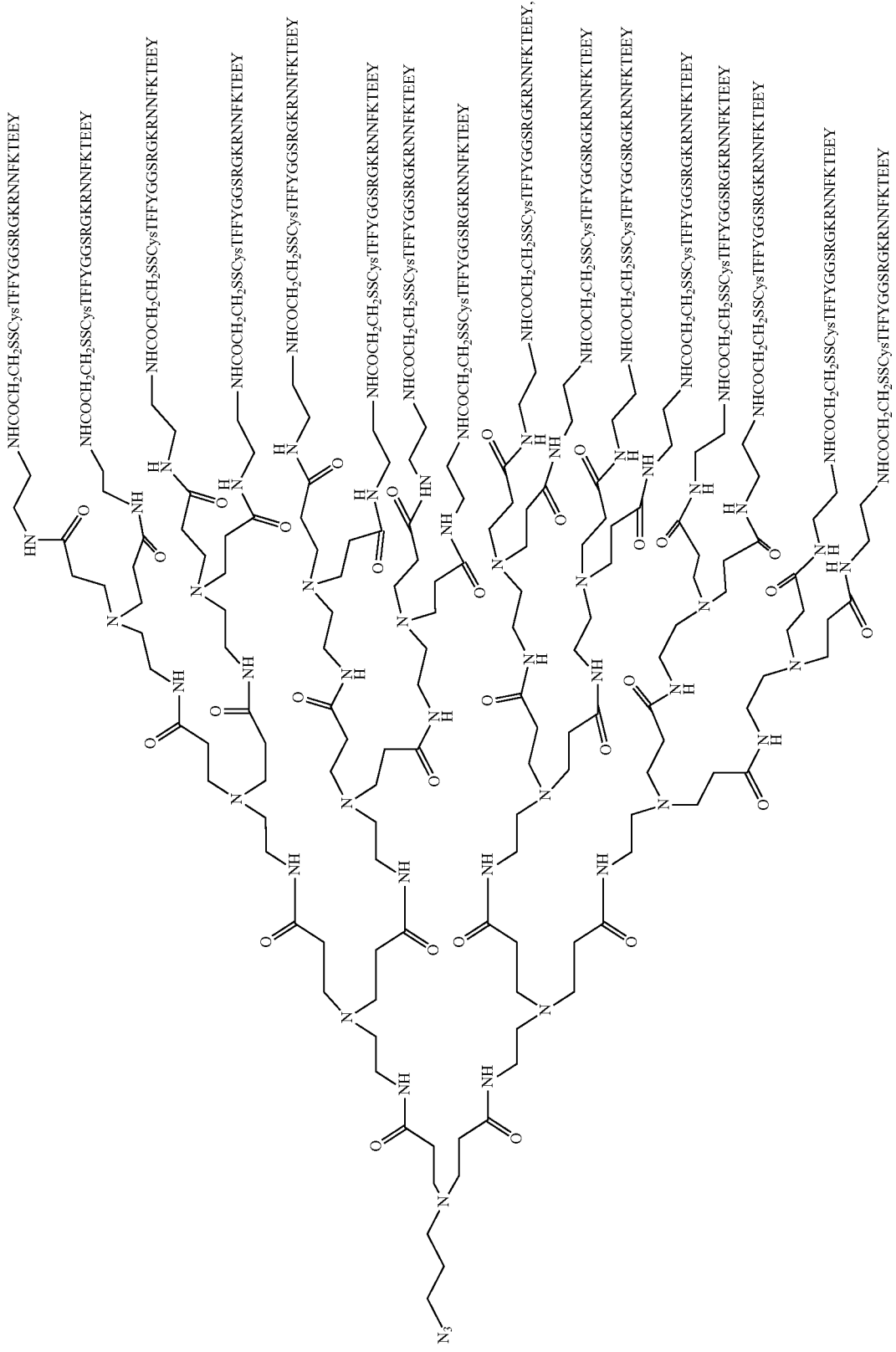

wherein Cys is cysteine and the "SS" adjacent to Cys represents a disulfide bond, including the sulfur atom of the cysteine;

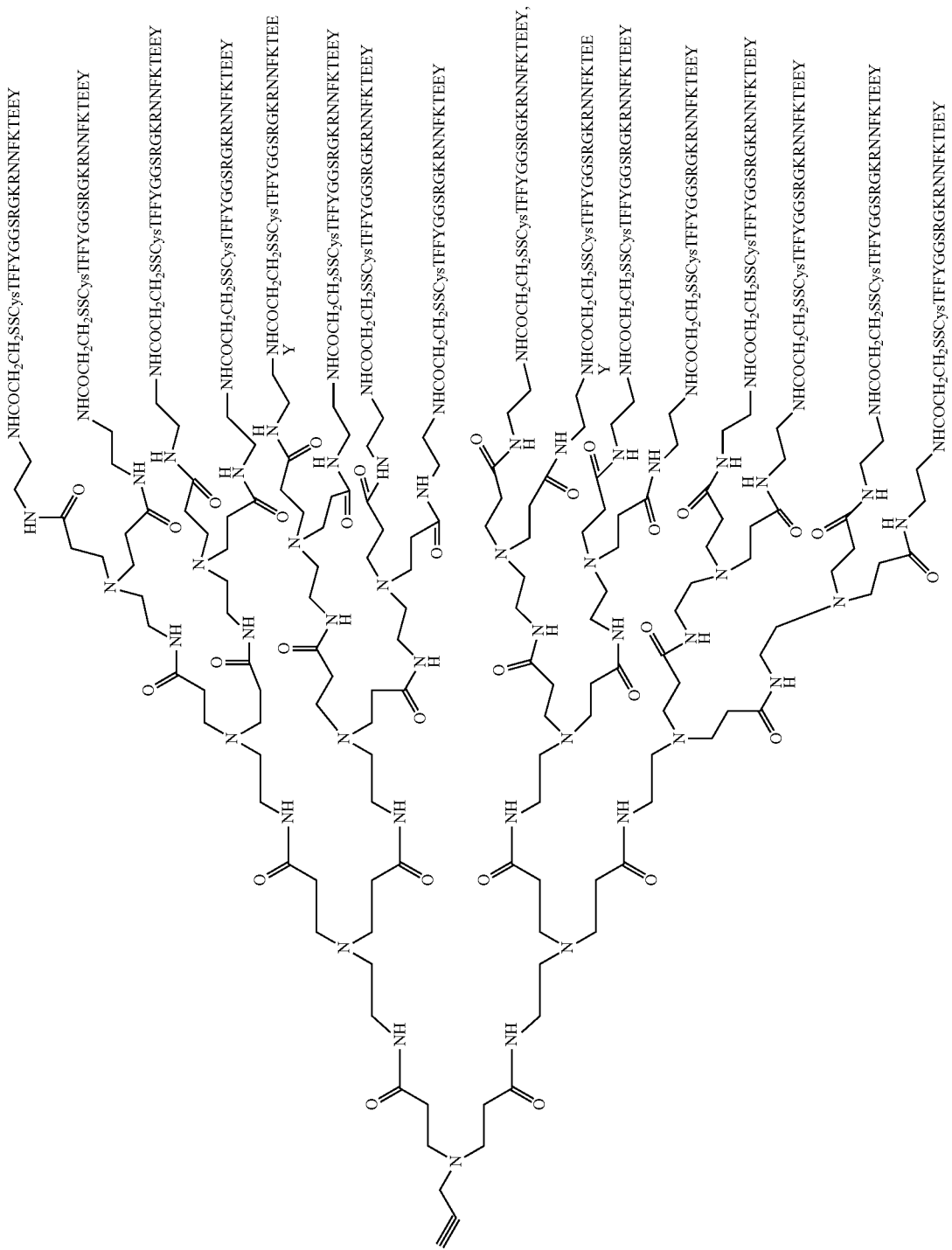

wherein Cys is cysteine, and the "SS" adjacent to Cys represents a disulfide bond, including the sulfur atom of the cysteine;
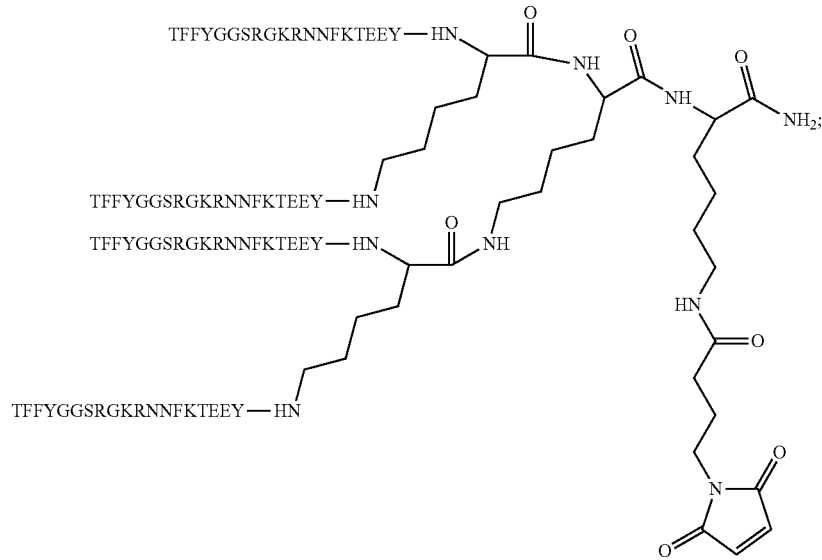
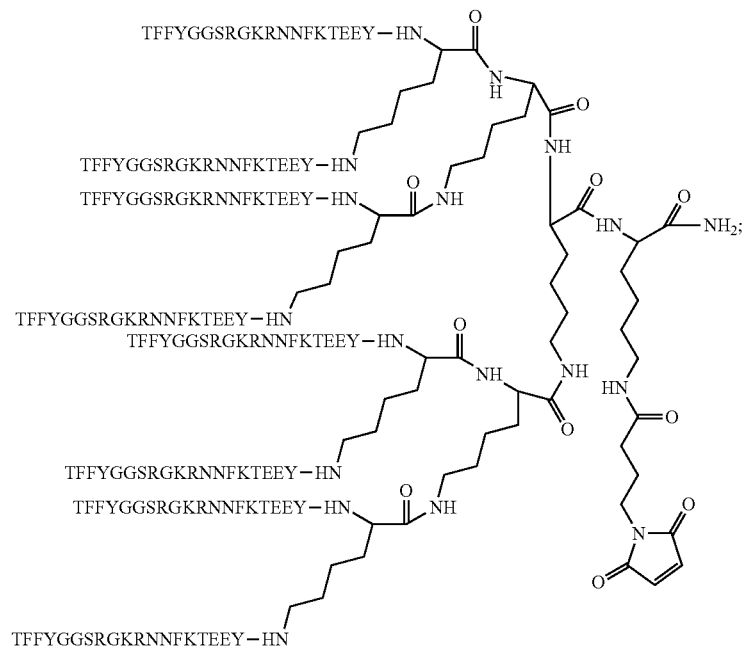

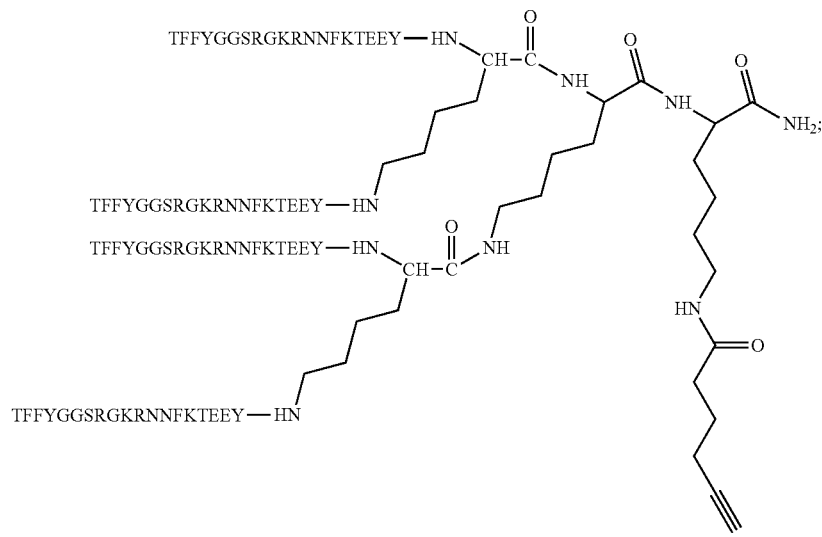
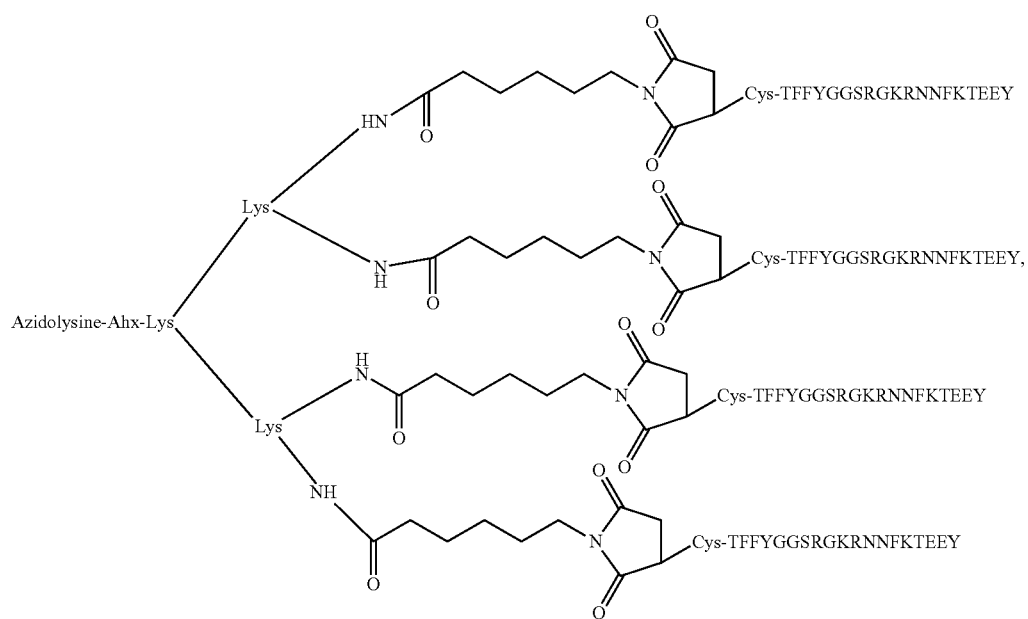
wherein Cys is cysteine, and Ahx is azidohexanoic acid;

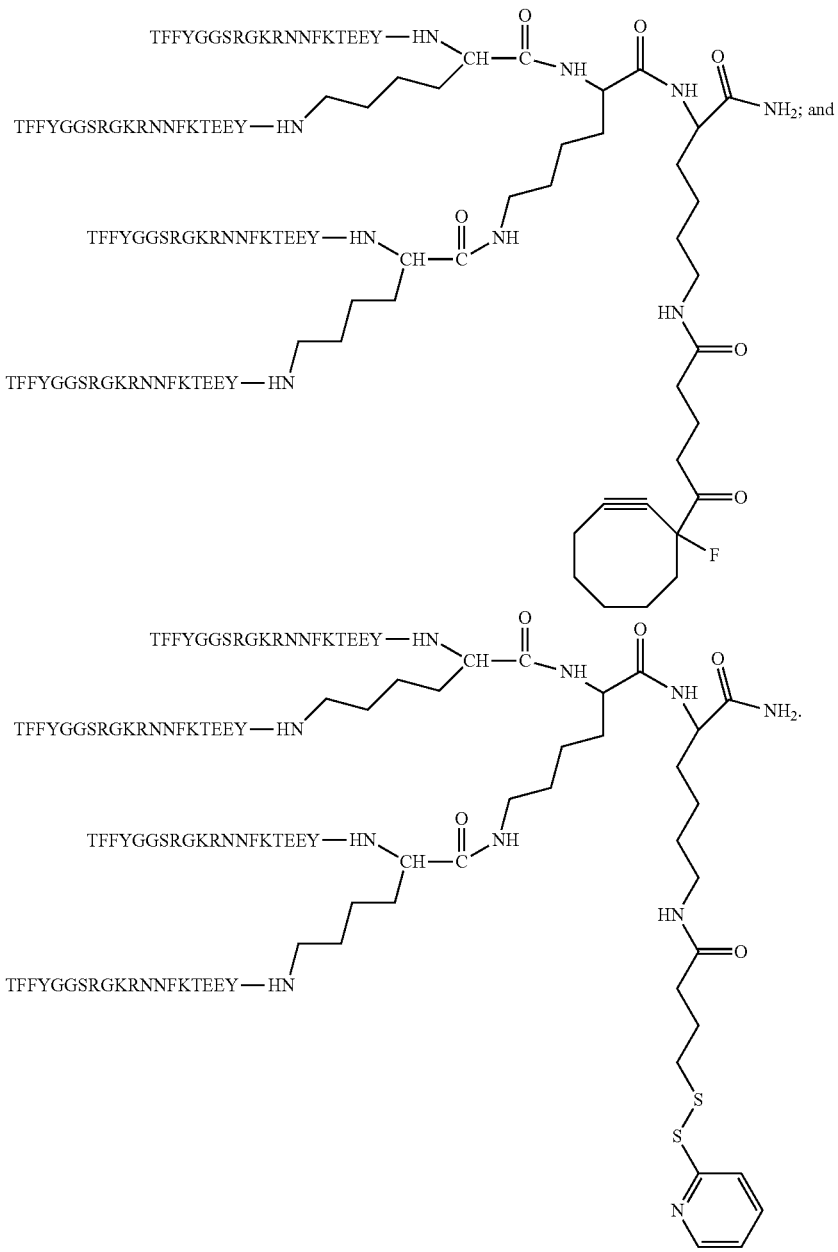

The compound of the invention can enter endothelial cells or enter cells that express the LRP-1 receptor, for example, liver, kidney, and spleen cells. The compound of the invention can also cross the BBB.

The invention also features a method of synthesizing the compound which includes attaching at least two or more targeting peptides, via a linker, to a dendrimer to form a dendrimer-targeting peptide complex; attaching one or more first agents, via a linker, to the dendrimer-targeting peptide complex; and subsequently optionally attaching one or more second agents, via a linker, to this complex. Alternatively, the method can include first attaching at least one first agent to a dendrimer via a reactive group (e.g., a maleimide, a hydrazide, an azide, a haloacetamide, or an alkoxyamine), via a linker, to form a dendrimer-first agent complex; attaching at least two targeting peptides, via a linker, to the dendrimer-first agent complex; and subsequently optionally attaching one or more second agents, via a linker, to this complex.

The method can optionally include steps to attach linkers, for example attaching one or more linkers (e.g., pyridinedisulfide, thiosulfonate, vinylsulfonate, isocyanate, NHS ester, imidoester, diazine, hydrazine, thiol, carboxylic acid, a multi-peptide linker, acetylene, a cleavable linker, a non-cleavable linker, or a covalent bond) to the dendrimer prior to attachment of the targeting peptides; and/or attaching one or more linkers to said dendrimer-targeting peptide complex prior to attaching one or more first or second agents. The linkers can also be attached to a dendrimer prior to attachment of one or more first or second agents or the linkers can be attached to the dendrimer-targeting peptide complex prior to attaching the targeting peptides.

Several methods can be used to functionalize the surface branch and attach targeting peptides to the functionalized surface branch. For example, one method involves reacting the dendrimer with N-succinimidyl 3-(2-pyridyldithio)-propionate followed by reacting with cysteine residue-containing targeting peptides. Alternatively, the targeting peptides can be attached by reacting a dendrimer with N-succinimidyl S-acetylthioacetate followed by reacting with a maleimide derivative of said targeting peptides.

The targeting peptides attached to the dendrimer can have an amino acid sequence at least 85% identical to a sequence selected from the group consisting of SEQ ID NOs:1-105 and 107-117 or a fragment thereof. For example, the targeting peptide can have an amino acid sequence selected from the group consisting of Angiopep-1 (SEQ ID NO:67), Angiopep-2 ($An_2$) (SEQ ID NO:97), cys-Angiopep-2 ($CysAn_2$) (SEQ ID NO:113), Angiopep-2-cys (SEQ ID NO:114), and reversed Angiopep-2 (SEQ ID NO:117). Alternatively, the targeting peptide can have an amino acid sequence selected from the group consisting of Angiopep-1 (SEQ ID NO:67), Angiopep-2 ($An_2$) (SEQ ID NO:97), cys-Angiopep-2 ($CysAn_2$) (SEQ ID NO:113), Angiopep-2-cys (SEQ ID NO:114), and reversed Angiopep-2 (SEQ ID NO:117).

The method includes attachment of a first agent, D to the dendrimer via a reactive group. The first agent can be selected from the group consisting of a protein, a peptide, a small molecule, a nucleic acid, a diagnostic agent, an imaging agent, and a therapeutic agent.

The method also includes attachment of an optional second agent, D' to the dendrimer or the targeting peptide via a reactive group. The second agent can be selected from the group consisting of a protein, a small molecule, a nucleic acid, a diagnostic agent, an imaging agent, and a therapeutic agent. The second agent, when present, can be attached to one or more of the $A_m$ peptides, or is attached to one or more of the $X_n^{th}$ branches. The first and second agents may be identical or may be different types of molecules. The addition of D and D' may optionally involve one or more linkers which are described above.

The method also includes synthesis of a pharmaceutically acceptable salt of the compound of the invention.

By "dendrimer" is meant a synthetically produced molecule with one or more branches radiating from a core moiety. The branches include functional groups for attaching one or more targeting peptides and/or one or more agents to the dendrimer. As used herein, the term dendrimer does not include the targeting peptide or the therapeutic agent. Exemplary dendrimers include poly(amidoamine) (PAMAM) and poly(propyleneamine) (POPAM).

By "core moiety" is meant a molecule with at least three functional groups arranged symmetrically or asymmetrically. One or more branch moieties, one or more targeting peptides, and one or more agents can be attached to the core moiety via the functional groups. Exemplary core moieties include propargylamine, ethylenediamine, triethanolamine, pentaerythritol, azido-propyl(alkyl)amine, hydroxyethyl(alkyl)amine, tetraphenyl methane, trimesoylchloride, diamino hexane, diaminobutane, cystamine, propylenediamine, lysine, and propyleneamine.

By "branch moiety" is meant a molecule that can be attached to a core moiety or another branch moiety and has at least four functional groups arranged symmetrically or asymmetrically (e.g., carboxyl or amine groups). Additional branch moieties or other molecules such as targeting peptides or agents can be attached via these functional groups. The branch moiety can be same as the core moiety molecule or a derivative of the core moiety or is entirely different from the core moiety.

By "surface branch" is meant the terminal branch moiety at the surface layer of the dendrimer. The surface branch has one or more functional groups (e.g., carboxyl or amine groups) to which a peptide or another molecule (e.g., a biomolecule or a linker) can be attached.

By "fragment" is meant a portion of a full-length amino acid (e.g., any sequence described herein). A fragment may retain at least one of the biological activities of the full length protein.

By "substantially identical" is meant a polypeptide with at least 35%, 40%, 50%, 55%, 60%, 65%, 70%, 75%, 85%, 90%, 95%, or even 99% identity to a reference amino acid. For polypeptides, the length of comparison sequences will generally be at least 4 (e.g., at least 5, 6, 7, 8, 9, 10, 11, 12, 13, 14, 15, 16, 17, 18, 19, 20, 25, 50, or 100) amino acids. It is to be understood herein that gaps may be found between the amino acids of sequences that are identical or similar to amino acids of the original polypeptide. The gaps may include no amino acids, one or more amino acids that are not identical or similar to the original polypeptide. Percent identity may be determined, for example, with n algorithm GAP, BESTFIT, or FASTA in the Wisconsin Genetics Software Package Release 7.0, using default gap weights.

By "blood-brain barrier" (BBB) is meant the membrane structure that protects the brain from chemicals in the blood, while still allowing essential metabolic function. The BBB is composed of endothelial cells, which are packed very tightly in brain capillaries. The BBB includes the blood-retinal barrier.

By "targeting peptide" is meant a compound or molecule such as a polypeptide that can be transported into a particular cell type (e.g., liver, lungs, kidney, spleen, or muscle) or across the BBB. The peptide may be attached to (covalently or not) or conjugated to an agent via a dendrimer and thereby may be able to transport the agent into a particular cell type or across the BBB. The targeting peptide may bind to receptors present on cancer cells or brain endothelial cells and thereby be transported into the cancer cell or across the BBB by transcytosis. The targeting peptide may be a molecule for which high levels of trans-endothelial transport may be obtained, without affecting the cell or BBB integrity. The targeting peptide may be a peptide and may be naturally occurring or produced by chemical synthesis or recombinant genetic technology.

By "therapeutic agent" is meant a molecule that is capable of being used in the treatment or prophylactic treatment of a disease or condition.

By "linkage" is meant a covalent bond or a cross-linking moiety that connects two molecules e.g., a dendrimer to targeting peptides or a dendrimer to the first or second agents. Exemplary linkages include a thioether linkage.

By "linker" is meant a molecule with one or more functional groups that can be used to connect a dendrimer to targeting peptides or a dendrimer to the first or second agents. Exemplary linkers include pyridinedisulfide, thiosulfonate, vinylsulfonate, isocyanate, NHS ester, imidoester, diazine, hydrazine, thiol, carboxylic acid, a multi-peptide linker, and acetylene.

DETAILED DESCRIPTION OF THE INVENTION

Figure 1:
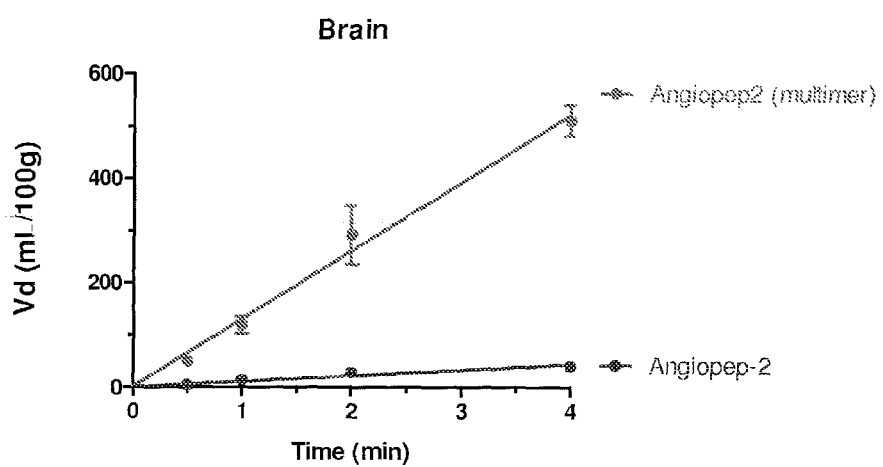
FIG. 1A is a graph showing the transport of Angiopep-2 and an Angiopep-2 multimer conjugated to PAMAM into the brain.
FIG. 1B is a bar graph showing the distribution of Angiopep-2-PAMAM multimer in the brain, capillaries, and parenchyma.
Figure 1:
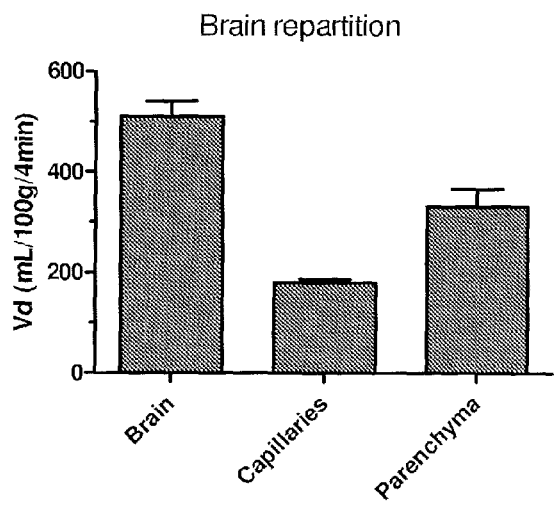
Figure 2:
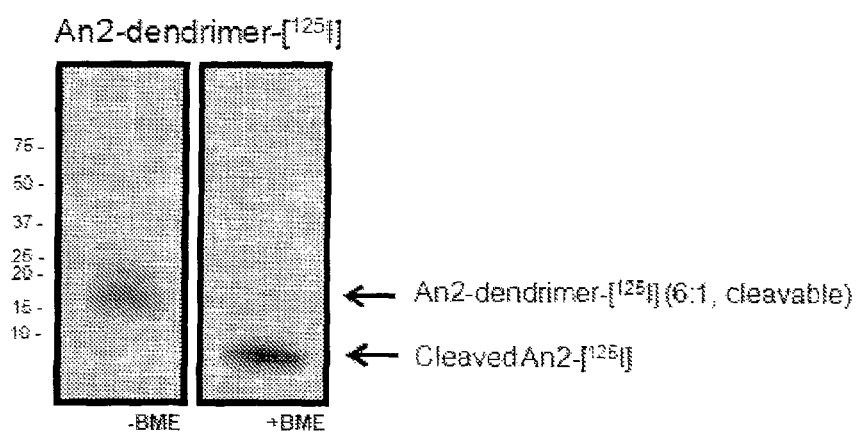
FIG. 2 is an image of a gel showing migration of a radiolabeled cleavable An2-PAMAM dendrimer conjugate before and after treatment with beta-mercaptoethanol (BME). An2 is attached to the PAMAM dendrimer via a thiol ester which is cleaved by BME to release the radiolabeled Angiopep-2 peptide.

The present invention relates to dendrimers conjugated to targeting peptides that are able to cross the BBB or are able to enter particular cell types (e.g., liver, spleen, kidney, muscle, and ovary) with enhanced efficiency. The dendrimer-targeting peptide complex, when conjugated to one or more agents (e.g., a therapeutic agent, a diagnostic agent, an imaging agent, a small molecule, a protein, and a nucleic acid), can transport the agents across the BBB or into particular cell types (e.g., cells expressing LRP-1 receptor) with increased efficiency as compared to the agent conjugated directly to a monomeric targeting peptide. One advantage of the invention is that a dendrimer provides multiple sites for attachment of targeting peptides and agents and this helps increase transport efficiency across the BBB or into specific cell types. This increased efficiency in transport may allow for lower dosages of the agents as compared either to the unconjugated agent or to the agent conjugated to a monomeric form of the targeting peptide. This may be a helpful property in case of therapeutic and diagnostic agents. In other cases, by directing the agent more efficiently to its target tissue(s), the compounds of the invention may be administered in higher dosages than either the unconjugated agent or the agent conjugated to a monomeric form of the targeting peptide, as the greater targeting efficiency can reduce side effects. Compounds including such dendrimers and their use in diagnosis and treatment of diseases are described in detail below.

Dendrimers

A dendrimer is a branched macromolecule having a core moiety with at least three functional groups. A dendrimer can have multiple branch moieties that are attached to the core moiety, and the surface branch moieties can be functionalized for attachments of various molecules (e.g., targeting peptides). One advantage of using a dendrimer is the availability of multiple surface functionalities to which multiple molecules (e.g., targeting peptides) can be conjugated.

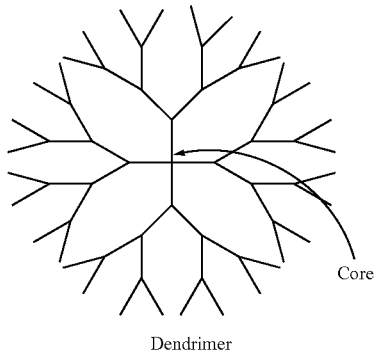 [SMILES: CC(C)C(C(C)C)C(C(C(C)C)C(C)C)C(C(C(C(C)C)C(C)C)C(C(C)C)C(C)C)(C(C(C(C)C)C(C)C)C(C(C)C)C(C)C)C(C(C(C)C)C(C)C)C(C(C)C)C(C)C]

Dendrimer

The core moiety of a dendrimer can be any known in the art, including those selected from the group consisting of propargylamine, ethylenediamine, triethanolamine, pentaerythritol, azido-propyl(alkyl)amine, hydroxyethyl(alkyl) amine, tetraphenyl methane, trimesoylchloride, diamino hexane, diaminobutane, cystamine, and propylenediamine, in case of PAMAM dendrimers. The core moiety can also be propyleneime in which case the dendrimer is poly(propyleneamine) (POPAM). Alternatively, the core moiety can be lysine, in which case the dendrimer is poly-lysine. Typically core moieties can have 1 to 12 branches (e.g., 1, 2, 3, 4, 5, 6, 7, 8, 9, 10, 11, or 12 branches). The core moieties are functionalized to form reactive groups (e.g., by reacting to methyl acrylate) for addition of the branch moieties. One or branch moieties can be attached to the core moiety via the functional groups. Targeting peptide and agents can also be attached to the core moiety with or without linkers via the functional groups.

The branch moieties form successive layers around the core moiety, and are also referred to as "generations" in the art. Each branch moiety attached to a branch of the core moiety can have 2 to 8 branches (2, 3, 4, 5, 6, 7, or 8 branches). The branch moieties can be the same as the core moieties, can be a derivative of the core moiety, or can be selected from the group consisting of propargylamine, ethylenediamine, triethanolamine, pentaerythritol, azido-propyl(alkyl)amine, hydroxyethyl(alkyl)amine, tetraphenyl methane, trimesoylchloride, diamino hexane, diaminobutane, cystamine, propylenediamine, proplyleneamine, and lysine.

A dendrimer can have 2 to 10 layers (2, 3, 4, 5, 6, 7, 8, 9, or 10 layers) of branches, terminating in the outer most branch moieties, which are also referred to as surface branches. The surface branches can be functionalized for attachment of multiple chemical entities (e.g., targeting peptides). The number of surface branches is computed by the formula, $n=p(b)^l$, where n=the number of surface branches, b=the number of branches each branch moiety has, and l=the number of successive layers of branches of the dendrimer. Since a dendrimer will be attached to multiple targeting peptides and one or more agents, it is desirable that the dendrimer size be in a range to accommodate attachment of these cargoes. For example, a desirable dendrimer molecular weight is less than 500 kilodaltons (e.g., 10, 50, 100, 200, 300, or 500 kilodaltons).

PAMAM is perhaps the most well known dendrimer. The core of PAMAM is a diamine (commonly ethylenediamine), which is reacted with methyl acrylate, and then another ethylenediamine to make the generation-0 (G-0) PAMAM. Successive reactions create higher generations, which tend to have different properties. Lower generations are generally flexible molecules with no appreciable inner regions, while medium sized (G-3 or G-4) have internal space that is essentially separated from the outer shell of the dendrimer. Very large (G-7 and greater) dendrimers are generally more like solid particles with very dense surfaces due to the structure of their outer shell.

Synthesis of Dendrimers

Methods for synthesizing dendrimers are well known in the art, as described herein, and the branched portion of the dendrimer (the $X_{core}$ and $X_{branch}$ portions) can also be purchased from a commercial supplier with varying numbers of layers of branches. There are two commonly used methods of dendrimer synthesis: divergent synthesis and convergent synthesis. In divergent synthesis (shown below), the dendrimer is assembled from a multifunctional core, which is extended outward by a series of reactions, commonly a Michael reaction. Each step of the reaction is generally driven to full completion to prevent mistakes in the dendrimer, which can cause trailing generations (some branches are shorter than the others). Such impurities can impact the functionality and symmetry of the dendrimer, but are extremely difficult to purify out because the relative size difference between perfect and imperfect dendrimers is very small.

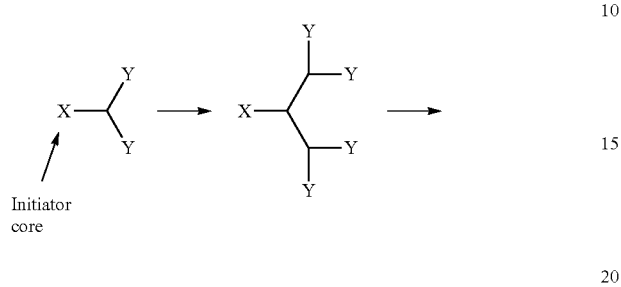

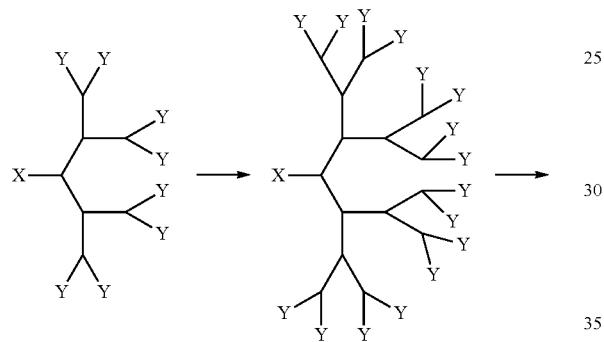

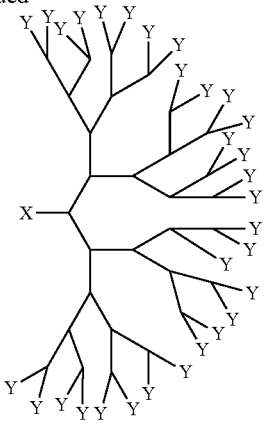

In convergent synthesis (shown below), dendrimers are built from small molecules that end up at the surface of the sphere, and reactions proceed inward, such that the inward most molecules that are attached last are attached to a core. This method makes it much easier to remove impurities and shorter branches along the way, so that the final dendrimer is more monodisperse. However dendrimers made this way are not as large as those made by divergent methods because crowding due to steric effects along the core is limiting.

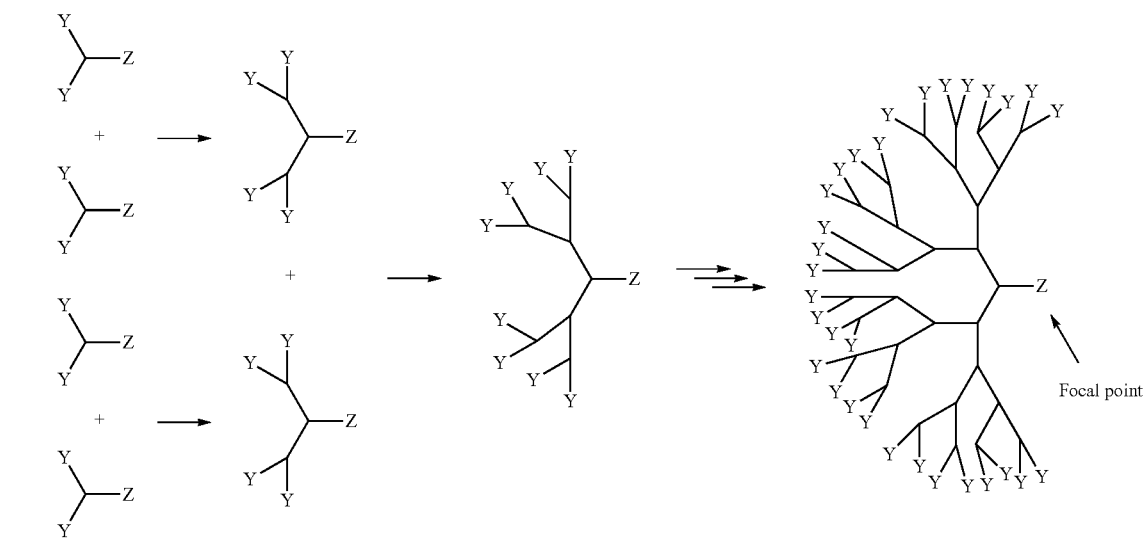

Alternatively, dendrimers can also be synthesized by click chemistry, employing Diels-Alder reactions, thiol-yne reactions, and azide-alkyne reactions.

A dendrimer can be synthesized to have different functionalities in the core and the branches to control properties such as solubility, thermal stability, and attachment of compounds for particular applications. Synthetic processes can also precisely control the size, number of branches, numbers of layers of branches from the core, and the functionalities of the terminal branches for attachment of various reactive groups.

An exemplary synthesis of a dendrimer is shown in example 1, where a propargylamine core is reacted first with methyl acrylate followed by ethylenediamine to attach branches. Successive reactions of methyl acrylate and ethylenediamine result in attachment of further layers of ethylenediamine branches.

Conjugation of Targeting Peptides to Surface Branches of Dendrimers

The surface branches of dendrimers can be functionalized for conjugation of targeting peptides derivatized with appropriate reactive groups. For example, the surface branches can be reacted with compounds, e.g., N-succinimidyl 3-(2-pyridyldithio) (SPDP) to generate a dendrimer-pyridyl-disulfide intermediate that can be then be reacted with a targeting peptides containing a cysteine residue. Alternatively, the surface branches of dendrimers can be reacted with N-succinimidyl S-acetylthioacetate (SATA) to form a dendrimer-sulfhydryl intermediate that can be reacted with a maleimide derivatized targeting peptides. SATA is reactive towards amines and adds protected sulfhydryls groups), and BMOE (bis-maleimidoethane). Linkers can be used to conjugate targeting peptides to the surface functionalities of dendrimers and are described below.

Dendrimer Configurations

Each part of a given conjugate, including the cytotoxic agent, linker, and polypeptide, can be selected independently. That is, insofar as the interacting chemical substituents are compatible with one another, any of the linkers described herein can be used to conjugate any of the polypeptides and cytotoxic agents described. The conjugates can then be used to deliver the cytotoxic agents to a patient for treatment of a CNS cancer or other cancer. With the inclusion of a detectable marker, the present conjugates can also be used as imaging agents, providing the means to map the distribution of the targets to which the cytotoxic agents bind and/or the receptors for which the polypeptides have affinity.

While specific configurations are discussed further below, we note that a given protein conjugate can include one or more polypeptide moieties relative to each cytotoxic agent (e.g., 1-2 polypeptides relative to each cytotoxic agent within the conjugate) and one or more cytotoxic agents relative to the polypeptide (e.g., 1-3 cytotoxic agents per polypeptide). As noted, a given protein conjugate is likely to include a single cytotoxic agent, but it may include two or more (e.g., 2, 3, or 4) that are identical to one another or different from one another. Where different, the cytotoxic agents may specifically bind the same target or different targets. The component parts of the present conjugates can be configured in a variety of ways. Overall, the conjugate can assume an essentially linear form with a cytotoxic agent being linked to at least one polypeptide, which is in turn linked to at least one cytotoxic agent. Alternatively, the conjugate can have a branched configuration as seen in dendrimers, with one or more branches extending at some point from cytotoxic agent (D). Where the present conjugates include a branched portion, we may refer to the conjugate as a "dendrimer conjugate" with the understanding that the inclusion of the cytotoxic agent does not allow for a fully symmetrical dendrimeric form. A dendrimeric conjugate can be structured as in Formula I:

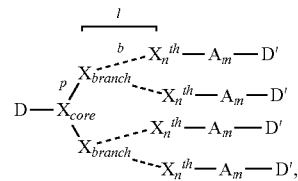

D is a cytotoxic agent that is linked to the core moiety of the dendrimer conjugate ($X_{core}$) either directly (e.g., by way of a bond between the cytotoxic agent and $X_{core}$) or indirectly (e.g., by way of a bifunctional linker that joins the cytotoxic agent moiety to $X_{core}$). As $X_{core}$ and $X_{branch}$ both join one part of a conjugate to another, we may also refer to either moiety more simply as a "linker". The complexity of the core moiety can vary, with the number of available extension points, p, varying from 2 to 6, inclusive. Each extension point p can terminate in (and be joined to) a branch moiety, $X_{branch}$, that, like $X_{core}$, varies in complexity with each $X_{branch}$ having from 2 to 4 branches, b. $X_n^{th}$ is one of n surface branches, and l, an integer from 1 to 5, inclusive, is the number of successive layers of $X_{branch}$ moieties. Where l is 1, each $X_{branch}$ is attached to $X_{core}$. Where l is more than 1, each $X_{branch}$ distal to the first $X_{branch}$ is attached to another $X_{branch}$. With regard to the surface branches, $X_n^{th}$ is one of n surface branches of the dendrimer. $n=p(b^l)$, and n is typically $\leq 512$ (e.g., $\leq 500$, $\leq 400$, $\leq 300$, $\leq 200$, $\leq 50$, $\leq 10$, or $\leq 8$ branches). To illustrate: where there are two extension points p, where l is 1, and where there are two branches b from each $X_{branch}$, $X_n^{th}$ is 4; where there are three extension points p, where l is 1, and where there are three branches b from each $X_{branch}$, $X_n^{th}$ is 9; and so forth. $A_m$ is a polypeptide as described herein that is attached to a surface branch $X_n^{th}$. The number of polypeptides $A_m$ is less than or equal to the number of surface branches, as each surface branch can be joined to a polypeptide, and some surface branches can be either free of any additional components or joined directly to a cytotoxic agent D' (i.e., at some surface branches, the polypeptide represented by $A_m$ is absent). The cytotoxic agent D' is attached to one or more $A_m$ or, as noted, may replace one or more (but not all) $A_m$, attaching directly to one or more $X_n^{th}$. The number of D' in the dendrimer conjugate can be up to three times the number of polypeptides, as up to three cytotoxic agents can be joined to each polypeptide. The molecular weight of the dendrimer, excluding D, D' and $A_m$, is $\leq 500$ kilodalton (e.g., $\leq 500$, $\leq 400$, $\leq 300$, $\leq 200$, $\leq 100$, $\leq 50$, or $\leq 20$ kilodaltons).

The linkers employed as $X_{core}$ and $X_{branch}$ can be the same or different, and one can make less complex dendrimer conjugates by employing a bifunctional linker as either $X_{core}$ or $X_{branch}$. Where $X_{core}$ is a bifunctional linker, p is 1 and the complexity that would have been generated by multiple extensions from $X_{core}$ is missing. This arrangement is illustrated in the Formula below, with the remainder of the conjugate as described above.

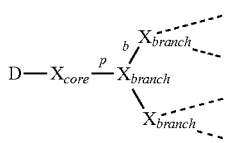

In a variant of this configuration, $X_{core}$ is absent, in which case the cytotoxic agent is joined directly to an $X_{branch}$. Where $X_{branch}$, rather than $X_{core}$, is a bifunctional linker, b is 1, and the complexity that would have been generated by multiple extensions from $X_{branch}$ is missing. This arrangement is illustrated in the Formula below, with the remainder of the conjugate as described above.

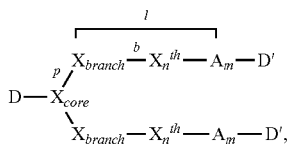

One advantage of the dendrimeric conjugate is the inclusion of multiple surface functionalities to which multiple polypeptides and/or cytotoxins can be conjugated. The ability to alter the complexity of the dendrimeric conjugate allows one to accommodate the various component parts of the protein conjugate. Where $X_{core}$ and $X_{branch}$ are both bifunctional linkers, the conjugate is linear, not dendrimeric.

Linkers

The targeting peptides may be conjugated through a variety of linking groups (linkers), e.g., sulfhydryl groups, amino groups (amines), or any appropriate reactive group. The linker can be a covalent bond. Homobifunctional and hetero-bifunctional cross-linkers (conjugation agents) are available from many commercial sources. Sites available for cross-linking may be found on the targeting peptides. The linker group may comprise a flexible arm, e.g., 2, 3, 4, 5, 6, 7, 8, 9, 10, 11, 12, 13, 14, or 15 carbon atoms. Exemplary linkers include pyridinedisulfide, thiosulfonate, vinylsulfonate, isocyanate, imidoester, diazine, hydrazine, thiol, carboxylic acid, multi-peptide linkers, and acetylene. Alternatively other linkers than can be used include BS³ [Bis (sulfosuccinimidyl)suberate](which is a homobifunctional N-hydroxysuccinimide ester that targets accessible primary amines), NHS/EDC (N-hydroxysuccinimide and 1-ethyl-3-(3-dimethylaminopropyl)carbodiimide (NHS/EDC allows for the conjugation of primary amine groups with carboxyl groups), sulfo-EMCS ([N-ϵ-maleimidocaproic acid]hydrazide (sulfo-EMCS are heterobifunctional reactive groups that are reactive toward sulfhydryl and amino groups), hydrazide (most proteins contain exposed carbohydrates and hydrazide is a useful reagent for linking carboxyl groups to primary amines).

To form covalent bonds, one can use as a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxysulfosuccinimide (sulfo-NHS), maleimide-benzoyl-succinimide (MBS), gamma-maleimido-butyryloxy succinimide ester (GMBS), maleimido propionic acid (MPA), maleimido hexanoic acid (MHA), and maleimido undecanoic acid (MUA).

Primary amines are the principal targets for NHS esters. Accessible α-amine groups present on the N-termini of proteins and the ϵ-amine of lysine react with NHS esters. Thus, compounds of the invention can include a linker having a NHS ester conjugated to an N-terminal amino of a peptide or to an ϵ-amine of lysine. An amide bond is formed when the NHS ester conjugation reaction reacts with primary amines releasing N-hydroxysuccinimide. These succinimide containing reactive groups are herein referred to as succinimidyl groups. In certain embodiments of the invention, the functional group on the protein will be a thiol group and the chemically reactive group will be a maleimido-containing group such as gamma-maleimide-butrylamide (GMBA or MPA). Such maleimide containing groups are referred to herein as maleido groups.

The maleimido group is most selective for sulfhydryl groups on peptides when the pH of the reaction mixture is 6.5-7.4. At pH 7.0, the rate of reaction of maleimido groups with sulfhydryls (e.g., thiol groups on proteins such as serum albumin or IgG) is 1000-fold faster than with amines. Thus, a stable thioether linkage between the maleimido group and the sulfhydryl can be formed. Accordingly, a compound of the invention can include a linker having a maleimido group conjugated to a sulfhydryl group of a targeting peptide.

Amine-to-amine linkers include NHS esters and imidoesters. Exemplary NHS esters are DSG (disuccinimidyl glutarate), DSS (disuccinimidyl suberate), BS³ (bis[sulfosuccinimidyl] suberate), TSAT (tris-succinimidyl aminotriacetate), variants of bis-succinimide ester-activated compounds that include a polyethylene glycol spacer such as BS(PEG)$_n$ where n is 1-20 (e.g., BS(PEG)$_5$ and BS(PEG)$_9$), DSP (Dithiobis[succinimidyl propionate]), DTSSP (3,3'-dithiobis[sulfosuccinimidylpropionate]), DST (disuccinimidyl tartarate), BSOCOES (bis[2-(succinimidooxycarbonyloxy) ethyl]sulfone), EGS (ethylene glycol bis[succinimidylsuccinate]), and sulfo-EGS (ethylene glycol bis[sulfosuccinimidylsuccinate]). Imidoesters include DMA (dimethyl adipimidate.2 HCl), DMP (dimethyl pimelimidate.2 HCl), DMS (dimethyl suberimidate.2 HCl), and DTBP (dimethyl 3,3'-dithiobispropionimidate.2 HCl). Other amine-to-amine linkers include DFDNB (1,5-difluoro-2,4-dinitrobenzene) and THPP (β-[tris(hydroxymethyl) phosphino]propionic acid (betaine)).

The linker may be a sulfhydryl-to-sulfhydry linker. Such linkers include maleimides and pyridyldithiols. Exemplary maleimides include BMOE (bis-maleimidoethane), BMB (1,4-bismaleimidobutane), BMH (bismaleimidohexane), TMEA (tris[2-maleimidoethyl]amine), BM(PEG)2 1,8-bis-maleimidodiethyleneglycol) or BM(PEG)$_n$, where n is 1 to 20 (e.g., 2 or 3), BMDB (1,4 bismaleimidyl-2,3-dihydroxybutane), and DTME (dithio-bismaleimidoethane). Exemplary pyridyldithiols include DPDPB (1,4-di-[3'-(2'-pyridyldithio)-propionamido]butane). Other sulfhydryl linkers include HBVS (1,6-hexane-bis-vinylsulfone).

The linker may be an amine-to-sulfhydryl linker, which includes NHS ester/maliemide compounds. Examples of these compounds are AMAS (N-(α-maleimidoacetoxy)succinimide ester), BMPS (N-[β-maleimidopropyloxy]succinimide ester), GMBS (N-[γ-maleimidobutyryloxy]succinimide ester), sulfo-GMBS (N-[γ-maleimidobutyryloxy]sulfosuccinimide ester), MBS (m-maleimidobenzoyl-N-hydroxysuccinimide ester), sulfo-MBS (m-maleimidobenzoyl-N-hydroxysulfosuccinimide ester), SMCC (succinimidyl 4-[N-maleimidomethyl]cyclohexane-1-carboxylate), sulfo-SMCC (Sulfosuccinimidyl 4-[N-maleimidomethyl]cyclohexane-1-carboxylate), EMCS ([N-ϵ-maleimidocaproyloxy]succinimide ester), Sulfo-EMCS ([N-

ε-maleimidocaproyloxy]sulfosuccinimide ester), SMPB (succinimidyl 4-[p-maleimidophenyl]butyrate), sulfo-SMPB (sulfosuccinimidyl 4-[p-maleimidophenyl]butyrate), SMPH (succinimidyl-6-[β-maleimidopropionamido] hexanoate), LC-SMCC (succinimidyl-4-[N-maleimidomethyl]cyclohexane-1-carboxy-[6-amidocaproate]), sulfo-KMUS (N-[κ-maleimidoundecanoyloxy]sulfosuccinimide ester), SM(PEG)$_n$ (succinimidyl-([N-maleimidopropionamido-polyethyleneglycol) ester), where n is 1 to 30 (e.g., 2, 4, 6, 8, 12, or 24), SPDP (N-succinimidyl 3-(2-pyridyldithio)-propionate), LC-SPDP (succinimidyl 6-(3-[2-pyridyldithio]-propionamido)hexanoate), sulfo-LC-SPDP (sulfosuccinimidyl 6-(3'-[2-pyridyldithio]-propionamido) hexanoate), SMPT (4-succinimidyloxycarbonyl-α-methyl-α-[2-pyridyldithio]toluene), Sulfo-LC-SMPT (4-sulfosuccinimidyl-6-[α-methyl-α-(2-pyridyldithio)toluamido]hexanoate), SIA (N-succinimidyl iodoacetate), SBAP (succinimidyl 3-[bromoacetamido]propionate), SIAB (N-succinimidyl[4-iodoacetyl]aminobenzoate), and sulfo-SIAB (N-sulfosuccinimidyl[4-iodoacetyl]aminobenzoate).

The linker can be an amino-to-nonselective linker. Examples of such linkers include NHS ester/aryl azide and NHS ester/diazirine linkers. NHS ester/aryl azide linkers include NHS-ASA (N-hydroxysuccinimidyl-4-azidosalicylic acid), ANB-NOS (N-5-azido-2-nitrobenzoyloxysuccinimide), sulfo-HSAB (N-hydroxysulfosuccinimidyl-4-azidobenzoate), sulfo-NHS-LC-ASA (sulfosuccinimidyl[4-azidosalicylamido]hexanoate), SANPAH (N-succinimidyl-6-(4'-azido-2'-nitrophenylamino)hexanoate), sulfo-SANPAH (N-sulfosuccinimidyl-6-(4'-azido-2'-nitrophenylamino)hexanoate), sulfo-SFAD (sulfosuccinimidyl-(perfluoroazidobenzamido)-ethyl-1,3'-dithiopropionate), sulfo-SAND (sulfosuccinimidyl-2-(m-azido-o-nitrobenzamido)-ethyl-1,3'-proprionate), and sulfo-SAED (sulfosuccinimidyl 2-[7-amino-4-methylcoumarin-3-acetamido]ethyl-1,3'-dithiopropionate). NHS ester/diazirine linkers include SDA (succinimidyl 4,4'-azipentanoate), LC-SDA (succinimidyl 6-(4,4'-azipentanamido)hexanoate), SDAD (succinimidyl 2-([4,4'-azipentanamido]ethyl)-1,3'-dithiopropionate), sulfo-SDA (sulfosuccinimidyl 4,4'-azipentanoate), sulfo-LC-SDA (sulfosuccinimidyl 6-(4,4'-azipentanamido)hexanoate), and sulfo-SDAD (sulfosuccinimidyl 2-([4,4'-azipentanamido]ethyl)-1,3'-dithiopropionate).

Exemplary amine-to-carboxyl linkers include carbodiimide compounds (e.g., DCC (N,N-dicyclohexylcarbodiimide) and EDC (1-ethyl-3-[3-dimethylaminopropyl]carbodiimide)). Exemplary sulfhydryl-to-nonselective linkers include pyridyldithiol/aryl azide compounds (e.g., APDP ((N-[4-(p-azidosalicylamido)butyl]-3'-(2'-pyridyldithio)propionamide)). Exemplary sulfhydryl-to-carbohydrate linkers include maleimide/hydrazide compounds (e.g., BMPH (N-[β-maleimidopropionic acid]hydrazide), EMCH ([N-ε-maleimidocaproic acid]hydrazide), MPBH 4-(4-N-maleimidophenyl)butyric acid hydrazide), and KMUH (N-[κ-maleimidoundecanoic acid]hydrazide)) and pyridyldithiol/hydrazide compounds (e.g., PDPH (3-(2-pyridyldithio) propionyl hydrazide)). Exemplary carbohydrate-to-nonselective linkers include hydrazide/aryl azide compounds (e.g., ABH (p-azidobenzoyl hydrazide)). Exemplary hydroxyl-to-sulfhydryl linkers include isocyanate/maleimide compounds (e.g., (N-[p-maleimidophenyl]isocyanate)). Exemplary amine-to-DNA linkers include NHS ester/psoralen compounds (e.g., SPB (succinimidyl-[4-(psoralen-8-yloxy)]-butyrate)).

The linker can also be a trifunctional, tetrafunctional, or greater linking agent. Exemplary trifunctional linkers include TMEA, THPP, TSAT, LC-TSAT (tris-succinimidyl (6-aminocaproyl)aminotriacetate), tris-succinimidyl-1,3,5-benzenetricarboxylate, MDSI (maleimido-3,5-disuccinimidyl isophthalate), SDMB (succinimidyl-3,5-dimaleimidophenyl benzoate, Mal-4 (tetrakis-(3-maleimidopropyl) pentaerythritol, NHS-4 (tetrakis-(N-succinimidylcarboxypropyl)pentaerythritol)).

TMEA has the structure:

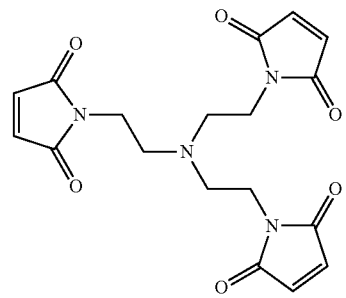 [SMILES: O=C1C=CC(=O)N1CCN(CCN1C(=O)C=CC1=O)CCN1C(=O)C=CC1=O]

TMEA, through its maleimide groups, can react with sulfhydryl groups (e.g., through cysteine amino acid side chains).

THPP has the structure:

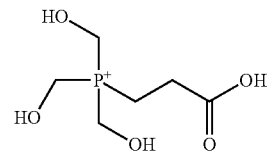

The hydroxyl groups and carboxy group of THPP can react with primary or secondary amines.

Linkers are also described in U.S. Pat. No. 4,680,338 having the formula Y=C=N-Q-A-C(O)—Z, where Q is a homoaromatic or heteroaromatic ring system; A is a single bond or an unsubstituted or substituted divalent $C_{1-30}$ bridging group, Y is O or S; and Z is Cl, Br, I, $N_3$, N-succinimidyloxy, imidazolyl, 1-benzotriazolyloxy, OAr where Ar is an electron-deficient activating aryl group, or OC(O)R where R is -A-Q-N=C=Y or $C_4$-20 tertiary-alkyl.

Linkers are also described in U.S. Pat. No. 5,306,809, which describes linkers having the formula

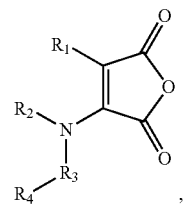

where $R_1$ is H, $C_1$-6 alkyl, $C_{2-6}$ alkenyl, $C_{6-12}$ aryl or aralkyl or these coupled with a divalent organic —O—, —S—, or

where R' is $C_{1-6}$ alkyl, linking moiety; $R_2$ is H, $C_{1-12}$ alkyl, $C_{6-12}$ aryl, or $C_{6-12}$ aralkyl, $R_3$ is

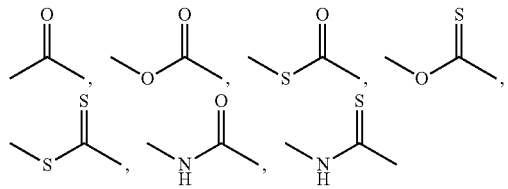

or another chemical structure which is able to delocalize the lone pair electrons of the adjacent nitrogen and $R_4$ is a pendant reactive group capable of linking $R_3$ to a peptide vector or to an agent.

The linker may include at least one amino acid (e.g., a peptide of at least 2, 3, 4, 5, 6, 7, 10, 15, 20, 25, 40, or 50 amino acids). For example, the linker is a single amino acid (e.g., any naturally occurring amino acid such as Cys). A glycine-rich peptide such as a peptide having the sequence [Gly-ly-Gly-Gly-Ser]$_n$ where n is 1, 2, 3, 4, 5 or 6, as described in U.S. Pat. No. 7,271,149, or a serine-rich peptide linker is used, as described in U.S. Pat. No. 5,525,491, can be used. Serine rich peptide linkers include those of the formula [X-X-X-X-Gly]$_y$, where up to two of the X are Thr, and the remaining X are Ser, and y is 1 to 5 (e.g., Ser-Ser-Ser-Ser-Gly, where y is greater than 1).

In some cases, the linker is a single amino acid (e.g., any amino acid, such as Gly or Cys). In some cases the linkers can be multi-amino acid or multi-peptide linkers. Amino acid linkers and multi-peptide linkers can be selected for flexibility (e.g., flexible or rigid) or may be selected on the basis of charge (e.g., positive, negative, or neutral). Flexible linkers typically include those with Gly resides (e.g., [Gly-Gly-Gly-Gly-Ser]$_n$ where n is 1, 2, 3, 4, 5 or 6). Other linkers include rigid linkers (e.g., PAPAP and (PT)$_n$P, where n is 2, 3, 4, 5, 6, or 7) and α-helical linkers (e.g., A(EAAAK)$_n$A, where n is 1, 2, 3, 4, or 5).

Examples of suitable amino acid linkers are succinic acid, Lys, Glu, and Asp, or a dipeptide such as Gly-Lys. When the linker is succinic acid, one carboxyl group thereof may form an amide bond with an amino group of the amino acid residue, and the other carboxyl group thereof may, for example, form an amide bond with an amino group of the peptide or substituent. When the linker is Lys, Glu, or Asp, the carboxyl group thereof may form an amide bond with an amino group of the amino acid residue, and the amino group thereof may, for example, form an amide bond with a carboxyl group of the substituent. When Lys is used as the linker, a further linker may be inserted between the ε-amino group of Lys and the substituent. The further linker may be succinic acid, which can form an amide bond with the ε-amino group of Lys and with an amino group present in the substituent. In one embodiment, the further linker is Glu or Asp (e.g., which forms an amide bond with the ε-amino group of Lys and another amide bond with a carboxyl group present in the substituent), that is, the substituent is a $N^\epsilon$-acylated lysine residue.

The peptide linker can also be a branched polypeptide. Exemplary branched peptide linkers are described in U.S. Pat. No. 6,759,509. Such linkers include those of the formula:

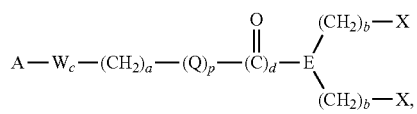

where A is a thiol acceptor; W is a bridging moiety; c is an integer of 0 to 1; a is an integer of 2 to 12; Q is O, NH, or N-lower alkyl; p is an integer of 0 or 1; d is an integer of 0 or 1; E is a polyvalent atom; each b is an integer of 1 to 10; each X is of the formula:

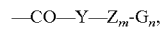

where Y is two amino acid residues in the L form; Z is one or two amino acid residues; m is an integer of 0 or 1; G is a self-immolative spacer; and n is a integer of 0 or 1; provided that when n is 0 then —Y—$Z_m$ is Ala-Leu-Ala-Leu or Gly-Phe-Leu-Gly; or each X is of the formula:

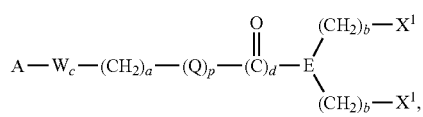

where each $X^1$ is of the formula —CO—Y—$Z_m$-$G_n$; and where Y, Z, Q, E, G, m, d, p, a, b, and n are as defined above; or each $X^1$ is of the formula:

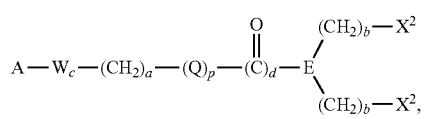

where each $X^2$ is of the formula —CO—Y—$Z_m$-$G_n$; and where Y, Z, G, Q, E, m, d, p, a, b, and n are as defined above; or each $X^2$ is of the formula:

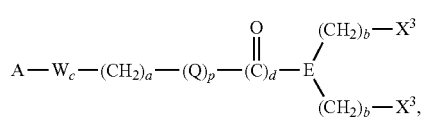

where each $X^3$ is of the formula —CO—Y—$Z_m$-$G_n$; and wherein Y, Z, G, Q, E, m, d, p, a, b, and n are as defined above; or each $X^3$ is of the formula

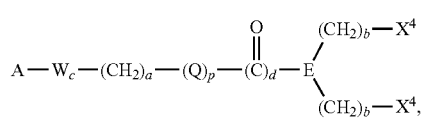

where each $X^4$ is of the formula —CO—Y—$Z_m$-$G_n$; and where Y, Z, G, Q, E, m, d, p, a, b, and n are as defined above.

The branched linker may employ an intermediate self-immolative spacer moiety (G), which covalently links together the agent or peptide vector and the branched peptide linker. A self-immolative spacer can be a bifunctional chemical moiety capable of covalently linking together two chemical moieties and releasing one of said spaced chemical moieties from the tripartate molecule by means of enzymatic cleavage (e.g., any appropriate linker described herein. In certain embodiments, G is a self-immolative spacer moiety which spaces and covalently links together the agent or peptide vector and the peptide linker, where the spacer is linked to the peptide vector or agent via the T moiety (as used in the following formulas "T" represents a nucleophilic atom which is already contained in the agent or peptide vector), and which may be represented by

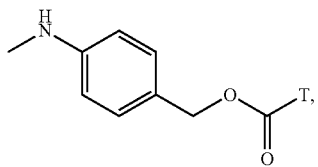

where T is O, N or S; —HN—R$^1$—COT, where T is O, N or S, and R$^1$ is C$_{1-5}$ alkyl;

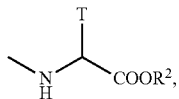

where T is O, N, or S, and R$^2$ is H or C$_{1-5}$ alkyl;

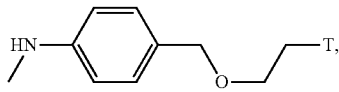

where T is O, N or S; or

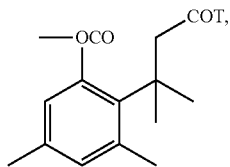

where T is O, N, or S. Preferred Gs include PABC (p-aminobenzyl-carbamoyl), GABA (γ-aminobutyric acid), α,α-dimethyl GABA, and β,β-dimethyl GABA.

In the branched linker, the thiol acceptor "A" is linked to a peptide vector or agent by a sulfur atom derived from the peptide vector or agent. The thiol acceptor can be, for example, an α-substituted acetyl group. Such a group has the formula:

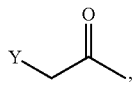

where Y is a leaving group such as Cl, Br, I, mesylate, tosylate, and the like. If the thiol acceptor is an alpha-substituted acetyl group, the thiol adduct after linkage to the ligand forms the bond —S—CH$_2$—. Preferably, the thiol acceptor is a Michael Addition acceptor. A representative Michael Addition acceptor of this invention has the formula

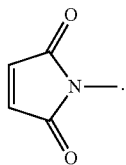

After linkage the thiol group of the ligand, the Michael Addition acceptor becomes a Michael Addition adduct, e.g.,

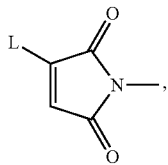

where L is an agent or peptide vector.

The bridging group "W" is a bifunctional chemical moiety capable of covalently linking together two spaced chemical moieties into a stable tripartate molecule. Examples of bridging groups are described in S. S. Wong, *Chemistry of Protein Conjugation and Crosslinking*. CRC Press, Florida, (1991); and G. E. Means and R. E. Feeney, *Bioconiugate Chemistry*, vol. 1, pp. 2-12, (1990), the disclosures of which are incorporated herein by reference. W can covalently link the thiol acceptor to a keto moiety. An exemplary a bridging group has the formula —(CH$_2$)$_f$—(Z)$_g$—(CH$_2$)$_h$—, where f is 0 to 10; h is 0 to 10; g is 0 or 1, provided that when g is 0, then f+h is 1 to 10; Z is S, O, NH, SO$_2$, phenyl, naphthyl, a polyethylene glycol, a cycloaliphatic hydrocarbon ring containing 3 to 10 carbon atoms, or a heteroaromatic hydrocarbon ring containing 3 to 6 carbon atoms and 1 or 2 heteroatoms selected from O, N, or S. Preferred cycloaliphatic moieties include cyclopropyl, cyclobutyl, cyclopentyl, cyclohexyl, and the like. Preferred heteroaromatic moieties include pyridyl, polyethylene glycol (1-20 repeating units), furanyl, pyranyl, pyrimidinyl, pyrazinyl, pyridazinyl, oxazinyl, pyrrolyl, thiazolyl, morpholinyl, and the like. In the bridging group, it is preferred that when g is 0, f+h is an integer of 2 to 6 (e.g., 2 to 4 such as 2). When g is 1, it is preferred that f is 0, 1 or 2; and that h is 0, 1 or 2. Preferred bridging groups coupled to thiol acceptors are shown in the Pierce Catalog, pp. E-12, E-13, E-14, E-15, E-16, and E-17 (1992).

The linker between a targeting peptide and the dendrimer can be a cleavable linker (e.g., a thiol ester linker) or a non-cleavable linker.

Targeting Peptides

The targeting peptide of the invention can be attached to the dendrimer to form a dendrimer-targeting peptide complex. The targeting peptide may be a polypeptide substantially identical to any of the sequences in Table 1, or a fragment thereof. The targeting peptide may have a sequence of Angiopep-1 (SEQ ID NO:67), Angiopep-2 (SEQ ID NO:97), Angiopep-3 (SEQ ID NO:107), Angiopep-4a (SEQ ID NO:108), Angiopep-4b (SEQ ID NO:109), Angiopep-5 (SEQ ID NO:110), Angiopep-6 (SEQ ID NO:111), Angiopep-7 (SEQ ID NO:112) or reversed Angiopep-2 (SEQ ID NO:117)). The targeting peptide or compound of the invention may be efficiently transported into a particular cell type (e.g., any one, two, three, four, or five of liver, lung, kidney, spleen, and muscle) or may cross the mammalian BBB efficiently (e.g., Angiopep-1, -2, -3, -4a, -4b, -5, and -6). The targeting peptide or compound will be able to enter a particular cell type (e.g., any one, two, three, four, or five of liver, lung, kidney, spleen, and muscle) but does not cross the BBB efficiently (e.g., a conjugate including Angiopep-7). The targeting peptide may be of any length, for example, at least 6, 7, 8, 9, 10, 11, 12, 13, 14, 15, 16, 17, 18, 19, 20, 21, 25, 35, 50, 75, 100, 200, or 500 amino acids, or any range between these numbers. The targeting peptide is 10 to 50 amino acids in length and may be produced by recombinant genetic technology or chemical synthesis.

TABLE 1

Exemplary Targeting peptides

| SEQ ID NO: | Sequence |
| --- | --- |
| 1 | T F V Y G G C R A K R N N F K S A E D |
| 2 | T F Q Y G G C M G N G N N F V T E K E |
| 3 | P F F Y G G C G G N R N N F D T E E Y |
| 4 | S F Y Y G G C L G N K N N Y L R E E E |
| 5 | T F F Y G G C R A K R N N F K R A K Y |
| 6 | T F F Y G G C R G K R N N F K R A K Y |
| 7 | T F F Y G G C R A K K N N Y K R A K Y |
| 8 | T F F Y G G C R G K K N N F K R A K Y |
| 9 | T F Q Y G G C R A K R N N F K R A K Y |
| 10 | T F Q Y G G C R G K K N N F K R A K Y |
| 11 | T F F Y G G C L G K R N N F K R A K Y |
| 12 | T F F Y G G S L G K R N N F K R A K Y |
| 13 | P F F Y G G C G G K K N N F K R A K Y |
| 14 | T F F Y G G C R G K G N N Y K R A K Y |
| 15 | P F F Y G G C R G K R N N F L R A K Y |
| 16 | T F F Y G G C R G K R N N F K R E K Y |
| 17 | P F F Y G G C R A K K N N F K R A K E |
| 18 | T F F Y G G C R G K R N N F K R A K D |
| 19 | T F F Y G G TABLE 1-continued Exemplary Targeting peptides

| SEQ ID NO: | Sequence |
|---|---|
| 35 | P F F Y G G C G G K G N N Y V T A K Y |
| 36 | T F F Y G G C L G K G N N F L T A K Y |
| 37 | S F F Y G G C L G N K N N F L T A K Y |
| 38 | T F F Y G G C G G N K N N F V R E K Y |
| 39 | T F F Y G G C M G N K N N F V R E K Y |
| 40 | T F F Y G G S M G N K N N F V R E K Y |
| 41 | P F F Y G G C L G N R N N Y V R E K Y |
| 42 | T F F Y G G C L G N R N N F V R E K Y |
| 43 | T F F Y G G C L G N K N N Y V R E K Y |
| 44 | T F F Y G G C G G N G N N F L T A K Y |
| 45 | T F F Y G G C R G N R N N F L T A E Y |
| 46 | T F F Y G G C R G N G N N F K S A E Y |
| 47 | P F F Y G G C L G N K N N F K T A E Y |
| 48 | T F F Y G G C R G N R N N F K T E E Y |
| 49 | T F F Y G G C R G K R N N F K T E E D |
| 50 | P F F Y G G C G G N G N N F V R E K Y |
| 51 | S F F Y G G C M G N G N N F V R E K Y |
| 52 | P F F Y G G C G G N G N N F L R E K Y |
| 53 | T F F Y G G C L G N G N N F V R E K Y |
| 54 | S F F Y G G C L G N G N N Y L R E K Y |
| 55 | T F F Y G G S L G N G N N F V R E K Y |
| 56 | T F F Y G G C R G N G N N F V T A E Y |
| 57 | T F F Y G G C L G K G N N F V S A E Y |
| 58 | T F F Y G G C L G N R N N F D R A E Y |
| 59 | T F F Y G G C L G N R N N F L R E E Y |
| 60 | T F F Y G G C L G N K N N Y L R E E Y |
| 61 | P F F Y G G C G G N R N N Y L R E E Y |
| 62 | P F F Y G G S G G N R N N Y L R E E Y |
| 63 | M R P D F C L E P P Y T G P C V A R I |
| 64 | A R I I R Y F Y N A K A G L C Q T F V Y G |
| 65 | Y G G C R A K R N N Y K S A E D C M R T C G |
| 66 | P D F C L E P P Y T G P C V A R I I R Y F Y |
| 67 | T F F Y G G C R G K R N N F K T E E Y |
| 68 | K F F Y G G C R G K R N N F K T E E Y |
| 69 | T F Y Y G G C R G K R N N Y K T E E Y |
| 70 | T F F Y G G S R G K R N N F K T E E Y |
| 71 | C T F F Y G C C R G K R N N F K T E E Y |
| 72 | T F F Y G G C R G K R N N F K T E E Y C |

TABLE 1-continued

Exemplary Targeting peptides

| SEQ ID NO: | |
|---|---|
| 73 | C T F F Y G S C R G K R N N F K T E E Y |
| 74 | T F F Y G G S R G K R N N F K T E E Y C |
| 75 | P F F Y G G C R G K R N N F K T E E Y |
| 76 | T F F Y G G C R G K R N N F K T K E Y |
| 77 | T F F Y G G K R G K R N N F K T E E Y |
| 78 | T F F Y G G C R G K R N N F K T K R Y |
| 79 | T F F Y G G K R G K R N N F K T A E Y |
| 80 | T F F Y G G K R G K R N N F K T A G Y |
| 81 | T F F Y G G K R G K R N N F K R E K Y |
| 82 | T F F Y G G K R G K R N N F K R A K Y |
| 83 | T F F Y G G C L G N R N N F K T E E Y |
| 84 | T F F Y G C R G K R N N F K T E E Y |
| 85 | T F F Y G G R C G K R N N F K T E E Y |
| 86 | T F F Y G G C L G N G N N F D T E E E |
| 87 | T F Q Y G G C R G K R N N F K T E E Y |
| 88 | Y N K E F G T F N T K G C E R G Y R F |
| 89 | R F K Y G G C L G N M N N F E T L E E |
| 90 | R F K Y G G C L G N K N N F L R L K Y |
| 91 | R F K Y G G C L G N K N N Y L R L K Y |
| 92 | K T K R K R K K Q R V K I A Y E E I F K N Y |
| 93 | K T K R K R K K Q R V K I A Y |
| 94 | R G G R L S Y S R R F S T S T G R |
| 95 | R R L S Y S R R R F |
| 96 | R Q I K I W F Q N R R M K W K K |
| 97 | T F F Y G G S R G K R N N F K T E E Y |
| 98 | M R P D F C L E P P Y T G P C V A R I<br>I R Y F Y N A K A G L C Q T F V Y G G<br>C R A K R N N F K S A E D C M R T C G G A |
| 99 | T F F Y G G C R G K R N N F K T K E Y |
| 100 | R F K Y G G C L G N K N N Y L R L K Y |
| 101 | T F F Y G G C R A K R N N F K R A K Y |
| 102 | N A K A G L C Q T F V Y G G C L A K R N N F<br>E S A E D C M R T C G G A |
| 103 | Y G G C R A K R N N F K S A E D C M R T C G G A |
| 104 | G L C Q T F V Y G G C R A K R N N F K S A E |
| 105 | L C Q T F V Y G G C E A K R N N F K S A |
| 107 | T F F Y G G S R G K R N N F K T E E Y |
| 108 | R F F Y G G S R G K R N N F K T E E Y |
| 109 | R F F Y G G S R G K R N N F K T E E Y |
| 110 | R F F Y G G S R G K R N N F R T E E Y |

TABLE 1-continued

Exemplary Targeting peptides

| SEQ ID NO: | |
|---|---|
| 111 | T F F Y G G S R G K R N N F R T E E Y |
| 112 | T F F Y G G S R G R R N N F R T E E Y |
| 113 | C T F F Y G G S R G K R N N F K T E E Y |
| 114 | T F F Y G G S R G K R N N F K T E E Y C |
| 115 | C T F F Y G G S R G R R N N F R T E E Y |
| 116 | T F F Y G G S R G R R N N F R T E E Y C |
| 117 | Y E E T K F N N R K G R S G G Y F F T |

Polypeptides Nos. 5, 67, 76, and 91, include the sequences of SEQ ID NOS: 5, 67, 76, and 91, respectively, and are amidated at the C-terminus.
Polypeptides Nos. 107, 109, and 110 include the sequences of SEQ ID NOS: 97, 109, and 110, respectively, and are acetylated at the N-terminus.

The targeting peptide may include an amino acid sequence having the formula:

$$X1\text{-}X2\text{-}X3\text{-}X4\text{-}X5\text{-}X6\text{-}X7\text{-}X8\text{-}X9\text{-}X10\text{-}X11\text{-}X12\text{-}X13\text{-}X14\text{-}X15\text{-}X16\text{-}X17\text{-}X18\text{-}X19,$$

where each of X1-X19 (e.g., X1-X6, X8, X9, X11-X14, and X16-X19) is, independently, any amino acid (e.g., a naturally occurring amino acid such as Ala, Arg, Asn, Asp, Cys, Gln, Glu, Gly, His, Ile, Leu, Lys, Met, Phe, Pro, Ser, Thr, Trp, Tyr, and Val) or absent and at least one (e.g., 2 or 3) of X1, X10, and X15 is arginine. X7 can be Ser or Cys; or X10 and X15 each are independently Arg or Lys. The residues from X1 through X19, inclusive, can be substantially identical to any of the amino acid sequences of any one of SEQ ID NOS:1-105 and 107-117 (e.g., Angiopep-1, Angiopep-2, Angiopep-3, Angiopep-4a, Angiopep-4b, Angiopep-5, Angiopep-6, Angiopep-7, and reversed Angiopep-2). At least one (e.g., 2, 3, 4, or 5) of the amino acids from X1-X19 is Arg. The polypeptide can have one or more additional cysteine residues at the N-terminal of the polypeptide, the C-terminal of the polypeptide, or both. For example, the targeting peptide can have an amino acid sequence selected from the group consisting of cys-Angiopep-2 (CysAn$_2$) (SEQ ID NO:113), Angiopep-2-cys (SEQ ID NO:114).

The targeting peptide can be modified, e.g., amidated, acetylated, or both. Such modifications may be at the amino or carboxy terminus of the polypeptide. The peptide or polypeptide may also include peptidomimetics (e.g., those described herein) of any of the polypeptides described herein.

The targeting peptide can have an amino acid sequence described herein with at least one amino acid substitution (e.g., 2, 3, 4, 5, 6, 7, 8, 9, 10, 11, or 12 substitutions), insertion, or deletion or is substantially identical to an amino acid sequence described herein. The peptide or polypeptide may contain, for example, 1 to 12, 1 to 10, 1 to 5, or 1 to 3 amino acid substitutions, for example, 1 to 10 (e.g., to 9, 8, 7, 6, 5, 4, 3, 2) amino acid substitutions. The amino acid substitution(s) may be conservative or non-conservative. For example, the targeting peptide may have an arginine at one, two, or three of the positions corresponding to positions 1, 10, and 15 of the amino acid sequence of any of SEQ ID NO:1, Angiopep-1, Angiopep-2, Angiopep-3, Angiopep-4a, Angiopep-4b, Angiopep-5, Angiopep-6, Angiopep-7, and reversed Angiopep-2.

The invention also features fragments of these polypeptides (e.g., a functional fragment). Truncations of the polypeptide may be 1, 2, 3, 4, 5, 6, 7, 8, 9, 10, 11, 12, or more amino acids from either the N-terminus of the polypeptide, the C-terminus of the polypeptide, or a combination thereof. Other fragments include sequences where internal portions of the polypeptide are deleted.

The targeting peptide of the invention can also have the formula:

$$\text{Lys-Arg-X3-X4-X5-Lys} \quad \text{(formula Ia)},$$

where
X3 is Asn or Gln;
X4 is Asn or Gln; and
X5 is Phe, Tyr, or Trp.

The targeting peptide of the invention can also have the formula:

$$\text{Z1-Lys-Arg-X3-X4-X5-Lys-Z2} \quad \text{(formula Ib)},$$

where
X3 is Asn or Gln;
X4 is Asn or Gln;
X5 is Phe, Tyr, or Trp;
Z1 is absent, Cys, Gly, Cys-Gly, Arg-Gly, Cys-Arg-Gly, Ser-Arg-Gly, Cys-Ser-Arg-Gly, Gly-Ser-Arg-Gly, Cys-Gly-Ser-Arg-Gly, Gly-Gly-Ser-Arg-Gly, Cys-Gly-Gly-Ser-Arg-Gly, Tyr-Gly-Gly-Ser-Arg-Gly, Cys-Tyr-Gly-Gly-Ser-Arg-Gly, Phe-Tyr-Gly-Gly-Ser-Arg-Gly, Cys-Phe-Tyr-Gly-Gly-Ser-Arg-Gly, Phe-Phe-Tyr-Gly-Gly-Ser-Arg-Gly, Cys-Phe-Phe-Tyr-Gly-Gly-Ser-Arg-Gly, Thr-Phe-Phe-Tyr-Gly-Gly-Ser-Arg-Gly, or Cys-Thr-Phe-Phe-Tyr-Gly-Gly-Ser-Arg-Gly; and
Z2 is absent, Cys, Tyr, Tyr-Cys, Cys-Tyr, Thr-Glu-Glu-Tyr, or Thr-Glu-Glu-Tyr-Cys.

The targeting peptide of formulas (Ia) and (Ib) include the amino acid sequence Lys-Arg-Asn-Asn-Phe-Lys and conservative substitutions. Conservative substitutions and derivatives of amino acids and peptides are well known in the art and can be determined by any useful methods (e.g., by using a substitution matrix or any other method described herein). A derivative of a targeting peptide includes a targeting moiety containing one or more conservative substitutions selected from the following groups or a subset of these groups: Ser, Thr, and Cys; Leu, Ile, and Val; Glu and Asp; Lys and Arg; Phe, Tyr, and Trp (e.g., Phe and Tyr); and Gln, Asn, Glu, Asp, and His (e.g., Gln and Asn). Conservative substitutions may also be determined by other methods, such as by the BLAST (Basic Local Alignment Search Tool) algorithm, the BLOSUM substitution matrix (e.g., BLOSUM 62 matrix), and PAM substitution matrix (e.g., PAM 250 matrix).

The targeting peptide can also include those having one or more D-amino acid substitutions, where one or more amino acid residues of formula (Ia) or (Ib) are substituted with a corresponding D-isomer. D-amino acid substitutions may provide peptides having increased resistance to cleavage by digestive enzymes (e.g., pepsin and/or trypsin). For example, one or more of amino acids in formula (Ia) or (Ib) having possible cleavage sites by pepsin or trypsin can be substituted with the D-isomer of that amino acid. Exemplary cleavage sites in formula (Ia) or (Ib) by pepsin and trypsin include the bond that is N-terminal or C-terminal to position 1 for Lys; position 2 for Arg; position 5 for X5 being Phe, Tyr, or Trp; and position 6 for Lys. Accordingly, the polypeptides of the invention also include those having one or more D-isomers for the amino acids recited at positions 1, 2, 5, and/or 6 of formula (Ia) or (Ib).

The targeting peptide of the invention can also have the formula:

X1-X2-Asn-Asn-X5-X6    (formula IIa), where
  X1 is Lys or D-Lys;
  X2 is Arg or D-Arg;
  X5 is Phe or D-Phe; and
  X6 is Lys or D-Lys; and
  where at least one of X1, X2, X5, or X6 is a D-amino acid.

The targeting peptide of the invention can also have the formula:

X1-X2-Asn-Asn-X5-X6-X7    (formula IIb), where
  X1 is Lys or D-Lys;
  X2 is Arg or D-Arg;
  X5 is Phe or D-Phe;
  X6 is Lys or D-Lys;
  X7 is Tyr or D-Tyr; and
  where at least one of X1, X2, X5, X6, or X7 is a D-amino acid.

The targeting peptide of the invention can also have the formula:

Z1-X1-X2-Asn-Asn-X5-X6-X7-Z2    (formula IIc), where
  X1 is Lys or D-Lys;
  X2 is Arg or D-Arg;
  X5 is Phe or D-Phe;
  X6 is Lys or D-Lys;
  X7 is Tyr or D-Tyr;
  Z1 is absent, Cys, Gly, Cys-Gly, Arg-Gly, Cys-Arg-Gly, Ser-Arg-Gly, Cys-Ser-Arg-Gly, Gly-Ser-Arg-Gly, Cys-Gly-Ser-Arg-Gly, Gly-Gly-Ser-Arg-Gly, Cys-Gly-Gly-Ser-Arg-Gly, Tyr-Gly-Gly-Ser-Arg-Gly, Cys-Tyr-Gly-Gly-Ser-Arg-Gly, Phe-Tyr-Gly-Gly-Ser-Arg-Gly, Cys-Phe-Tyr-Gly-Gly-Ser-Arg-Gly, Phe-Phe-Tyr-Gly-Gly-Ser-Arg-Gly, Cys-Phe-Phe-Tyr-Gly-Gly-Ser-Arg-Gly, Thr-Phe-Phe-Tyr-Gly-Gly-Ser-Arg-Gly, or Cys-Thr-Phe-Phe-Tyr-Gly-Gly-Ser-Arg-Gly; and Z2 is absent, Cys, Tyr, Tyr-Cys, Cys-Tyr, Thr-Glu-Glu-Tyr, or Thr-Glu-Glu-Tyr-Cys; where at least one of X1, X2, X5, X6, or X7 is a D-amino acid; and where the polypeptide optionally includes one or more D-isomers of an amino acid recited in Z1 or Z2.

The targeting peptides of the invention include additions and deletions of amino acids to the formula of Lys-Arg-X3-X4-X5-Lys (formula Ia), where X3-X5 are as defined above; the formulae of X1-X2-Asn-Asn-X5-X6 and X1-X2-Asn-Asn-X5-X6-X7 (formulas IIa and IIb, respectively), where X1, X2, X5, X6, and X7 are as defined above; or the longer polypeptide of 3D-An2, as described herein. The deletions or additions can include any part of the formula of Lys-Arg-X3-X4-X5-Lys, X1-X2-Asn-Asn-X5-X6, X1-X2-Asn-Asn-X5-X6-X7, Lys-Arg-Asn-Asn-Phe-Lys, D-Lys-D-Arg-Asn-Asn-D-Phe-D-Lys, or D-Lys-D-Arg-Asn-Asn-D-Phe-D-Lys-D-Tyr, or of the longer sequence 3D-An2. Deletions or additions of 1, 2, 3, 4, or 5 amino acids may be made from the consensus sequence of the targeting moiety. Any useful substitutions, additions, and deletions can be made that does not destroy significantly the desired biological activity (e.g., ability to cross the BBB or agonist activity) of the targeting peptide. The modification may reduce (e.g., by at least 5%, 10%, 20%, 25%, 35%, 50%, 60%, 70%, 75%, 80%, 90%, or 95%), may have no effect, or may increase (e.g., by at least 5%, 10%, 25%, 50%, 100%, 200%, 500%, or 1000%) the biological activity of the consensus sequence or original polypeptide.

In particular, substitutions or additions of D-amino acids can be made within the targeting peptide. Such substitutions or additions may provide peptides having increased resistance to cleavage by enzymes, where one of more amino acids for cleavage sites can be substituted with its D-isomer. Exemplary enzymes include pepsin, trypsin, Arg-C proteinase, Asp-N endopeptidase, chymotrypsin, glutamyl endopeptidase, LysC lysyl endopeptidase, LysN peptidyl-Lys metalloendopeptidase, proteinase K, and thermolysin; and exemplary cleavage sites for these enzymes are described herein.

Furthermore, substitutions, additions and deletions may have or may optimize a characteristic of the targeting peptide, such as charge (e.g., positive or negative charge), hydrophilicity, hydrophobicity, in vivo stability, bioavailability, toxicity, immunological activity, immunological identity, and conjugation properties. For example, positive charge can be promoted by deleting one or more amino acids (e.g., from 1 to 3 amino acids) that are not basic/positively charged (as described below based on common side chain properties) or less positively charged (e.g., as determined by pKa). In another example, positive charge can be promoted by inserting one or more amino acids (e.g., from 1 to 3 amino acids) that are basic/positively charged or more positively charged (e.g., as determined by pKa).

Agents and Conjugation of Agents to Dendrimer-Targeting Peptide Complex

Any agent may be chemically conjugated to the dendrimer-targeting peptide complex. Such agents include small-molecule drugs, antibiotics, anticancer agents, an imaging agent (e.g., a radio imaging agent), a diagnostic agent, a therapeutic agent, a reporter molecule, RNAi agents, and peptide and polypeptide therapeutics. The agents are conjugated via a functional group present on the dendrimer-targeting peptide complex. The functional group can include, without limitations, maleimide, a hydrazide, an azide, a haloacetamide, and an alkoxyamine. In addition, any of the linkers described above can also be used to conjugate an agent to the dendrimer-targeting peptide complex.

The compound of the invention can have a first agent attached to the dendrimer-targeting peptide complex at one location, for example a first agent can be attached to the core moiety. The compound of the invention can also have an optional second agent attached to the dendrimer-targeting peptide complex at a second location, for example one or more second agents attached to one or more targeting peptides or to one or more surface branches. A second agent may be attached to the targeting peptide or the surface branch via a linker. A second agent, when present, may be the same as the agent or may be a different type of agent compared to the first agent, e.g., the first agent is one cytotoxic agent and the second agent is a second cytotoxic agent, and the combination of cytotoxic agents are a combination therapy for a disease.

Manufacturing Compounds of the Invention

The invention features methods to synthesize the compounds that include a complex of dendrimer, targeting peptides and one or more agents. Dendrimers with a variety of core moieties and branch moieties, and with different numbers of surface branches and reactive groups are commercially available. The dendrimer can be conjugated to multiple Angiopep peptides via reactive groups on surface branches. For example, this can be done by reacting a dendrimer with N-Succinimidyl 3-(2-pyridyldithio)-propionate to form a dendrimer-pyridyl-disulfide intermediate; and then reacting the dendrimer-pyridyl-disulfide intermediate with targeting peptides containing cysteine residues to attach a targeting peptide to each of the surface branches. Alternatively, the dendrimer can be reacted with N-succinimidyl S-acetylthioacetate to form a dendrimer-sulfhydryl intermediate followed by a reaction with a maleimide derivative of targeting peptides to form a dendrimer-targeting peptide complex.

The dendrimer-targeting peptide complex is then reacted with a first agent as described above and the resulting dendrimer-targeting peptide-first agent complex can be produced in a pharmaceutically acceptable form (e.g., a pharmaceutically acceptable salt).

Alternatively, the dendrimer can first be reacted with a first agent via a functional group (e.g., azide), and the surface branches of the resulting dendrimer-first agent complex can be functionalized to attach surface branches.

The method of manufacturing a compound of the invention may additionally involve attachment of any of the linkers described above to the dendrimer prior to attachment of the targeting peptides or the first agent.

The method of manufacturing a compound of the invention may optionally involve attachment of one or more second agents to the compound, at locations that may be different than the first agent. For example, one or more second agents can be attached to one or more of the targeting peptides. Alternatively, one or more second agents can be attached to one or more of the surface branches of the dendrimer. At each of these locations, the attachment of a second agent can involve the use of a linker as described above.

Assays to Determine Accumulation of Compound of the Invention in Tissues

Assays to determine accumulation of the compound of the invention in tissues may be performed to evaluate the transport capabilities of multiple targeting peptides attached to a dendrimer. Labeled compounds can be administered to an animal, and accumulation in different organs can be measured. For example, a dendrimer-targeting peptide complex conjugated to a detectable label (e.g., a near-IR fluorescence spectroscopy label such as Cy5.5) allows live in vivo visualization. Such a compound can be administered to an animal, and the presence of the polypeptide in an organ can be detected, thus allowing determination of the rate and amount of accumulation of the polypeptide in the desired organ. The compound can also be labeled with a radioactive isotope (e.g., $^{125}$I). The compound is then administered to an animal. After a period of time, the animal is sacrificed and the organs are extracted. The amount of radioisotope in each organ can then be measured using any means known in the art. By comparing the amount of a labeled candidate compound in a particular organ relative to the amount of a labeled control compound, the ability of the candidate compound to access and accumulate in a particular tissue can be ascertained. In one aspect of the invention, the transport of multiple Angiopep peptides (e.g., Angiopep-2) across the BBB is compared to the transport of a single Angiopep peptide (e.g., Angiopep-2)

Administration and Dosage of Compound of the Invention

The present invention also features pharmaceutical compositions that contain a therapeutically effective amount of a compound of the invention. The composition can be formulated for use in a variety of drug delivery systems. One or more physiologically acceptable excipients or carriers can also be included in the composition for proper formulation. Suitable formulations for use in the present invention are found in *Remington's Pharmaceutical Sciences*, Mack Publishing Company, Philadelphia, Pa., 17th ed., 1985. For a brief review of methods for drug delivery, see, e.g., Langer (Science 249:1527-1533, 1990).

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that include the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. Compositions of the invention can be administered to the subject (e.g., a human) in an amount sufficient to delay, reduce, or preferably prevent the onset of clinical disease. In therapeutic applications, compositions are administered to a subject (e.g., a human) already suffering from disease in an amount sufficient to cure or at least partially arrest the symptoms of the condition and its complications. An amount adequate to accomplish this purpose is defined as a "therapeutically effective amount," an amount of a compound sufficient to substantially improve some symptom associated with a disease or a medical condition. For example, in the treatment of a neurodegenerative disease (e.g., those described herein), an agent or compound that decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Amounts effective for this use may depend on the severity of the disease or condition and the weight and general state of the subject, but generally range from about 0.05 μg to about 1000 μg (e.g., 0.5-100 μg) of an equivalent amount of the agent per dose per subject. Suitable regimes for initial administration and booster administrations are typified by an initial administration followed by repeated doses at one or more hourly, daily, weekly, or monthly intervals by a subsequent administration. The total effective amount of an agent present in the compositions of the invention can be administered to a mammal as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month). Alternatively, continuous intravenous infusion sufficient to maintain therapeutically effective concentrations in the blood are contemplated.

The therapeutically effective amount of one or more agents present within the compositions of the invention and used in the methods of this invention applied to mammals (e.g., humans) can be determined by the ordinarily-skilled artisan with consideration of individual differences in age, weight, and the condition of the mammal. Because certain compounds of the invention exhibit an enhanced ability to cross the BBB, the dosage of the compounds of the invention can be lower than (e.g., less than or equal to about 90%, 75%, 50%, 40%, 30%, 20%, 15%, 12%, 10%, 8%, 7%, 6%, 5%, 4%, 3%, 2%, 1%, 0.5%, or 0.1% of) the equivalent dose of required for a therapeutic effect of the unconjugated agonist. The agents of the invention are administered to a subject (e.g. a mammal, such as a human) in an effective amount, which is an amount that produces a desirable result in a treated subject (e.g., preservation of neurons, new neuronal growth). Therapeutically effective amounts can also be determined empirically by those of skill in the art.

Single or multiple administrations of the compositions of the invention including an effective amount can be carried out with dose levels and pattern being selected by the treating physician. The dose and administration schedule can be determined and adjusted based on the severity of the disease or condition in the subject, which may be monitored throughout the course of treatment according to the methods commonly practiced by clinicians or those described herein.

The compounds of the present invention may be used in combination with either conventional methods of treatment or therapy or may be used separately from conventional methods of treatment or therapy.

When the compounds of this invention are administered in combination therapies with other agents, they may be administered sequentially or concurrently to an individual. Alternatively, pharmaceutical compositions according to the present invention may be comprised of a combination of a compound of the present invention in association with a pharmaceutically acceptable excipient, as described herein, and another therapeutic or prophylactic agent known in the art.

EXAMPLES

Example 1

Synthesis of propagyl-PAMAM dendrons

Propagyl-PAMAM dendrons 1-D0, 1-D1, 1-D2 were prepared using a modified version (as shown in the schematic below) of the synthesis protocol described in Lee et al (*Macromolecules* 2006, 39, 2418-2422, incorporated herein by reference).

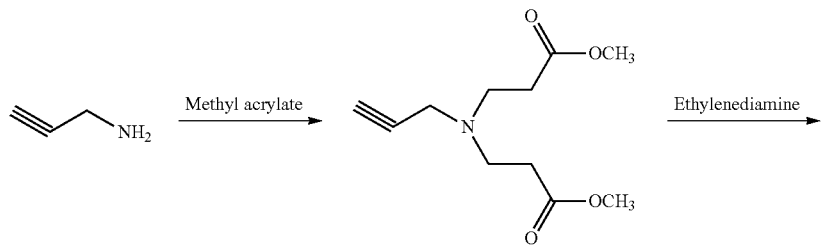

-continued
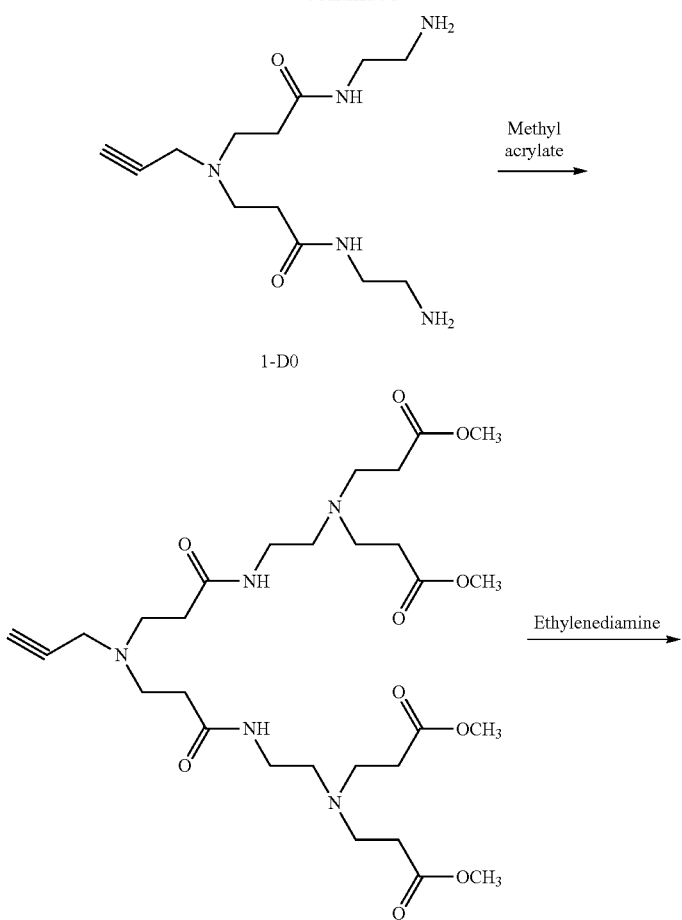
1-D0
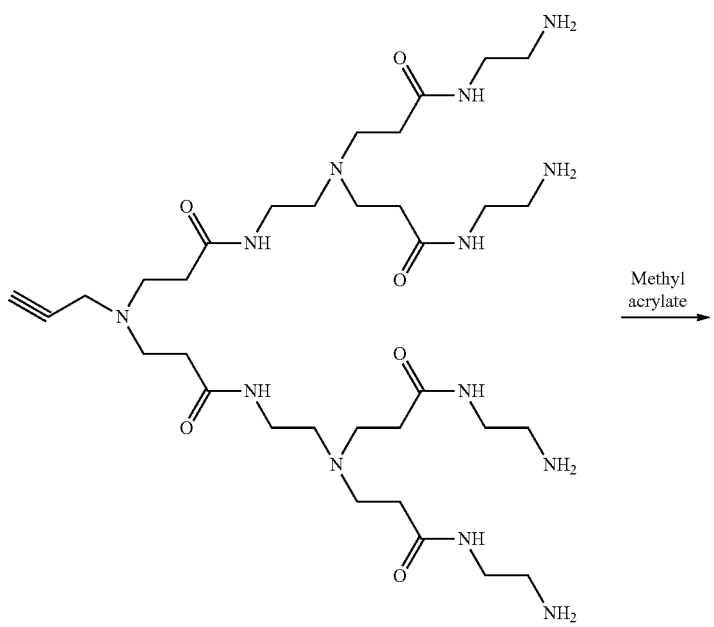
1-D1

-continued
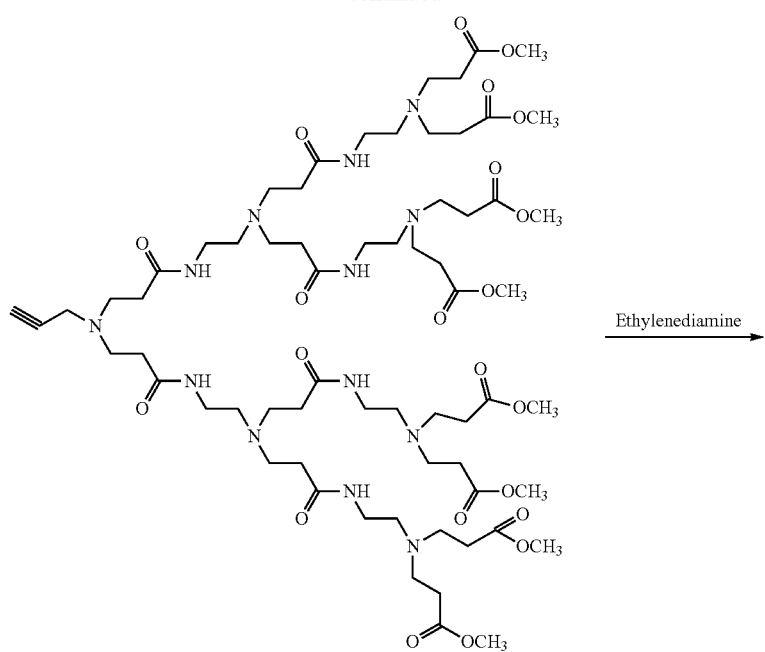
Ethylenediamine →
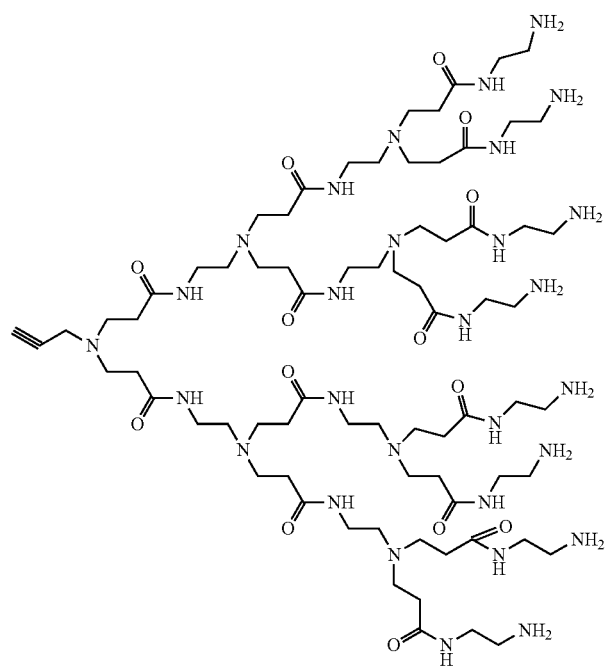
1-D2

Example 2
Synthesis of azido-PAMAM dendrons
Azido-PAMAM dendrons 2-D0, 2-D1, 2-D2 were prepared using a modified version (as shown in the schematic below) of the synthesis protocol described in Lee et al (*Tetrahedron* 2006, 62, 9193-9200, incorporated herein by reference).
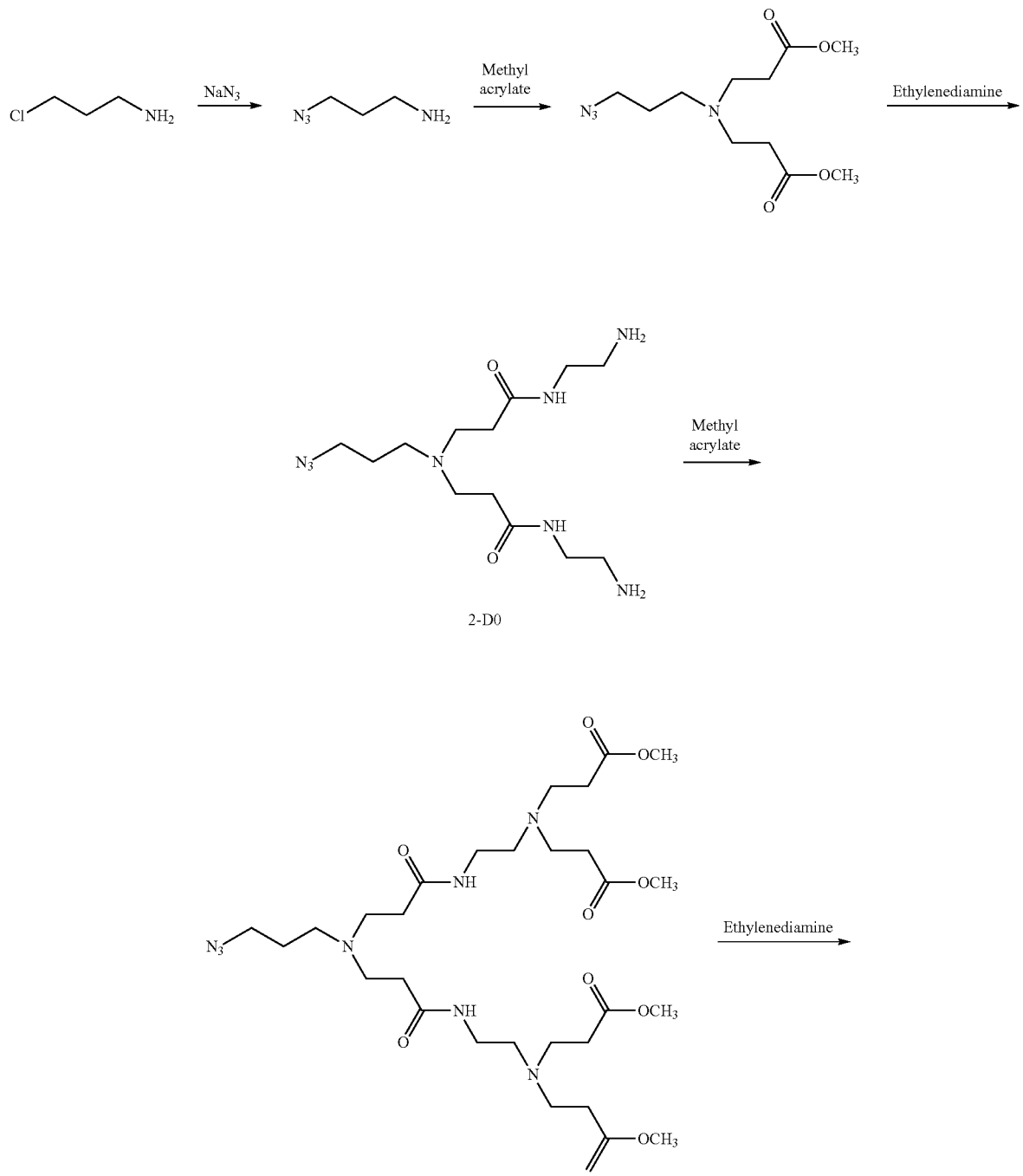

-continued
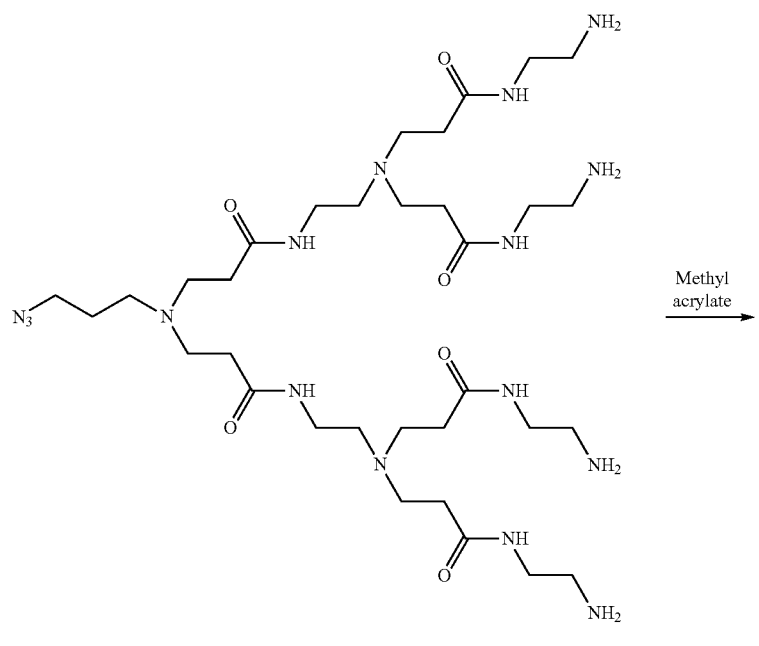
2-D1
→ Methyl acrylate
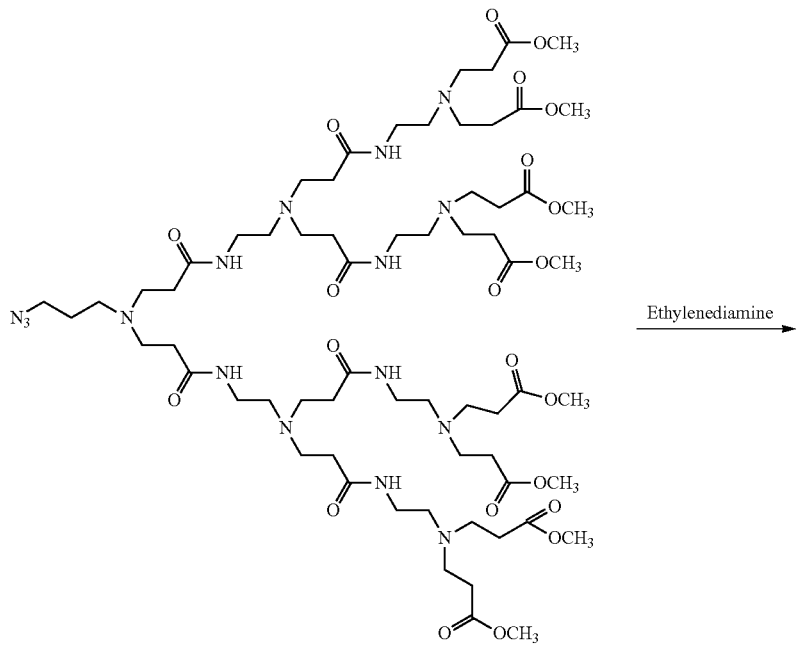
→ Ethylenediamine

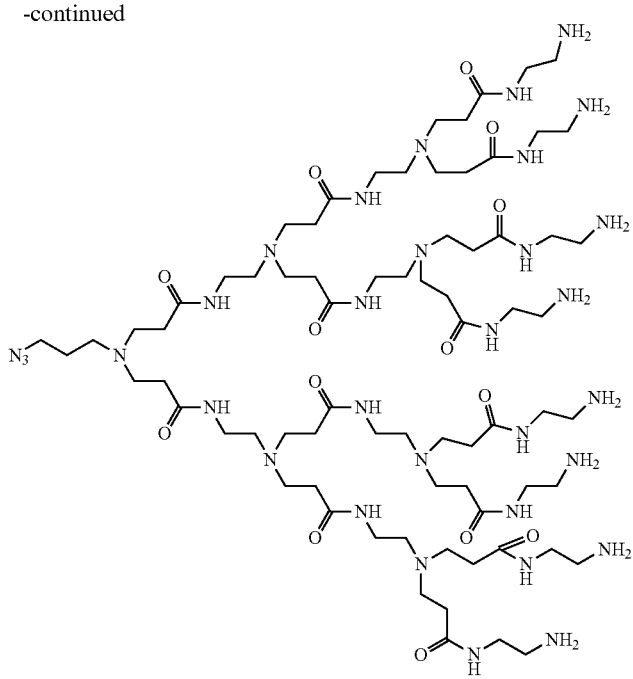

2-D2

Example 3

Synthesis of azido-PAMAM(0)-(SSPy)$_2$

Azido-PAMAM 2-D0 (66 mg, 0.2 mmol) was dissolved in DMF (1.3 ml). SPDP (125 mg, 0.4 mmol) was then added. The mixture was stirred at room temperature for 1 h, diluted with 0.1% TFA in water (20 ml). The resulting solution was directly loaded on to a phenyl 42 ml column. Preparative HPLC purification (8% ACN/H$_2$O to 40% ACN/H$_2$O with 0.05% TFA) produced 65 mg of pure azido-PAMAM(0)-SSPy, 45%. UPLC purity, 95%. HRMS (Microtof, ESI) m/z, calcd. for C$_{29}$H$_{42}$N$_{10}$O$_4$S$_4$, 722.2273. found 723.2184 (M+1).

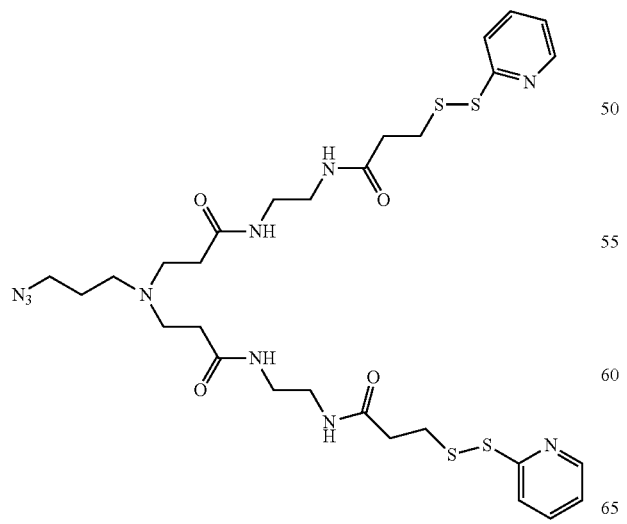

Example 4
Synthesis of azido-PAMAM(0)-(SSCysAn2)₂

A mixture of azido-PAMAM(0)-SSPy (40 mg, 55.5 μmol), An2Cys (240 mg, 80 μmol) and NaHCO₃ (30 mg, 0.35 mmol) in DMSO (1.5 ml) and DMF (1.5 ml) was stirred at room temperature under argon for 1 h. After cooling to 0 OC, the reaction mixture was diluted with 0.1% TFA in water (30 ml), and directly loaded to a phenyl 42 ml column for purification (8% ACN/H₂O to 40% ACN/H₂O with 0.05% TFA). Pure product azido-PAMAM(0)-(SSAn2)₂ (127 mg, 43%) was obtained as a colorless power after lyophilization. UPLC purity, 95%. HRMS (Microtof, ESI) m/z, calcd. for $C_{233}H_{340}N_{68}O_{68}S_4$, 5308.4187. found 1327.8346 (4+), 1062.6763 (5+), 885.5691 (6+).

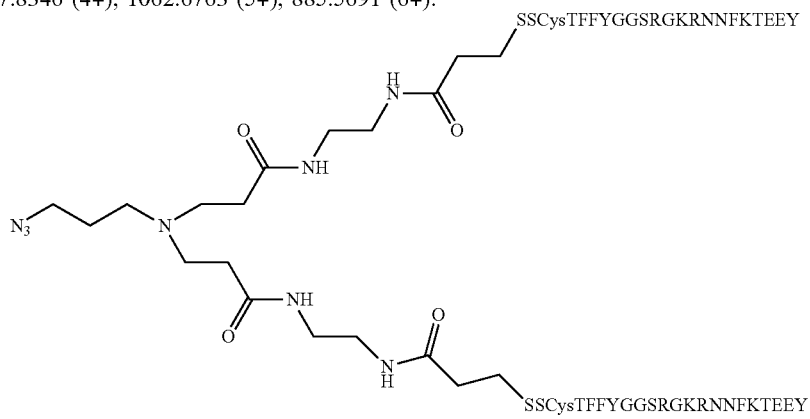

Example 5
Synthesis of propagyl-PAMAM(1)-(SSPy)₄

Propagyl-PAMAM 1-D1 (45 mg, 0.06 mmol) was dissolved in DMF (1.0 ml). SPDP (75 mg, 0.24 mmol) was then added. The mixture was stirred at room temperature for 1 h, diluted with 0.1% TFA in water (20 ml). The resulting solution was directly loaded to a phenyl 42 ml column for HPLC purification (8% ACN/H₂O to 40% ACN/H₂O with 0.05% TFA) resulting in a pure product of propagyl-PAMAM(1)-(SSPy)₄ 50 mg, 55%. UPLC purity, 95%. HRMS (Microtof, ESI) m/z, calcd. for $C_{65}H_{93}N_{17}O_{10}S_8$, 1527.5057. found 1528.4723 (M+1).

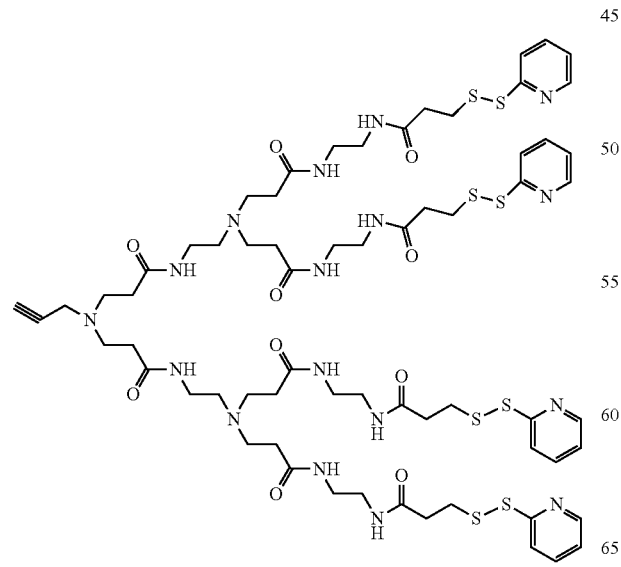

Example 6

Synthesis of Propagyl-PAMAM(1)-(SSCysAn2)₄

A mixture of propagyl-PAMAM(1)-(SSPy)₄ (20 mg, 13 μmol), An2Cys (125 mg, 52 μmol) and NaHCO₃ (12 mg, 0.14 mmol) in DMSO (0.8 ml) and DMF (0.8 ml) was stirred at room temperature under argon for 2.5 h. After cooling to 0 OC, the reaction mixture was diluted with 0.1% TFA in water (15 ml) and directly loaded to a phenyl 42 ml column for purification (8% ACN/H₂O to 40% ACN/H₂O with 0.05% TFA). Pure product propagyl-PAMAM(1)-(SS-CysAn2)₄ (91 mg, 65%) was obtained as a colorless power after lyophilization. UPLC purity, 95%. HRMS (Microtof, ESI) m/z, calcd. for $C_{473}H_{689}N_{133}O_{138}S_8$, 10700.8918. found 2675.6306 (4+), 2140.7530 (5+), 1529.4280 (7+).

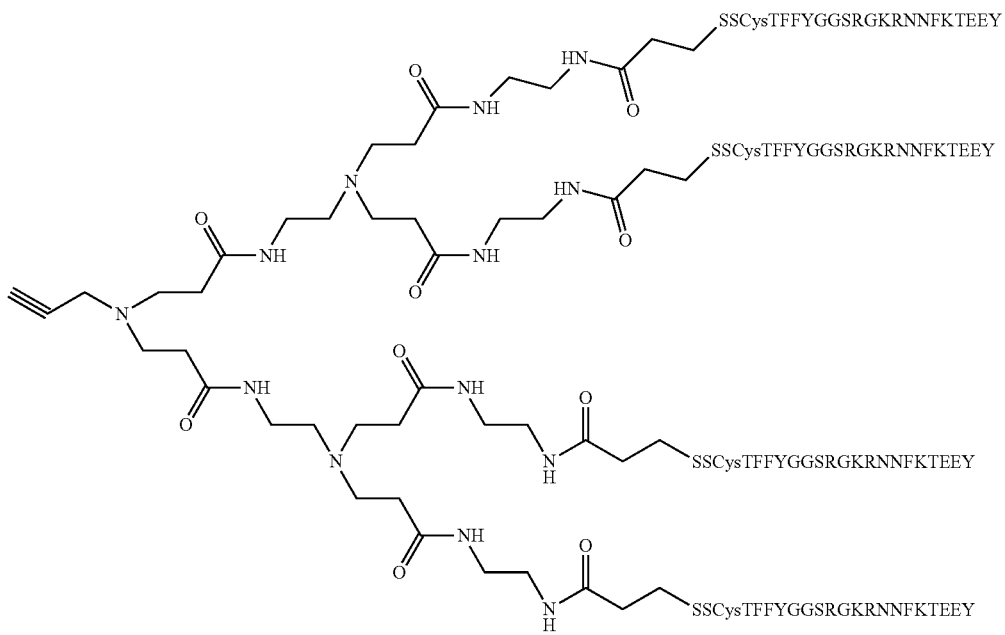

Example 7

Synthesis of propagyl-PAMAM(1)-(SAc)₄

Propagyl-PAMAM 1-D1 (111 mg, 0.15 mmol) was dissolved in DMF (2.0 ml). SATA (139 mg, 0.6 mmol) in DMSO (1 ml) was then added. The mixture was stirred at room temperature for 1.5 h, diluted with 0.1% TFA in water (40 ml). The resulting solution was directly loaded to a phenyl 42 ml column for HPLC purification (4% ACN/H₂O to 30% ACN/H₂O with 0.05% TFA) resulting in pure product of propagyl-PAMAM(1)-(Sac)₄ 72 mg, 40%. UPLC purity, 95%. HRMS (Microtof, ESI) m/z, calcd. for $C_{49}H_{81}N_{13}O_{14}S_4$, 1203.4909. found 1204.4896 (M+1).

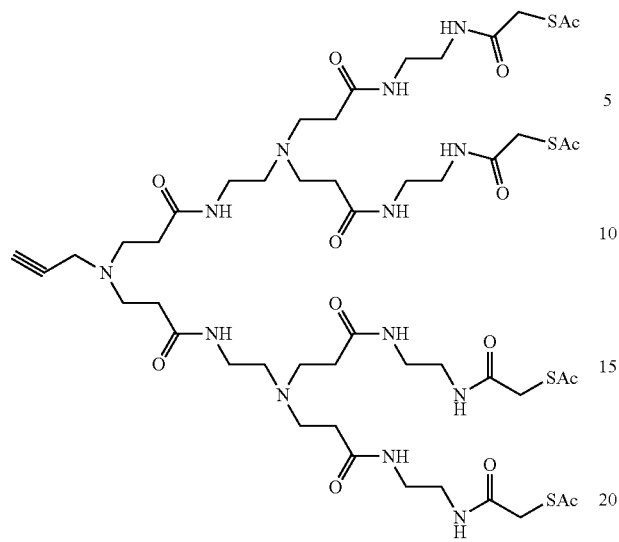

Example 8

Synthesis of propagyl-PAMAM(1)-(SMaI-An2)$_4$

Into a solution of propagyl-PAMAM(1)-(Sac)$_4$ (17.4 mg, 14.4 µmol) in phosphate buffer pH 7.2 (1 ml) NH$_2$OH.HCl (0.5 M, 0.07 ml) was added. The mixture was stirred at room temperature for 2 h. Next, maleimide-An2 (78 mg, 66 µmol) in DMSO (1.5 ml) was added and the reaction mixture was stirred at room temperature overnight. After cooling to 0° C., the reaction mixture was diluted with 0.1% TFA in water (40 ml), and directly loaded to a C4 24 ml column for purification (4% ACN/H$_2$O to 40% ACN/H$_2$O with 0.05% TFA). Pure product of propagyl-PAMAM(1)-(SMaI-An2)$_4$ (33 mg, 21%) was obtained as a colorless power after lyophilization. UPLC purity, 95%. HRMS (Microtof, ESI) m/z, calcd. for C$_{505}$H$_{729}$N$_{133}$O$_{158}$S$_4$, 11317.2149. found 2830.8163 (4+), 2264.8163 (5+), 1887.5322 (6+).

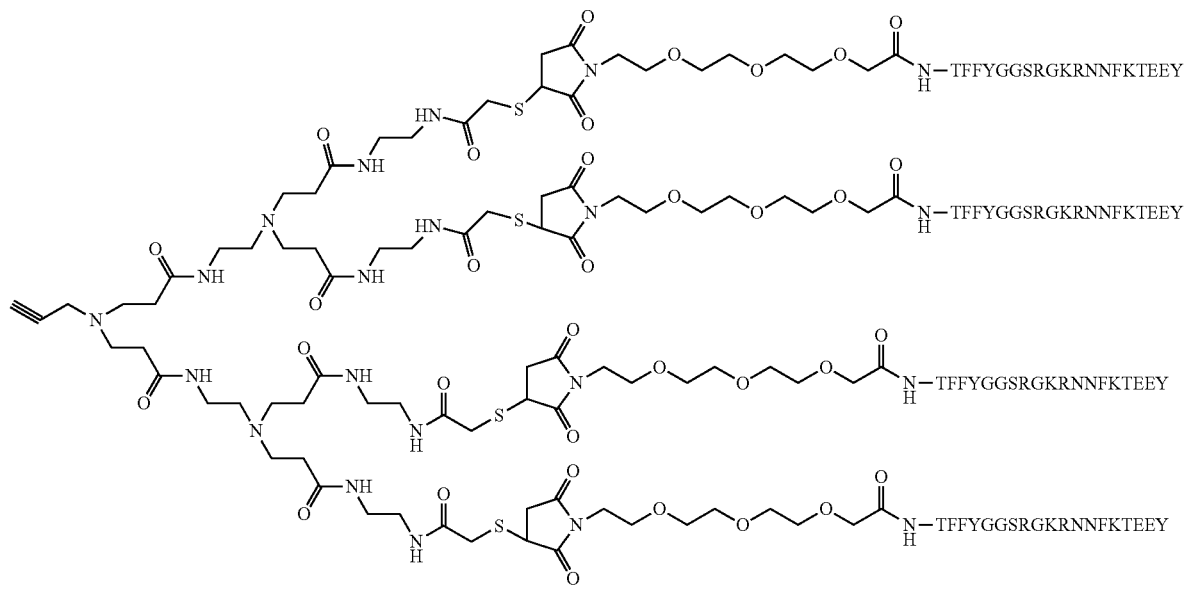

Example 9

Synthesis of azido-PAMAM(1)-(SSPy)$_4$

Azido-PAMAM 2-D1 (86 mg, 0.11 mmol) was dissolved in DMF (2.0 ml). SPDP (137 mg, 0.44 mmol) in DMSO (1 ml) was then added. The mixture was stirred at room temperature for 1 h, diluted with 0.1% TFA in water (30 ml). The resulting solution was directly loaded to a phenyl 42 ml column for HPLC purification (8% ACN/H$_2$O to 40% ACN/H$_2$O with 0.05% TFA) resulting in a pure product of azido-PAMAM(1)-SSPy 85 mg, 49%. UPLC purity, 95%. HRMS (Microtof, ESI) m/z, calcd. for C$_{65}$H$_{96}$N$_{20}$O$_{10}$S$_8$, 1572.5384. found 1573.4874 (M+1).

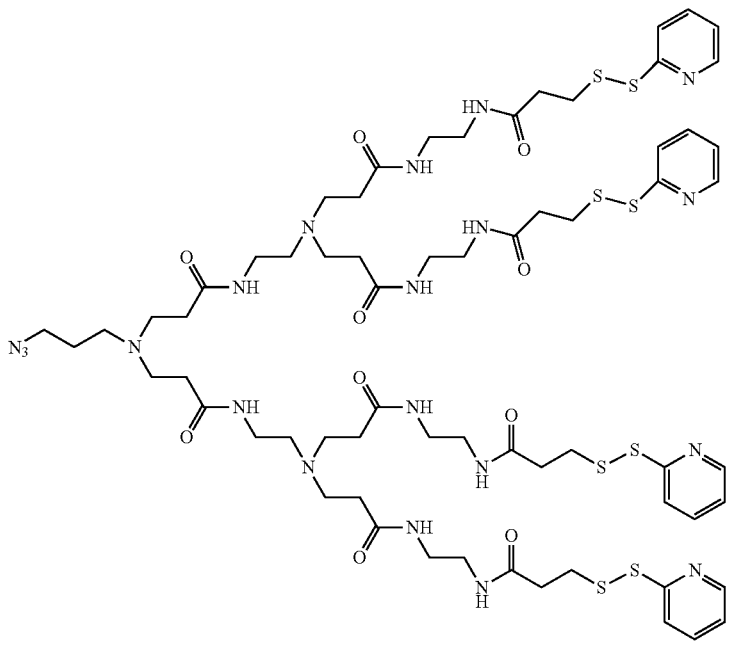 [SMILES: [N-]=[N+]=NCCCN(CCC(=O)NCCN(CCC(=O)NCCNC(=O)CCSSc1ccccn1)CCC(=O)NCCNC(=O)CCSSc1ccccn1)CCC(=O)NCCN(CCC(=O)NCCNC(=O)CCSSc1ccccn1)CCC(=O)NCCNC(=O)CCSSc1ccccn1]

Example 10

Synthesis of azido-PAMAM(1)-(SSCysAn2)$_4$

A mixture of azido-PAMAM(1)-(SSPy)$_4$ (30 mg, 19 μmol), An2Cys (183 mg, 76 μmol) and NaHCO$_3$ (18 mg, 0.14 mmol) in DMSO (1.2 ml) and DMF (1.2 ml) was stirred at room temperature under argon for 3 h. After cooling to 0° C., the reaction mixture was diluted with 0.1% TFA in water (25 ml), and directly loaded to a C4 24 ml column for purification (8% ACN/H$_2$O to 40% ACN/H$_2$O with 0.05% TFA). Pure product of azido-PAMAM(1)-(SSCysAn2)$_4$ (88 mg, 43%) was obtained as a colorless power after lyophilization. UPLC purity, 95%. HRMS (Microtof, ESI) m/z, calcd. for C$_{473}$H$_{692}$N$_{136}$O$_{138}$S$_8$, 10745.9245. found 1791.6586 (6+), 1535.8257 (7+), 1343.9730 (8+), 1075.3835 (10+).

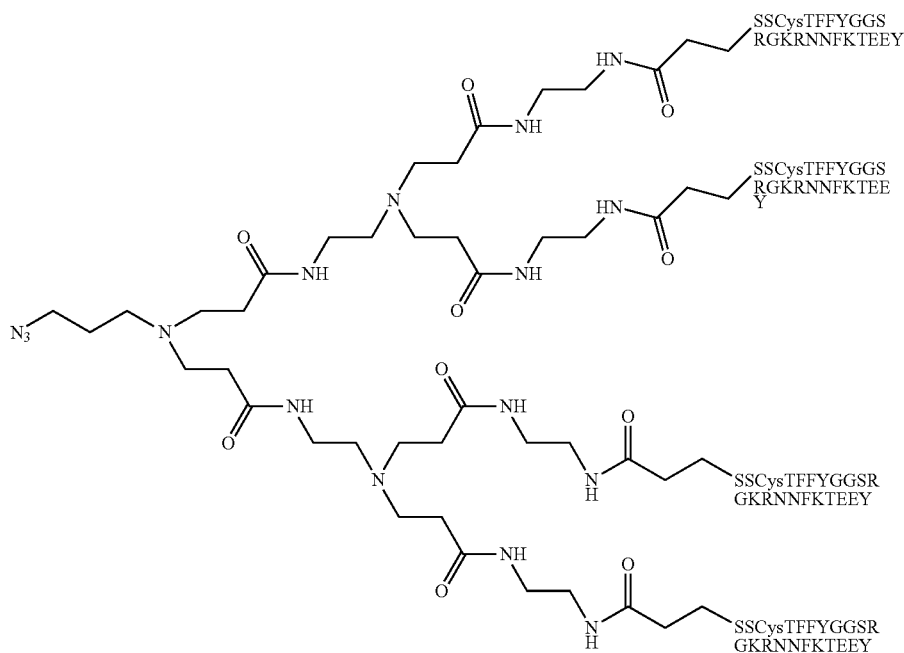

Example 11

Synthesis of azido-PAMAM(1)-(SAc)₄

Azido-PAMAM 2-D1 (102 mg, 0.13 mmol) was dissolved in DMF (2.0 ml). SATA (120 mg, 0.52 mmol) in DMSO (1.5 ml) was then added. The mixture was stirred at room temperature for 1.5 h, diluted with 0.1% TFA in water (30 ml). The resulting solution was directly loaded to a phenyl 42 ml column for HPLC purification (4% ACN/H₂O to 30% ACN/H₂O with 0.05% TFA) yielding a pure product of azido-PAMAM(1)-(Sac)₄ 57 mg, 35%. UPLC purity, 95%. HRMS (Microtof, ESI) m/z, calcd. for $C_{49}H_{80}N_{16}O_{14}S_4$, 1248.5236. found 1249.4825 (M+1).

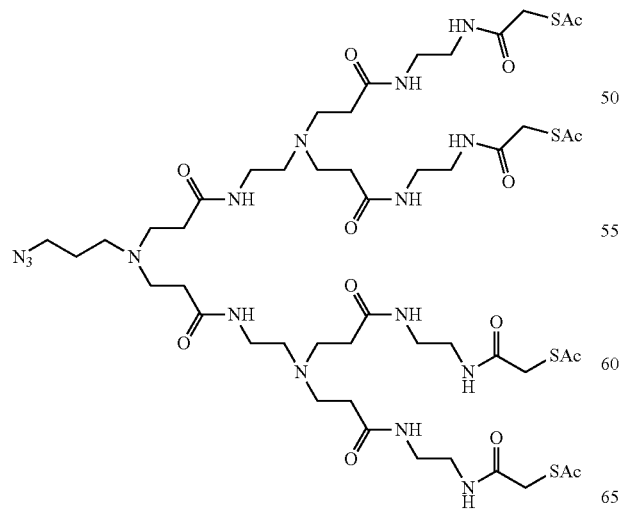

Example 12

Synthesis of azido-PAMAM(1)-(SMaI-An2)$_4$

Into a solution of azido-PAMAM(1)-(Sac)$_4$ (30 mg, 24 μmol) in phosphate buffer pH 7.2 (1.5 ml) NH$_2$OH.HCl (0.5 M, 0.3 ml) was added. The mixture was stirred at room temperature for 2 h. Maleomide-An2 (160 mg, 65 μmol) in DMSO (2 ml) was added and the reaction mixture was stirred at room another 2 h. After cooling to 0 OC, the reaction mixture was diluted with 0.1% TFA in water (30 ml), and directly loaded to a C4 24 ml column for purification (4% ACN/H$_2$O to 40% ACN/H$_2$O with 0.05% TFA). Pure product of azidol-PAMAM(1)-(SMaI-An2)$_4$ (54 mg, 20%) was obtained as a colorless power after lyophilization. UPLC purity, 95%. HRMS (Microtof, ESI) m/z, calcd. for C$_{505}$H$_{728}$N$_{136}$O$_{158}$S$_4$, 11358.2163. found 2841.9829 (4+), 2273.7718 (5+), 1894.9193 (6+), 1421.5047 (8+).

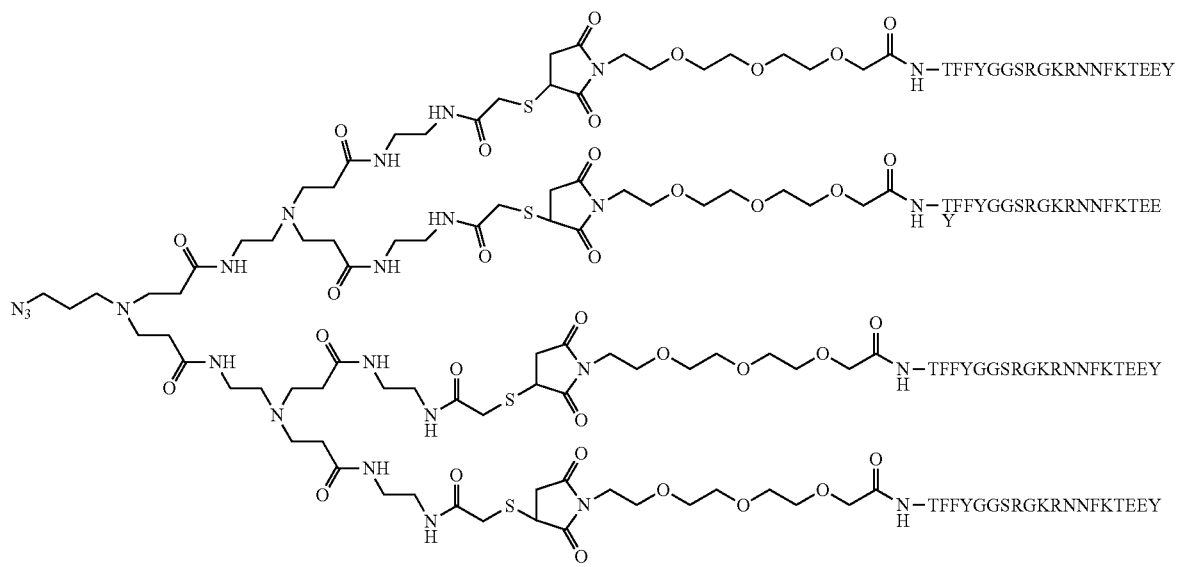

Example 13

Synthesis of propagyl-PAMAM(2)-(SSPy)$_8$

Propagyl-PAMAM 1-D2 (84 mg, 0.05 mmol) was dissolved in DMF (1.2 ml). SPDP (129 mg, 0.41 mmol) in DMSO (8 ml) was then added. The mixture was stirred at room temperature for 1 h, diluted with 0.1% TFA in water (20 ml). The resulting solution was directly loaded to a phenyl 42 ml column for HPLC purification (8% ACN/H$_2$O to 40% ACN/H$_2$O with 0.05% TFA) yielding a pure product of propagyl-PAMAM(2)-(SSPy)$_8$ 36 mg, 22%. %. UPLC purity, 95%. HRMS (Microtof, ESI) m/z, calcd. for C$_{137}$H$_{201}$N$_{37}$O$_{22}$S$_{16}$, 3229.1312. found 1616.5492 (2+), 1077.7144 (3+).

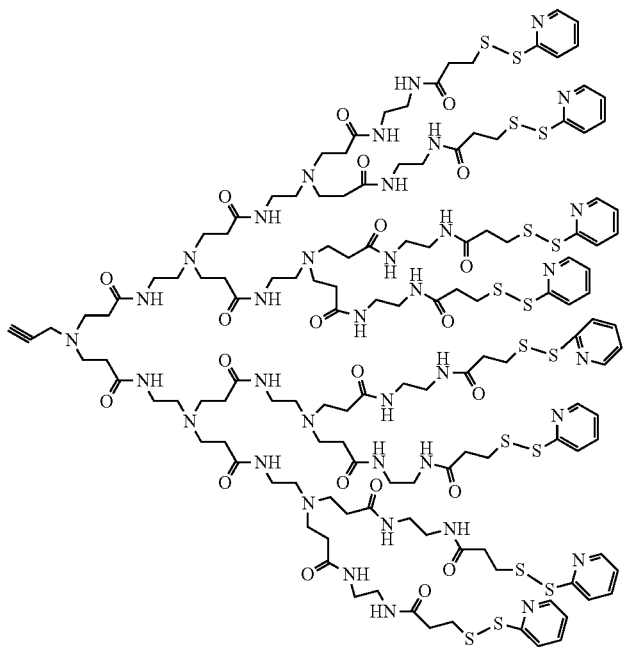 [SMILES: C#CCN(CCC(=O)NCCN(CCC(=O)NCCN(CCC(=O)NCCNC(=O)CCSSc1ccccn1)CCC(=O)NCCNC(=O)CCSSc1ccccn1)CCC(=O)NCCN(CCC(=O)NCCNC(=O)CCSSc1ccccn1)CCC(=O)NCCNC(=O)CCSSc1ccccn1)CCC(=O)NCCN(CCC(=O)NCCN(CCC(=O)NCCNC(=O)CCSSc1ccccn1)CCC(=O)NCCNC(=O)CCSSc1ccccn1)CCC(=O)NCCN(CCC(=O)NCCNC(=O)CCSSc1ccccn1)CCC(=O)NCCNC(=O)CCSSc1ccccn1]

Example 14

Synthesis of propagyl-PAMAM(2)-(SSCysAn2)₈

A mixture of Propagyl-PAMAM(2)-(SSPy)₈ (35 mg, 11 μmol), An2Cys (200 mg, 88 μmol) and NaHCO₃ (22 mg, 0.26 mmol) in DMSO (2 ml) and DMF (2 ml) was stirred at room temperature under argon for 2 h. After cooling to 0° C., the reaction mixture was diluted with 0.1% TFA in water (25 ml), and directly loaded to a C4 24 ml column for purification (8% ACN/H₂O to 40% ACN/H₂O with 0.05% TFA). Pure product of propagyl-PAMAM(2)-(SSCysAn2) (70 mg, 30%) was obtained as a colorless powder after lyophilization. UPLC purity, 95%. HRMS (Microtof, ESI) m/z, calcd. for $C_{953}H_{1393}N_{269}O_{278}S_{19}$, 21575.2346. found 2397.8071 (9+), 2158.0533 (10+), 1962.0438 (11+).

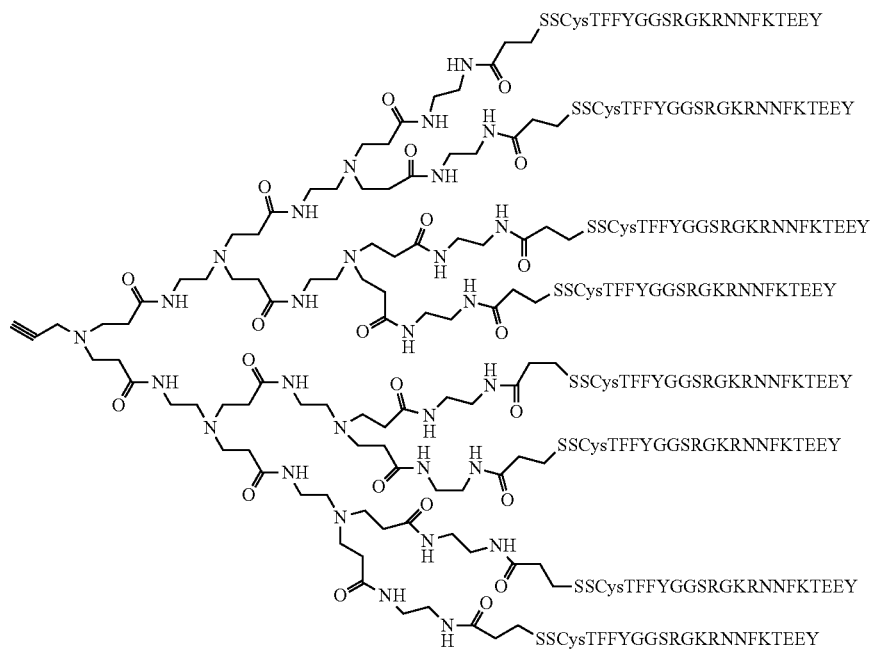

Example 15

Synthesis of Peptide Dendrimer Based on a Branched Lysine Core

A solid-phase approach was used to synthesize a dendrimer based on a branched lysine core. A Lys residue with both the α- and ε-amino groups blocked with the same labile protecting group (Fmoc) was coupled to a linker that was previously attached to resin (as shown in the schematic below). When deprotected, this Lys coupling was repeated once or twice so that either four or eight amino groups were available for further coupling reactions. Optionally three residues of Gly per chain can be added to provide a flexible link between the poly-Lysine core of the matrix and the peptides to be attached.

$H_2O$ and lyophilized. Crude peptides were purified by reversed phase-HPLC on a C4 column using a gradient of 20-80% B in 45 min, (Buffer A: $H_2O$/0.1% trifluoroacetic acid; Buffer B: 40% $CH_3CN$/60% $H_2O$/0.1% trifluoroacetic acid) with the eluant monitored at 229. Waters Acquity UPLC with Bruker Q-TOF mass spectroscopy detection confirmed the molecular mass and purity of the fractions collected, those displaying the correct purity and molecular mass of desired peptide were pooled and lyophilized.

In order to overcome contamination of the dendrimer mixture by byproducts containing amino acids side-chains protecting groups (Pbf group, Trt group, or tBu groups) the synthesis and deprotection steps were optimized so that the crude, lyophilized product was as homogeneous as possible. The use of fully protected Angiopep-2 fragments obtained from a 2-chlorotrityl chloride resin was also successful at achieving overall better quality products without deletions.

Synthesis and Cleavage of Poly-Lysines-AN2 Multimers Analogs

All of the peptides were assembled on rink amide methylbenzhydrylamine resin using manual solid-phase peptide synthesis with HCTU-(2-(6-chloro-1H-benzotriazole-1-yl)-1, 1,3,3-tetramethylaminium hexafluorophosphate) activation procedure for Fmoc (N-(9-fluorenyl)methoxycarbonyl) chemistry. Cleavage of peptides from the resin was achieved by treatment with trifluoroacetic acid, triisopropylsilane and water as scavengers (95:2:3 trifluoroacetic acid:triisopropylsilane:water). The reaction was allowed to proceed at room temperature (20-23° C.) for 2.0 h. The trifluoroacetic acid was then evaporated, and the peptide was precipitated with ice-cold ether, filtered, dissolved in 20% acetic acid/80%

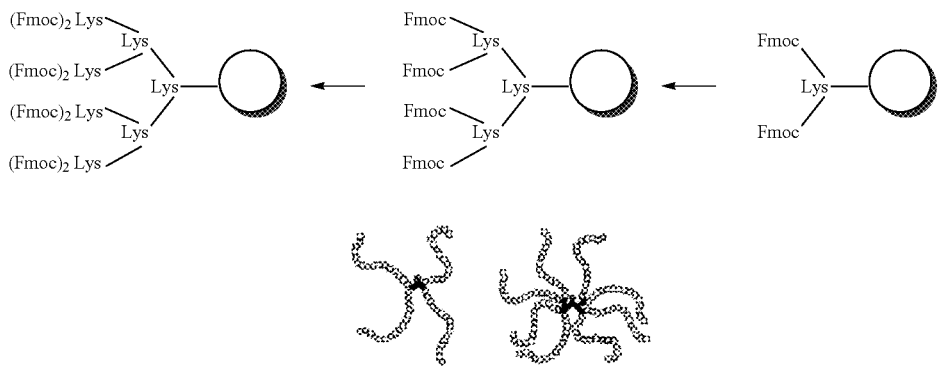

Alternatively, a pure peptide can be conjugated to a poly-Lysine core on a resin matrix for later purification. For example, cysteine containing Angiopep-2 was coupled to maleimide or SPDP activated poly-lysine resulting in a product with reduced byproduct contaminants. This was mainly because the Angiopep-2 monomers were purified before the conjugation step.

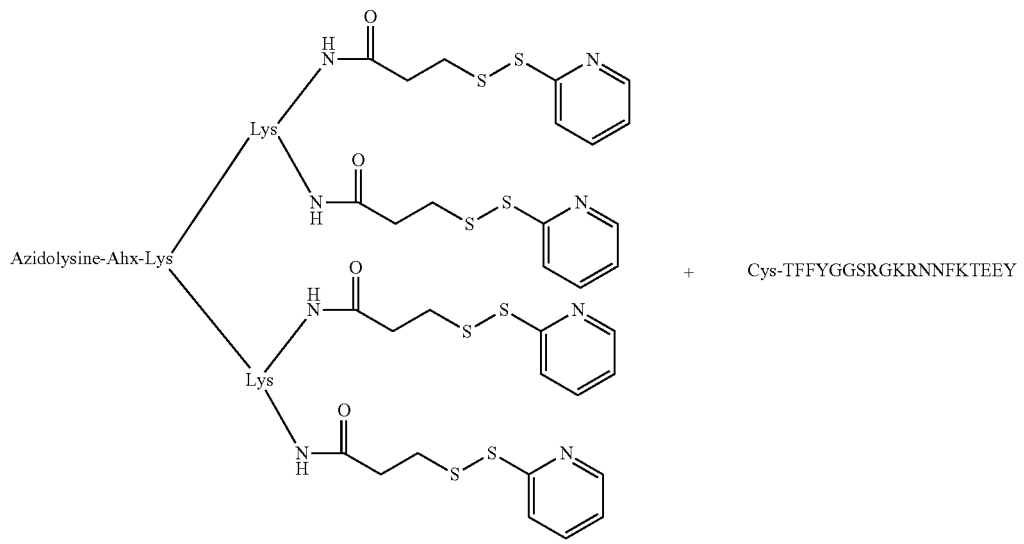
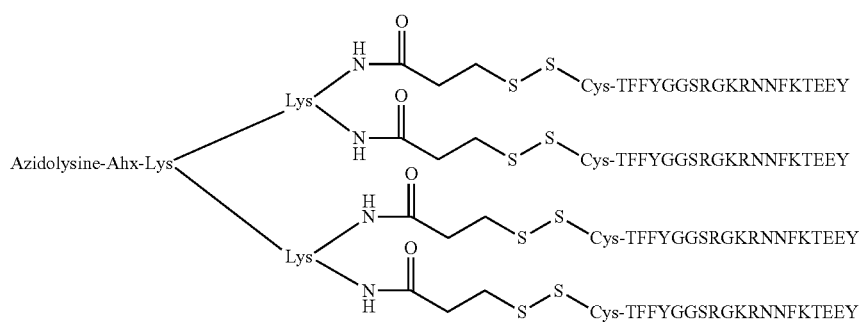
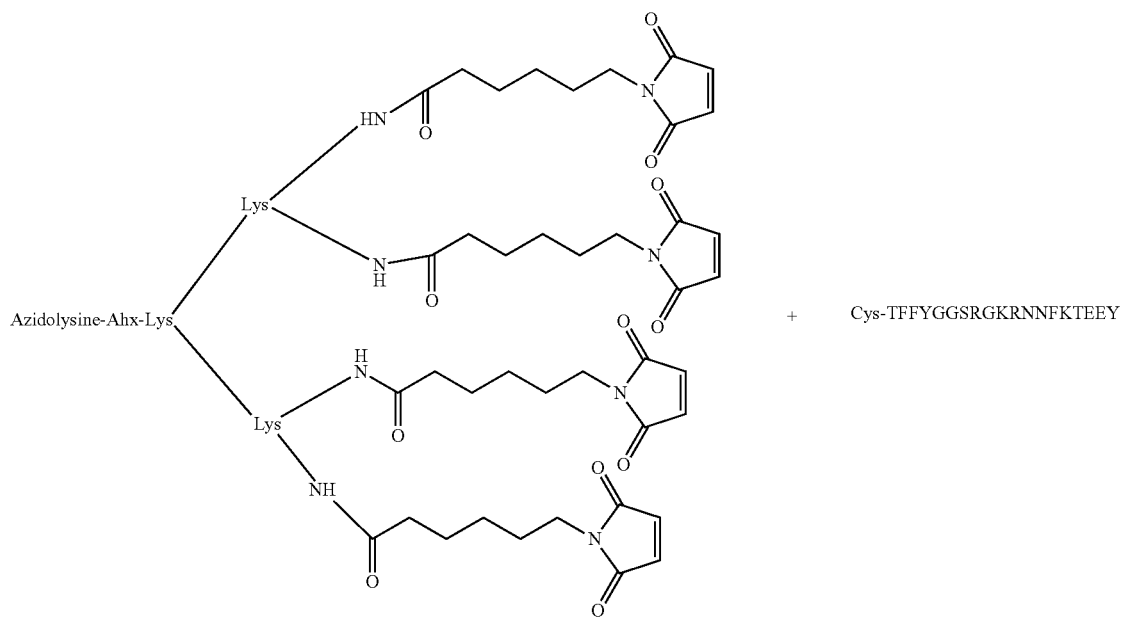

-continued

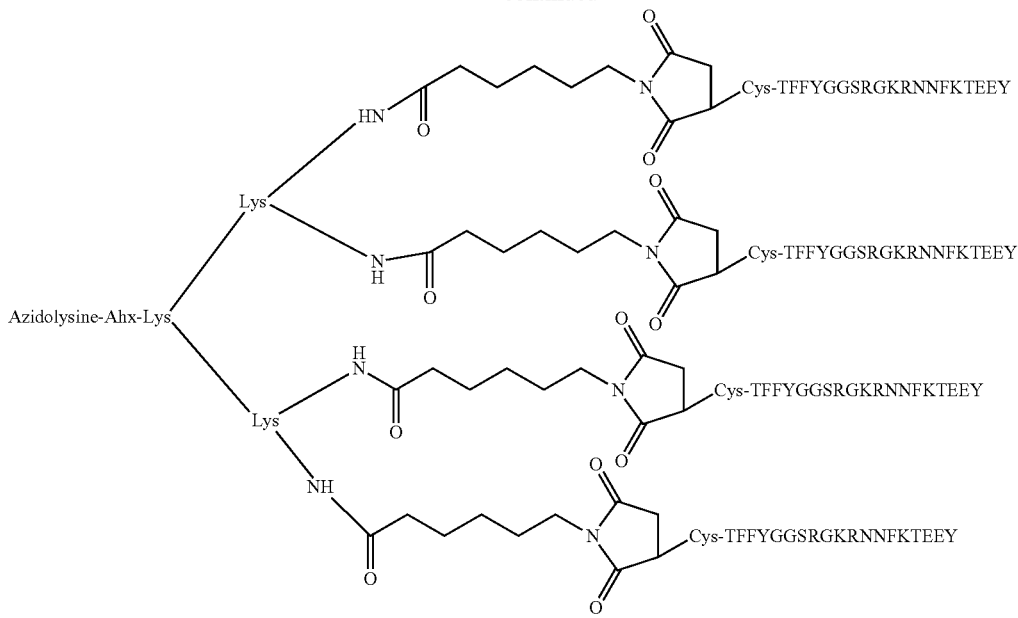

The invention claimed is:

1. A compound comprising the formula:

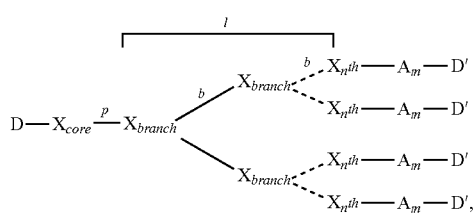

wherein

D is a first agent;

$X_{core}$ is a core moiety of a dendrimer with p number of branches, wherein p is an integer from 1 to 12;

$X_{branch}$ is a branch moiety of said dendrimer, wherein each $X_{branch}$ is attached to a branch of $X_{core}$ or to a branch of another $X_{branch}$, and wherein each $X_{branch}$ has b branches, and wherein b is an integer from 2 to 8;

l is the number of successive layers of $X_{branch}$ branches of said dendrimer and is an integer from 2 to 10;

$X_n^{th}$ is one of n surface branches of said dendrimer and is attached to a b branch of a $X_{branch}$ moiety, wherein $n=p(b)^l$, and wherein n is ≤512;

$A_m$ is a targeting peptide attached to an $X_n^{th}$ and comprises an amino acid sequence substantially identical to a sequence selected from the group consisting of SEQ ID NOs:1-105 and 107-117, or a functional fragment thereof;

m is a positive integer ≤n;

D' is a second agent that is optionally present, and either is attached to one or more $A_m$ or replaces one or more $A_m$ and is attached directly to one or more $X_n^{th}$, wherein the number of D' in said compound is ≤n;

the molecular weight of said dendrimer, excluding D, D' and $A_m$, is ≤500 kilodaltons; and wherein said first agent is attached to said dendrimer by a reactive group selected from a group consisting of a maleimide, a hydrazide, an azide, a haloacetamide, and an alkoxyamine.

2. The compound of claim 1, comprising the formula:

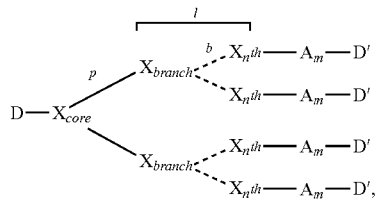

wherein
p is an integer between 2 and 6;
b is an integer from 2 to 4; and
l is an integer from 2 to 5.

3. The compound of claim 1, wherein said n is ≤128.

4. The compound of claim 1, wherein said molecular weight of said dendrimer is ≤100 kilodaltons.

5. The compound of claim 1, wherein said branch moiety is a derivative of any one of propargylamine, ethylenediamine, triethanolamine, pentaerythritol, propylamine, propyleneimine, azido-propyl(alkyl)amine, hydroxyethyl(alkyl)amine, tetraphenyl methane, trimesoylchloride, diamino hexane, diaminobutane, cystamine, propylenediamine, and lysine.

6. The compound of claim 1, wherein at least two said surface branches of said dendrimer has a targeting peptide attached.

7. The compound of claim 1, wherein said targeting peptide is attached to said surface branch via a linker.

8. The compound of claim 1, wherein at least one of said targeting peptides attached to said dendrimer comprises an amino acid sequence selected from the group consisting of Angiopep-1 (SEQ ID NO:67), Angiopep-2 (An$_2$) (SEQ ID NO:97), cys-Angiopep-2 (CysAn$_2$) (SEQ ID NO:113), Angiopep-2-cys (SEQ ID NO:114), and reversed Angiopep-2 (SEQ ID NO:117).

9. The compound of claim 1, wherein said dendrimer is attached to said reactive group by a linker.

10. The compound of claim 9, wherein said linker is selected from a group consisting of pyridinedisulfide, thiosulfonate, vinylsulfonate, isocyanate, NHS ester, imidoester, diazine, hydrazine, thiol, carboxylic acid, a multi-peptide linker, acetylene, and a covalent bond.

11. The compound of claim 1 comprising the formula:

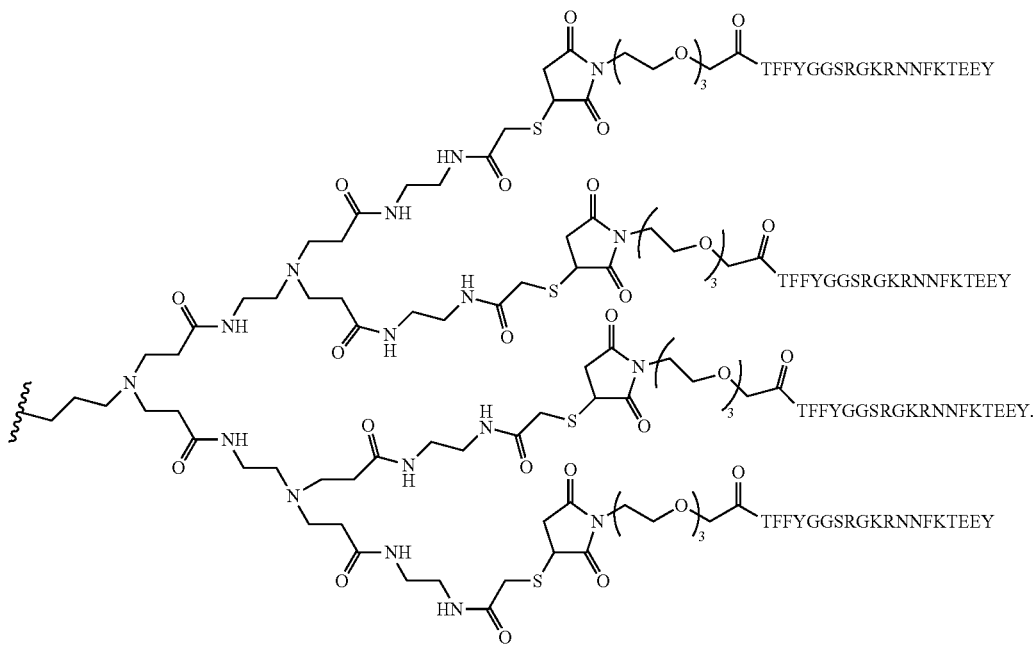

12. The compound of claim 1, wherein said first agent is selected from the group consisting of a protein, a small molecule, a nucleic acid, a diagnostic agent, an imaging agent, and a therapeutic agent.

13. A compound comprising the formula:

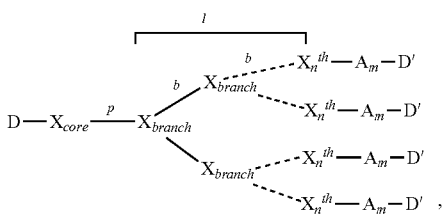

wherein
D is a first agent;
$X_{core}$ is a core moiety of a dendrimer with p number of branches, wherein p is an integer from 1 to 12;

$X_{branch}$ is a branch moiety of said dendrimer, wherein each $X_{branch}$ is attached to a branch of $X_{core}$ or to a branch of another $X_{branch}$, and wherein each $X_{branch}$ has b branches, and wherein b is an integer from 2 to 8;

l is the number of successive layers of $X_{branch}$ branches of said dendrimer and is an integer from 2 to 10;

$X_n^{th}$ is one of n surface branches of said dendrimer and is attached to a b branch of a $X_{branch}$ moiety, wherein $n=p(b)^l$, and wherein n is $\leq 512$;

$A_m$ is a targeting peptide attached to an $X_n^{th}$ and comprises an amino acid sequence substantially identical to a sequence selected from the group consisting of SEQ ID NOs:1-105 and 107-117, or a functional fragment thereof;

m is a positive integer $\leq n$;

D' is a second agent that is optionally present, and either is attached to one or more $A_m$ or replaces one or more $A_m$ and is attached directly to one or more $X_n^{th}$, wherein the number of D' in said compound is $\leq n$;

the molecular weight of said dendrimer, excluding D, D' and $A_m$, is $\leq 500$ kilodaltons; and the compound comprises the formula:

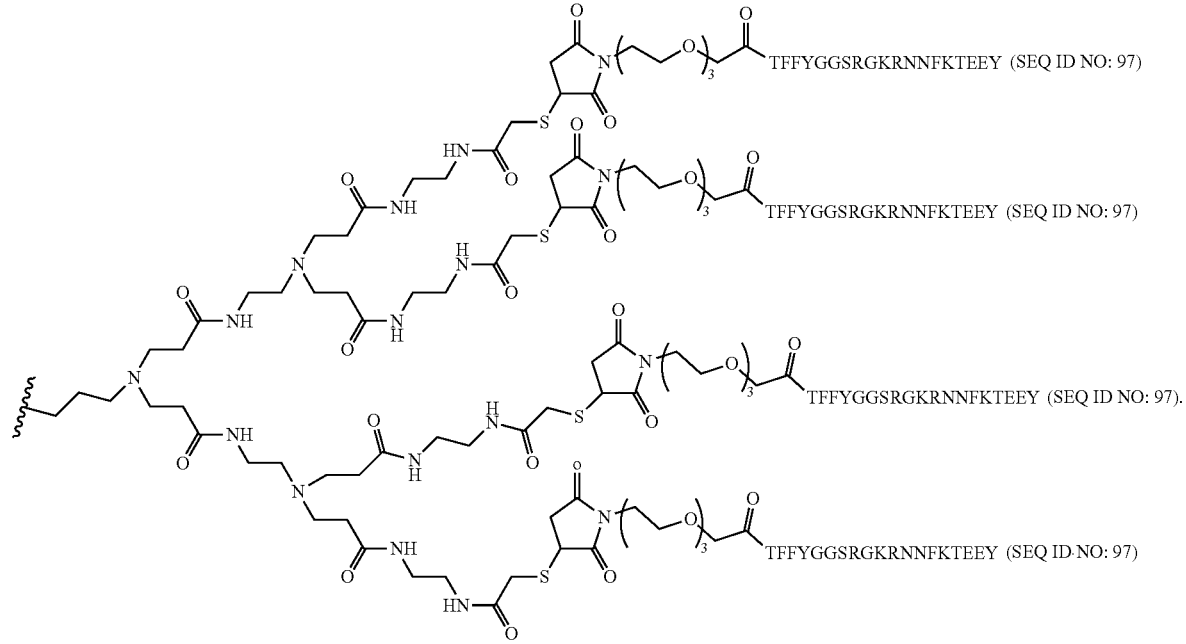

14. The compound of claim 13, wherein said first agent is attached to said dendrimer by a reactive group.

15. The compound of claim 14, wherein said reactive group is selected from a group consisting of a maleimide, a hydrazine, an azide, a haloacetamide, and an alkoxyamine.

16. The compound of claim 15, wherein said reactive group is an azide.

17. The compound of claim 13, wherein said dendrimer is attached to said reactive group by a linker.

18. The compound of claim 17, wherein said linker is selected from a group consisting of pyridinedisulfide, thiosulfonate, vinylsulfonate, isocyanate, NHS ester, imidoester, diazine, hydrazine, thiol, carboxylic acid, a multi-peptide linker, acetylene, and a covalent bond.

19. The compound of claim 13, wherein said first agent is selected from the group consisting of a protein, a small molecule, a nucleic acid, a diagnostic agent, an imaging agent, and a therapeutic agent.

* * * * *

SEQUENCE LISTING

<160> NUMBER OF SEQ ID NOS: 122

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Phe Val Tyr Gly Gly Cys Arg Ala Lys Arg Asn Asn Phe Lys Ser
1               5                   10                  15

Ala Glu Asp

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Phe Gln Tyr Gly Gly Cys Met Gly Asn Gly Asn Asn Phe Val Thr
1               5                   10                  15

Glu Lys Glu

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Phe Phe Tyr Gly Gly Cys Gly Gly Asn Arg Asn Asn Phe Asp Thr

```
Glu Glu Tyr

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Phe Tyr Tyr Gly Gly Cys Leu Gly Asn Lys Asn Asn Tyr Leu Arg
1               5                   10                  15

Glu Glu Glu

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Phe Phe Tyr Gly Gly Cys Arg Ala Lys Arg Asn Asn Phe Lys Arg
1               5                   10                  15

Ala Lys Tyr

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Phe Phe Tyr Gly Gly Cys Arg Gly Lys Arg Asn Asn Phe Lys Arg
1               5                   10                  15

Ala Lys Tyr

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Phe Phe Tyr Gly Gly Cys Arg Ala Lys Lys Asn Asn Tyr Lys Arg
1               5                   10                  15

Ala Lys Tyr

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

Thr Phe Phe Tyr Gly Gly Cys Arg Gly Lys Lys Asn Asn Phe Lys Arg
1               5                   10                  15

Ala Lys Tyr

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Phe Gln Tyr Gly Gly Cys Arg Ala Lys Arg Asn Asn Phe Lys Arg
1               5                   10                  15

Ala Lys Tyr

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Phe Gln Tyr Gly Gly Cys Arg Gly Lys Lys Asn Asn Phe Lys Arg
1               5                   10                  15

Ala Lys Tyr

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Phe Phe Tyr Gly Gly Cys Leu Gly Lys Arg Asn Asn Phe Lys Arg
1               5                   10                  15

Ala Lys Tyr

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Phe Phe Tyr Gly Gly Ser Leu Gly Lys Arg Asn Asn Phe Lys Arg
1               5                   10                  15

Ala Lys Tyr

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Pro Phe Phe Tyr Gly Gly Cys Gly Gly Lys Lys Asn Asn Phe Lys Arg
1               5                   10                  15

Ala Lys Tyr

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Phe Phe Tyr Gly Gly Cys Arg Gly Lys Gly Asn Asn Tyr Lys Arg
1               5                   10                  15

Ala Lys Tyr

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Phe Phe Tyr Gly Gly Cys Arg Gly Lys Arg Asn Asn Phe Leu Arg
1               5                   10                  15

Ala Lys Tyr

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Phe Phe Tyr Gly Gly Cys Arg Gly Lys Arg Asn Asn Phe Lys Arg
1               5                   10                  15

Glu Lys Tyr

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Phe Phe Tyr Gly Gly Cys Arg Ala Lys Lys Asn Asn Phe Lys Arg
1               5                   10                  15

Ala Lys Glu

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 18

Thr Phe Phe Tyr Gly Gly Cys Arg Gly Lys Arg Asn Asn Phe Lys Arg
1               5                   10                  15

Ala Lys Asp

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Phe Phe Tyr Gly Gly Cys Arg Ala Lys Arg Asn Asn Phe Asp Arg
1               5                   10                  15

Ala Lys Tyr

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Phe Phe Tyr Gly Gly Cys Arg Gly Lys Lys Asn Asn Phe Lys Arg
1               5                   10                  15

Ala Glu Tyr

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Phe Phe Tyr Gly Gly Cys Gly Ala Asn Arg Asn Asn Phe Lys Arg
1               5                   10                  15

Ala Lys Tyr

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Phe Phe Tyr Gly Gly Cys Gly Gly Lys Lys Asn Asn Phe Lys Thr
1               5                   10                  15

Ala Lys Tyr

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 23

Thr Phe Phe Tyr Gly Gly Cys Arg Gly Asn Arg Asn Asn Phe Leu Arg
1               5                   10                  15

Ala Lys Tyr

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Phe Phe Tyr Gly Gly Cys Arg Gly Asn Arg Asn Asn Phe Lys Thr
1               5                   10                  15

Ala Lys Tyr

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Phe Phe Tyr Gly Gly Ser Arg Gly Asn Arg Asn Asn Phe Lys Thr
1               5                   10                  15

Ala Lys Tyr

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Phe Phe Tyr Gly Gly Cys Leu Gly Asn Gly Asn Asn Phe Lys Arg
1               5                   10                  15

Ala Lys Tyr

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Phe Phe Tyr Gly Gly Cys Leu Gly Asn Arg Asn Asn Phe Leu Arg
1               5                   10                  15

Ala Lys Tyr

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 28

Thr Phe Phe Tyr Gly Gly Cys Leu Gly Asn Arg Asn Asn Phe Lys Thr
1               5                   10                  15

Ala Lys Tyr

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Phe Phe Tyr Gly Gly Cys Arg Gly Asn Gly Asn Asn Phe Lys Ser
1               5                   10                  15

Ala Lys Tyr

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Phe Phe Tyr Gly Gly Cys Arg Gly Lys Lys Asn Asn Phe Asp Arg
1               5                   10                  15

Glu Lys Tyr

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Phe Phe Tyr Gly Gly Cys Arg Gly Lys Arg Asn Asn Phe Leu Arg
1               5                   10                  15

Glu Lys Glu

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Phe Phe Tyr Gly Gly Cys Arg Gly Lys Gly Asn Asn Phe Asp Arg
1               5                   10                  15

Ala Lys Tyr

<210> SEQ ID NO 33
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 33

Thr Phe Phe Tyr Gly Gly Ser Arg Gly Lys Gly Asn Asn Phe Asp Arg
1               5                   10                  15

Ala Lys Tyr

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Phe Phe Tyr Gly Gly Cys Arg Gly Asn Gly Asn Asn Phe Val Thr
1               5                   10                  15

Ala Lys Tyr

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Phe Phe Tyr Gly Gly Cys Gly Gly Lys Gly Asn Asn Tyr Val Thr
1               5                   10                  15

Ala Lys Tyr

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Phe Phe Tyr Gly Gly Cys Leu Gly Lys Gly Asn Asn Phe Leu Thr
1               5                   10                  15

Ala Lys Tyr

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Phe Phe Tyr Gly Gly Cys Leu Gly Asn Lys Asn Asn Phe Leu Thr
1               5                   10                  15

Ala Lys Tyr

<210> SEQ ID NO 38
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 38

Thr Phe Phe Tyr Gly Gly Cys Gly Gly Asn Lys Asn Asn Phe Val Arg
1               5                   10                  15

Glu Lys Tyr

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Phe Phe Tyr Gly Gly Cys Met Gly Asn Lys Asn Asn Phe Val Arg
1               5                   10                  15

Glu Lys Tyr

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Phe Phe Tyr Gly Gly Ser Met Gly Asn Lys Asn Asn Phe Val Arg
1               5                   10                  15

Glu Lys Tyr

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Phe Phe Tyr Gly Gly Cys Leu Gly Asn Arg Asn Asn Tyr Val Arg
1               5                   10                  15

Glu Lys Tyr

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Phe Phe Tyr Gly Gly Cys Leu Gly Asn Arg Asn Asn Phe Val Arg
1               5                   10                  15

Glu Lys Tyr

<210> SEQ ID NO 43
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 43

Thr Phe Phe Tyr Gly Gly Cys Leu Gly Asn Lys Asn Asn Tyr Val Arg
1               5                   10                  15

Glu Lys Tyr

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Phe Phe Tyr Gly Gly Cys Gly Gly Asn Gly Asn Asn Phe Leu Thr
1               5                   10                  15

Ala Lys Tyr

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Phe Phe Tyr Gly Gly Cys Arg Gly Asn Arg Asn Asn Phe Leu Thr
1               5                   10                  15

Ala Glu Tyr

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Phe Phe Tyr Gly Gly Cys Arg Gly Asn Gly Asn Asn Phe Lys Ser
1               5                   10                  15

Ala Glu Tyr

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Phe Phe Tyr Gly Gly Cys Leu Gly Asn Lys Asn Asn Phe Lys Thr
1               5                   10                  15

Ala Glu Tyr

<210> SEQ ID NO 48
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Phe Phe Tyr Gly Gly Cys Arg Gly Asn Arg Asn Asn Phe Lys Thr
1               5                   10                  15

Glu Glu Tyr

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Phe Phe Tyr Gly Gly Cys Arg Gly Lys Arg Asn Asn Phe Lys Thr
1               5                   10                  15

Glu Glu Asp

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Phe Phe Tyr Gly Gly Cys Gly Gly Asn Gly Asn Asn Phe Val Arg
1               5                   10                  15

Glu Lys Tyr

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Phe Phe Tyr Gly Gly Cys Met Gly Asn Gly Asn Asn Phe Val Arg
1               5                   10                  15

Glu Lys Tyr

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Phe Phe Tyr Gly Gly Cys Gly Gly Asn Gly Asn Asn Phe Leu Arg
1               5                   10                  15

Glu Lys Tyr

<210> SEQ ID NO 53
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Phe Phe Tyr Gly Gly Cys Leu Gly Asn Gly Asn Asn Phe Val Arg
1               5                   10                  15

Glu Lys Tyr

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Phe Phe Tyr Gly Gly Cys Leu Gly Asn Gly Asn Asn Tyr Leu Arg
1               5                   10                  15

Glu Lys Tyr

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Phe Phe Tyr Gly Gly Ser Leu Gly Asn Gly Asn Asn Phe Val Arg
1               5                   10                  15

Glu Lys Tyr

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Phe Phe Tyr Gly Gly Cys Arg Gly Asn Gly Asn Asn Phe Val Thr
1               5                   10                  15

Ala Glu Tyr

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Phe Phe Tyr Gly Gly Cys Leu Gly Lys Gly Asn Asn Phe Val Ser
1               5                   10                  15

Ala Glu Tyr
```

```
<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Phe Phe Tyr Gly Gly Cys Leu Gly Asn Arg Asn Asn Phe Asp Arg
1               5                   10                  15

Ala Glu Tyr

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Phe Phe Tyr Gly Gly Cys Leu Gly Asn Arg Asn Asn Phe Leu Arg
1               5                   10                  15

Glu Glu Tyr

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Phe Phe Tyr Gly Gly Cys Leu Gly Asn Lys Asn Asn Tyr Leu Arg
1               5                   10                  15

Glu Glu Tyr

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Phe Phe Tyr Gly Gly Cys Gly Gly Asn Arg Asn Asn Tyr Leu Arg
1               5                   10                  15

Glu Glu Tyr

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Phe Phe Tyr Gly Gly Ser Gly Gly Asn Arg Asn Asn Tyr Leu Arg
1               5                   10                  15

Glu Glu Tyr
```

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Arg Pro Asp Phe Cys Leu Glu Pro Pro Tyr Thr Gly Pro Cys Val
1               5                   10                  15

Ala Arg Ile

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Arg Ile Ile Arg Tyr Phe Tyr Asn Ala Lys Ala Gly Leu Cys Gln
1               5                   10                  15

Thr Phe Val Tyr Gly
            20

<210> SEQ ID NO 65
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Gly Gly Cys Arg Ala Lys Arg Asn Asn Tyr Lys Ser Ala Glu Asp
1               5                   10                  15

Cys Met Arg Thr Cys Gly
            20

<210> SEQ ID NO 66
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Asp Phe Cys Leu Glu Pro Pro Tyr Thr Gly Pro Cys Val Ala Arg
1               5                   10                  15

Ile Ile Arg Tyr Phe Tyr
            20

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Phe Phe Tyr Gly Gly Cys Arg Gly Lys Arg Asn Asn Phe Lys Thr

<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Lys Phe Phe Tyr Gly Gly Cys Arg Gly Lys Arg Asn Asn Phe Lys Thr
1               5                   10                  15

Glu Glu Tyr

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Thr Phe Tyr Tyr Gly Gly Cys Arg Gly Lys Arg Asn Asn Tyr Lys Thr
1               5                   10                  15

Glu Glu Tyr

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Thr Phe Phe Tyr Gly Gly Ser Arg Gly Lys Arg Asn Asn Phe Lys Thr
1               5                   10                  15

Glu Glu Tyr

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Cys Thr Phe Phe Tyr Gly Cys Cys Arg Gly Lys Arg Asn Asn Phe Lys
1               5                   10                  15

Thr Glu Glu Tyr
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Thr Phe Phe Tyr Gly Gly Cys Arg Gly Lys Arg Asn Asn Phe Lys Thr
1               5                   10                  15

Glu Glu Tyr Cys
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Thr Phe Phe Tyr Gly Ser Cys Arg Gly Lys Arg Asn Asn Phe Lys
1               5                   10                  15

Thr Glu Glu Tyr
            20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 75
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Phe Phe Tyr Gly Gly Cys Arg Gly Lys Arg Asn Asn Phe Lys Thr
1               5                   10                  15

Glu Glu Tyr

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Phe Phe Tyr Gly Gly Cys Arg Gly Lys Arg Asn Asn Phe Lys Thr
1               5                   10                  15

Lys Glu Tyr

<210> SEQ ID NO 77
<211> LENGTH: 19
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 77

Thr Phe Phe Tyr Gly Gly Lys Arg Gly Lys Arg Asn Asn Phe Lys Thr
1               5                   10                  15

Glu Glu Tyr

<210> SEQ ID NO 78
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Phe Phe Tyr Gly Gly Cys Arg Gly Lys Arg Asn Asn Phe Lys Thr
1               5                   10                  15

Lys Arg Tyr

<210> SEQ ID NO 79
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Phe Phe Tyr Gly Gly Lys Arg Gly Lys Arg Asn Asn Phe Lys Thr
1               5                   10                  15

Ala Glu Tyr

<210> SEQ ID NO 80
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Phe Phe Tyr Gly Gly Lys Arg Gly Lys Arg Asn Asn Phe Lys Thr
1               5                   10                  15

Ala Gly Tyr

<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Phe Phe Tyr Gly Gly Lys Arg Gly Lys Arg Asn Asn Phe Lys Arg
1               5                   10                  15

Glu Lys Tyr

<210> SEQ ID NO 82
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 82

Thr Phe Phe Tyr Gly Gly Lys Arg Gly Lys Arg Asn Asn Phe Lys Arg
1               5                   10                  15

Ala Lys Tyr

<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Phe Phe Tyr Gly Gly Cys Leu Gly Asn Arg Asn Asn Phe Lys Thr
1               5                   10                  15

Glu Glu Tyr

<210> SEQ ID NO 84
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Phe Phe Tyr Gly Cys Gly Arg Gly Lys Arg Asn Asn Phe Lys Thr
1               5                   10                  15

Glu Glu Tyr

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Phe Phe Tyr Gly Gly Arg Cys Gly Lys Arg Asn Asn Phe Lys Thr
1               5                   10                  15

Glu Glu Tyr

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Phe Phe Tyr Gly Gly Cys Leu Gly Asn Gly Asn Asn Phe Asp Thr
1               5                   10                  15

Glu Glu Glu

<210> SEQ ID NO 87
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 87

Thr Phe Gln Tyr Gly Gly Cys Arg Gly Lys Arg Asn Asn Phe Lys Thr
1               5                   10                  15

Glu Glu Tyr

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Tyr Asn Lys Glu Phe Gly Thr Phe Asn Thr Lys Gly Cys Glu Arg Gly
1               5                   10                  15

Tyr Arg Phe

<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Phe Lys Tyr Gly Gly Cys Leu Gly Asn Met Asn Asn Phe Glu Thr
1               5                   10                  15

Leu Glu Glu

<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Phe Lys Tyr Gly Gly Cys Leu Gly Asn Lys Asn Asn Phe Leu Arg
1               5                   10                  15

Leu Lys Tyr

<210> SEQ ID NO 91
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Phe Lys Tyr Gly Gly Cys Leu Gly Asn Lys Asn Asn Tyr Leu Arg
1               5                   10                  15

Leu Lys Tyr

<210> SEQ ID NO 92
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Thr Lys Arg Lys Arg Lys Lys Gln Arg Val Lys Ile Ala Tyr Glu
1               5                   10                  15

Glu Ile Phe Lys Asn Tyr
            20

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Thr Lys Arg Lys Arg Lys Lys Gln Arg Val Lys Ile Ala Tyr
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Gly Gly Arg Leu Ser Tyr Ser Arg Arg Phe Ser Thr Ser Thr Gly
1               5                   10                  15

Arg

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Arg Leu Ser Tyr Ser Arg Arg Arg Phe
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Gln Ile Lys Ile Trp Phe Gln Asn Arg Arg Met Lys Trp Lys Lys
1               5                   10                  15

<210> SEQ ID NO 97
<211> LENGTH: 19
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 97

Thr Phe Phe Tyr Gly Gly Ser Arg Gly Lys Arg Asn Asn Phe Lys Thr
1               5                   10                  15

Glu Glu Tyr

<210> SEQ ID NO 98
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Arg Pro Asp Phe Cys Leu Glu Pro Pro Tyr Thr Gly Pro Cys Val
1               5                   10                  15

Ala Arg Ile Ile Arg Tyr Phe Tyr Asn Ala Lys Ala Gly Leu Cys Gln
            20                  25                  30

Thr Phe Val Tyr Gly Gly Cys Arg Ala Lys Arg Asn Asn Phe Lys Ser
        35                  40                  45

Ala Glu Asp Cys Met Arg Thr Cys Gly Gly Ala
    50                  55

<210> SEQ ID NO 99
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Phe Phe Tyr Gly Gly Cys Arg Gly Lys Arg Asn Asn Phe Lys Thr
1               5                   10                  15

Lys Glu Tyr

<210> SEQ ID NO 100
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Phe Lys Tyr Gly Gly Cys Leu Gly Asn Lys Asn Asn Tyr Leu Arg
1               5                   10                  15

Leu Lys Tyr

<210> SEQ ID NO 101
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Phe Phe Tyr Gly Gly Cys Arg Ala Lys Arg Asn Asn Phe Lys Arg
1               5                   10                  15

Ala Lys Tyr

<210> SEQ ID NO 102
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asn Ala Lys Ala Gly Leu Cys Gln Thr Phe Val Tyr Gly Gly Cys Leu
1               5                   10                  15

Ala Lys Arg Asn Asn Phe Glu Ser Ala Glu Asp Cys Met Arg Thr Cys
            20                  25                  30

Gly Gly Ala
        35

<210> SEQ ID NO 103
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Gly Gly Cys Arg Ala Lys Arg Asn Asn Phe Lys Ser Ala Glu Asp
1               5                   10                  15

Cys Met Arg Thr Cys Gly Gly Ala
            20

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Leu Cys Gln Thr Phe Val Tyr Gly Gly Cys Arg Ala Lys Arg Asn
1               5                   10                  15

Asn Phe Lys Ser Ala Glu
            20

<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Cys Gln Thr Phe Val Tyr Gly Gly Cys Glu Ala Lys Arg Asn Asn
1               5                   10                  15

Phe Lys Ser Ala
            20

<210> SEQ ID NO 106
<211> LENGTH: 180
<212> TYPE: DNA
<213> ORGANISM: Artificial Sequence
<220> FEATURE:
<223> OTHER INFORMATION: Description of Artificial Sequence: Synthetic construct

<400> SEQUENCE: 106

```
atgagaccag atttctgcct cgagccgccg tacactgggc cctgcaaagc tcgtatcatc    60
cgttacttct acaatgcaaa ggcaggcctg tgtcagacct tcgtatacgg cggctgcaga   120
gctaagcgta caacttcaa atccgcggaa gactgcatgc gtacttgcgg tggtgcttag   180
```

<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Thr Phe Phe Tyr Gly Gly Ser Arg Gly Lys Arg Asn Asn Phe Lys Thr
1               5                   10                  15

Glu Glu Tyr
```

<210> SEQ ID NO 108
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Arg Phe Phe Tyr Gly Gly Ser Arg Gly Lys Arg Asn Asn Phe Lys Thr
1               5                   10                  15

Glu Glu Tyr
```

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

```
Arg Phe Phe Tyr Gly Gly Ser Arg Gly Lys Arg Asn Asn Phe Lys Thr
1               5                   10                  15

Glu Glu Tyr
```

<210> SEQ ID NO 110
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

```
Arg Phe Phe Tyr Gly Gly Ser Arg Gly Lys Arg Asn Asn Phe Arg Thr
1               5                   10                  15

Glu Glu Tyr
```

<210> SEQ ID NO 111
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 111

Thr Phe Phe Tyr Gly Gly Ser Arg Gly Lys Arg Asn Asn Phe Arg Thr
1               5                   10                  15

Glu Glu Tyr

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Phe Phe Tyr Gly Gly Ser Arg Gly Arg Arg Asn Asn Phe Arg Thr
1               5                   10                  15

Glu Glu Tyr

<210> SEQ ID NO 113
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Thr Phe Phe Tyr Gly Gly Ser Arg Gly Lys Arg Asn Asn Phe Lys
1               5                   10                  15

Thr Glu Glu Tyr
            20

<210> SEQ ID NO 114
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Thr Phe Phe Tyr Gly Gly Ser Arg Gly Arg Arg Asn Asn Phe Arg
1               5                   10                  15

Thr Glu Glu Tyr
            20
```

```
<210> SEQ ID NO 116
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Phe Phe Tyr Gly Gly Ser Arg Gly Arg Arg Asn Asn Phe Arg Thr
1               5                   10                  15

Glu Glu Tyr Cys
            20

<210> SEQ ID NO 117
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Tyr Glu Glu Thr Lys Phe Asn Asn Arg Lys Gly Arg Ser Gly Gly Tyr
1               5                   10                  15

Phe Phe Thr

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (3)..(3)
<223> OTHER INFORMATION: Xaa is Asn or Gln
<220> FEATURE:
<221> NAME/KEY: MISC_FEATURE
<222> LOCATION: (4)..(4)
<223> OTHER INFORMATION: Xaa is Asn or Gln
<220> FEATURE:
<221> NAME/KEY: MISC_FEATURE
<222> LOCATION: (5)..(5)
<223> OTHER INFORMATION: Xaa is Phe, Tyr, or Trp

<400> SEQUENCE: 118

Lys Arg Xaa Xaa Xaa Lys
1               5

<210> SEQ ID NO 119
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: Xaa is Cys or absent
<220> FEATURE:
<221> NAME/KEY: MISC_FEATURE
<222> LOCATION: (2)..(2)
<223> OTHER INFORMATION: Xaa is Cys, Thr, or absent
<220> FEATURE:
<221> NAME/KEY: MISC_FEATURE
<222> LOCATION: (3)..(4)
<223> OTHER INFORMATION: Xaa is Cys, Phe, or absent
<220> FEATURE:
```

```
<221> NAME/KEY: MISC_FEATURE
<222> LOCATION: (5)..(5)
<223> OTHER INFORMATION: Xaa is Cys, Tyr, or absent
<220> FEATURE:
<221> NAME/KEY: MISC_FEATURE
<222> LOCATION: (6)..(7)
<223> OTHER INFORMATION: Xaa is Cys, Gly, or absent
<220> FEATURE:
<221> NAME/KEY: MISC_FEATURE
<222> LOCATION: (8)..(8)
<223> OTHER INFORMATION: Xaa is Cys, Ser, or absent
<220> FEATURE:
<221> NAME/KEY: MISC_FEATURE
<222> LOCATION: (9)..(9)
<223> OTHER INFORMATION: Xaa is Cys, Arg, or absent
<220> FEATURE:
<221> NAME/KEY: MISC_FEATURE
<222> LOCATION: (10)..(10)
<223> OTHER INFORMATION: Xaa is Cys, Gly, or absent
<220> FEATURE:
<221> NAME/KEY: MISC_FEATURE
<222> LOCATION: (13)..(13)
<223> OTHER INFORMATION: Xaa is Asn or Gln
<220> FEATURE:
<221> NAME/KEY: MISC_FEATURE
<222> LOCATION: (14)..(14)
<223> OTHER INFORMATION: Xaa is Asn or Gln
<220> FEATURE:
<221> NAME/KEY: MISC_FEATURE
<222> LOCATION: (15)..(15)
<223> OTHER INFORMATION: Xaa is Phe, Tyr, or Trp
<220> FEATURE:
<221> NAME/KEY: MISC_FEATURE
<222> LOCATION: (17)..(17)
<223> OTHER INFORMATION: Xaa is Cys, Tyr, Thr, or absent
<220> FEATURE:
<221> NAME/KEY: MISC_FEATURE
<222> LOCATION: (18)..(18)
<223> OTHER INFORMATION: Xaa is Cys, Tyr, Glu, or absent
<220> FEATURE:
<221> NAME/KEY: MISC_FEATURE
<222> LOCATION: (19)..(19)
<223> OTHER INFORMATION: Xaa is Glu or absent
<220> FEATURE:
<221> NAME/KEY: MISC_FEATURE
<222> LOCATION: (20)..(20)
<223> OTHER INFORMATION: Xaa is Tyr or absent
<220> FEATURE:
<221> NAME/KEY: MISC_FEATURE
<222> LOCATION: (21)..(21)
<223> OTHER INFORMATION: Xaa is Cys or absent

<400> SEQUENCE: 119

Xaa Xaa Xaa Xaa Xaa Xaa Xaa Xaa Xaa Xaa Lys Arg Xaa Xaa Xaa Lys
1               5                   10                  15

Xaa Xaa Xaa Xaa Xaa
            20

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: Xaa is Lys or D-Lys
<220> FEATURE:
<221> NAME/KEY: MISC_FEATURE
<222> LOCATION: (2)..(2)
<223> OTHER INFORMATION: Xaa is Arg or D-Arg
<220> FEATURE:
<221> NAME/KEY: MISC_FEATURE
<222> LOCATION: (5)..(5)
```

```
<223> OTHER INFORMATION: Xaa is Phe or D-Phe
<220> FEATURE:
<221> NAME/KEY: MISC_FEATURE
<222> LOCATION: (6)..(6)
<223> OTHER INFORMATION: Xaa is Lys or D-Lys

<400> SEQUENCE: 120

Xaa Xaa Asn Asn Xaa Xaa
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: Xaa is Lys or D-Lys
<220> FEATURE:
<221> NAME/KEY: MISC_FEATURE
<222> LOCATION: (2)..(2)
<223> OTHER INFORMATION: Xaa is Arg or D-Arg
<220> FEATURE:
<221> NAME/KEY: MISC_FEATURE
<222> LOCATION: (5)..(5)
<223> OTHER INFORMATION: Xaa is Phe or D-Phe
<220> FEATURE:
<221> NAME/KEY: MISC_FEATURE
<222> LOCATION: (6)..(6)
<223> OTHER INFORMATION: Xaa is Lys or D-Lys
<220> FEATURE:
<221> NAME/KEY: MISC_FEATURE
<222> LOCATION: (7)..(7)
<223> OTHER INFORMATION: Xaa is Tyr or D-Try

<400> SEQUENCE: 121

Xaa Xaa Asn Asn Xaa Xaa Xaa
1               5

<210> SEQ ID NO 122
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys or absent
<220> FEATURE:
<221> NAME/KEY: MISC_FEATURE
<222> LOCATION: (2)..(2)
<223> OTHER INFORMATION: Xaa is Cys, Thr, or absent
<220> FEATURE:
<221> NAME/KEY: MISC_FEATURE
<222> LOCATION: (3)..(4)
<223> OTHER INFORMATION: Xaa is Cys, Phe, or absent
<220> FEATURE:
<221> NAME/KEY: MISC_FEATURE
<222> LOCATION: (5)..(5)
<223> OTHER INFORMATION: Xaa is Cys, Tyr, or absent
<220> FEATURE:
<221> NAME/KEY: MISC_FEATURE
<222> LOCATION: (6)..(7)
<223> OTHER INFORMATION: Xaa is Cys, Gly, or absent
<220> FEATURE:
<221> NAME/KEY: MISC_FEATURE
<222> LOCATION: (8)..(8)
<223> OTHER INFORMATION: Xaa is Cys, Ser, or absent
<220> FEATURE:
<221> NAME/KEY: MISC_FEATURE
<222> LOCATION: (9)..(9)
```

-continued

<223> OTHER INFORMATION: Xaa is Cys, Arg, or absent
<220> FEATURE:
<221> NAME/KEY: MISC_FEATURE
<222> LOCATION: (10)..(10)
<223> OTHER INFORMATION: Xaa is Cys, Gly, or absent
<220> FEATURE:
<221> NAME/KEY: MISC_FEATURE
<222> LOCATION: (11)..(11)
<223> OTHER INFORMATION: Xaa is Lys or D-Lys
<220> FEATURE:
<221> NAME/KEY: MISC_FEATURE
<222> LOCATION: (12)..(12)
<223> OTHER INFORMATION: Xaa is Arg or D-Arg
<220> FEATURE:
<221> NAME/KEY: MISC_FEATURE
<222> LOCATION: (15)..(15)
<223> OTHER INFORMATION: Xaa is Phe or D-Phe
<220> FEATURE:
<221> NAME/KEY: MOD_RES
<222> LOCATION: (16)..(16)
<223> OTHER INFORMATION: Xaa is Lys or D-Lys
<220> FEATURE:
<221> NAME/KEY: MISC_FEATURE
<222> LOCATION: (17)..(17)
<223> OTHER INFORMATION: Xaa is Tyr or D-Tyr
<220> FEATURE:
<221> NAME/KEY: MISC_FEATURE
<222> LOCATION: (18)..(18)
<223> OTHER INFORMATION: Xaa is Cys, Tyr, Thr, or absent
<220> FEATURE:
<221> NAME/KEY: MISC_FEATURE
<222> LOCATION: (19)..(19)
<223> OTHER INFORMATION: Xaa is Cys, Tyr, Glu, or absent
<220> FEATURE:
<221> NAME/KEY: MISC_FEATURE
<222> LOCATION: (20)..(20)
<223> OTHER INFORMATION: Xaa is Glu or absent
<220> FEATURE:
<221> NAME/KEY: MISC_FEATURE
<222> LOCATION: (21)..(21)
<223> OTHER INFORMATION: Xaa is Tyr or absent
<220> FEATURE:
<221> NAME/KEY: MISC_FEATURE
<222> LOCATION: (22)..(22)
<223> OTHER INFORMATION: Xaa is Cys or absent

<400> SEQUENCE: 122

Xaa Xaa Xaa Xaa Xaa Xaa Xaa Xaa Xaa Xaa Xaa Xaa Asn Asn Xaa Xaa
1               5                   10                  15

Xaa Xaa Xaa Xaa Xaa Xaa
            20